United States Patent [19]

Nagata et al.

[11] Patent Number: 5,574,136
[45] Date of Patent: Nov. 12, 1996

[54] DNA ENCODING GRANULOCYTE COLONY-STIMULATING FACTOR RECEPTOR AND PROTEIN THEREOF

[75] Inventors: Shigekazu Nagata, Suita; Rikiro Fukunaga, Minoo, both of Japan

[73] Assignee: Osaka Bioscience Institute, Japan

[21] Appl. No.: 923,976

[22] PCT Filed: Mar. 22, 1991

[86] PCT No.: PCT/JP91/00375

§ 371 Date: Sep. 22, 1992

§ 102(e) Date: Sep. 22, 1992

[87] PCT Pub. No.: WO91/14776

PCT Pub. Date: Oct. 3, 1991

[30] Foreign Application Priority Data

Mar. 23, 1990 [JP] Japan ................................ 2-74539
Jul. 3, 1990 [JP] Japan ................................ 2-176629

[51] Int. Cl.$^6$ ........................ C12N 15/12; C07K 14/705; C07K 14/715
[52] U.S. Cl. ........................ 530/350; 536/23.1; 536/23.5; 435/69.1; 530/351
[58] Field of Search ................... 435/69.1, 240.2, 435/252.3, 320.1; 530/350, 351; 536/23.5, 23.52

[56] References Cited

U.S. PATENT DOCUMENTS 4,675,285  6/1987  Clark et al. ........................ 435/172.3
5,422,248  6/1995  Smith et al. ........................ 435/69.1

FOREIGN PATENT DOCUMENTS

WO91/05046  4/1991  European Pat. Off..

OTHER PUBLICATIONS

Yamasaki et al, Science, 241, 1988, pp. 825–828.
Sims et al, Science, 241, 1988, pp. 585–589.
Uzumaki et al, PNAS, 86, 1989, pp. 9323–9326.
Cosman et al, 1990, vol 2(1) pp. 1–31.
Larsen, A. et al., J. Exp. Med., The Rockefeller Univ. Press. vol. 172 "Expression cloning of a human granulocyte colony–stimulating factor receptor: a structural mosaic of hematopoietin receptor, immunoglobulin, and fibronectin domains", pp. 1559–1570 (Dec. 1990).
Park, L. S. et al., Blood, vol. 74, No. 1, "Interleukin–3, GM–CSF, and G–CSF, receptor expression on cell lines and primary leukemia cells: receptor heterogeneity and relationship to growth factor responsiveness" pp. 56–65, (Jul. 1989).

*Primary Examiner*—Marianne P. Allen

[57] ABSTRACT

A murine G-CSF receptor cDNA was cloned from a cDNA library prepared from mouse myeloid leukemia cells and the structure analyzed. A human G-CSF receptor cDNA was then cloned from cDNA libraries constructed from human placenta cells or human histocytic lymphoma cells using the murine G-CSF receptor cDNA as a probe, the structure analyzed and expressed in a host cell transformed with it. The stable production of human G-CSF receptor can be accomplished by transforming a host cell with the cloned G-CSF receptor cDNA and making the transformant express the G-CSF receptor.

5 Claims, 21 Drawing Sheets

```
G-CSFR ( 96) G Y P P A S P S N L S C L M H L T T N S L V C Q W E P G P E T H L P T S F I L K S E R S R A D I C Q Y
PRLR  (  1)   Q S P P G K P E I H K C R S P D - K E T F T C W W N P G T D G L P T N Y S L - - - T Y S K E
GHR   ( 27) T N S S K E P K F T K C R S P E - R E T F S C H W T D E V H H G T K N L G P I Q L F Y T R R N T I Q E
cons                                    C                   W                           (L)

G-CSFR (146) Q G D T I P D C V A K K R - - Q N N C S I P R K N L L L Y Q Y M A I H I H T V N Q A E N M L G S S E S P K L
RPLR  ( 44) G E K T T Y E C P D Y K T S G P N S C F F S K Q Y T S I W K I Y I I T V N A T N Q M G S S S D P L
GHR   ( 76) W T Q E W K E C P D Y V S A G E N S C Y F N S F F T S I W I P Y C I - - K L T S N G G T V D E K C F
cons                    C                                                                           G G-CSFR (194) C L D P M D V V K L E P P M L Q A L D I G P D V V S H Q P G C L W L S W K P W K P S E Y M E Q E C E
RPLR  ( 94) Y D V T Y I V E P E P P R N L T L E V - K Q L K - D K K T Y L W V K W S P P T I T D V K T G W F T
GHR   (124) S V D E I - - V Q P D P P I A L N W T L L N V S L T G I H A D I Q V R W E A P R N A D I Q K G W M V
cons                 (V)          (P)P                                             W G-CSFR (244) L R Y Q P Q L K - - G A N W T L V F H L P S S K D Q F E L C G L H Q A P V Y T L Q M R C I R S S L
RPLR  (142) M E Y E I R L K P E E A E E W E I H F T G H Q - T Q F K V F D L Y P G Q K Y L V Q T R C K - - P D
GHR   (172) L E L E L Q Y E L K Y K E V N E T K W K M M D P I L T - T S V P V Y S L K V D K E Y E V R V R S K Q R - N
cons                  (Y)                  (W)                     (Y)                       R G-CSFR (291) P G F W S P W S P G L Q L R P T M K A P T I R L D T W
RPLR  (207) H G Y W S R W S Q E S V E M P N D F T L K D T T V W
GHR   (219) S G N Y G E F S E V L Y V T L P Q M S Q F T C E E D F
cons        (G)  W S     W S
```

FIG. 7(a)

```
G-CSFR(376)  LLPSEAQNTLVAYNKAGTSS--PTTVFLENEGPA--VTGLHAMAQDLN
CONTAC(745)  MPPSTQYQVKVKAFNSKDGPFSLTAVIYSAQDAPTEVPTDVSVKVLSSS

G-CSFR(422)  TIWVDWEAPSLLP-QGYLIE-WEMSSPSYNNSYKSWMIEPNGNITGILLK-
CONTAC(795)  EISVSWHHVTEKSVEGYQIRYWA---AHDKEAAAQRVQVSNQEYSTKL-

G-CSFR(470)  DNINPFQLYRITVAPLYPGIVGPPVNVYTFAGERAPPHAPALHIKHV-GT
CONTAC(840)  ENLKPNTRYHIDVSAFNSAGYGPPSRTIDITRKAPPSQRPRIISSVRSG

G-CSFR(519)  TWAQLEWVPEAPRLGMIPLTHYTIEWADAGDHSFSVTLNISLHDFVLKHL
CONTAC(890)  SRYIITWDHVKAMSNESAVEGYKVLYRPDGQHE-GKLFSTGKHTIEV-PV

G-CSFR(569)  EPASLYHVYLMATSRAGSTNSTGLTRTLDPSD
CONTAC(938)  PSDGEYVEVRAHNEGGDGEVAQIKISGATAGV
```

FIG. 7(b)

```
G-CSFR(602)  L N I F L C L V L S T T C V V T W L C C K R R G K T S F W S D V P D P A H S S L S S W L P T
IL-4R  (209) L P L G V T I S C L P L F C L F C Q L P S F W D K I - - W D Q I P T P A R S P L - - - V A

G-CSFR(652)  I M T E E T F Q L P S F W D S S V P S I
IL-4R  (253) I I I Q D A - Q V P - L W D K Q T R S Q - - - - 286 a.a. - - - -

G-CSFR(672)  T K I T E L E E D K K P T H W D S E S S G N G S L P A L V Q A Y V L Q G D P R E I S N Q S Q P P I S R
IL-4R  (557) V K Q G A A Q D P G V R P S G D P G Y K A F S L L S S N G I R G D T - - - A A A G T D D D G H

G-CSFR(722)  T G D Q V L Y G Q V - L E S P T S P G V M Q Y - I R S D - S T Q P L L G P L G P T P S P K S Y E N I W F
IL-4R  (604) G G Y K P F Q N P V P N Q S P S S V L F T F G L D T E L S P L N S D P P K S P P E C L G L E L

G-CSFR(769)  H S R P Q E T F V P Q P N Q E D D C V F G P P F D F P - L F Q G I V Y S L T C H L C G H
IL-4R  (654) G L K G D W V K A P P A D Q P K P F G D D L G E I V Y I S S
```

```
A
          GAACCTGGACTGCACCTGGTTTCAGGAACTTCTTCTTGACCGACAAGAGACCAAGCAGCCTGGGCTGCCCAGAGTGCCAACATGGGGAAACTGAGGCTCGGCTTCGGAAAGGTGA
123
-23

239    GAC GAG TGC GGG ATC GTC GCC AGT TCA GCC CCC ATC ATG GCA AGG CTG GGG GAT CCC ATC ACA GCC CTG ATC AAG CAT CTG ACT GCT GCC CTG ATC ATC AAC CAG CAT TGC AGC CAT CTG GAC CCC GAC
  1    Glu Glu Cys Gly Ile Val Ser Val Ala Pro Ile Met Ala Arg Leu Gly Asp Pro Ile Thr Ala Leu Ile Lys His Leu Thr Ala Ala Leu Ile Ile Asn Gln His Cys Ser His Leu Asp Pro Glu

344    CCA CAG ATT CTG TGG AGA CTG CAG CAG CTT CAG CAG CAG CGT CTG TCT GAT GTT CAG CAG GTT GAC CTG CGG GCA ATC CTG TAC CCT CCA GCA ATA CCC CAC AAC
 36    Pro Gln Ile Leu Trp Arg Leu Gln Gln Leu Gln Gln Gln Arg Leu Ser Asp Val Gln Gln Val Asp Leu Arg Ala Ile Leu Tyr Pro Pro Ala Ile Pro His Asn

449    CAC ACT CAG GCC TTT CTC TCC TGC CTG AAC TGG TGC CTG AAC AGC AGC GTT GAG CAG CAG GCC ACC AGC TTC CTG ACT CTG AAG AGT TTC AAG AGG
 71    His Thr Gln Ala Phe Leu Ser Cys Leu Asn Trp Cys Leu Asn Ser Ser Val Glu Gln Gln Ala Thr Ser Phe Leu Thr Leu Lys Ser Phe Lys Arg

554    CTC TCC TGC CTC ATG AAC CTC ACA AGC AGC ACC ATC CTG GAC CCA CCA CAG ACC ACA GAC CCC AAA CAC CTC TTC TAC CTC AAT
106    Leu Ser Cys Leu Met Asn Leu Thr Ser Ser Thr Ile Leu Asp Pro Pro Gln Thr Thr Asp Pro Lys His Leu Phe Tyr Leu Asn

659    CGG GGC AAC TGT CAG ACC CAA GGG GAC TCC ATC CTG GAG GAG CAG ACC TGC CAC CCA AAA CAC TGC CTG AAA CTG GTG GAG ATG CTG
141    Arg Gly Asn Cys Gln Thr Gln Gly Asp Ser Ile Leu Glu Asp Cys His Cys Lys Pro Lys His Cys Leu Lys Leu Val Glu Met

764    ATC GGC ATC ATC GGA GAA GCA GCC CCT GAG AAT GCG GCC CTT GGG CTG CTG GCA TGG AGA GCT CTT CTT GAG CAG CAG CTA GGG CCA CCA TGG GGG CAG GAG CCC AGC TTC TTC
176    Met Gly Ile Ile Gly Glu Ala Ala Pro Glu Asn Ala Ala Leu Gly Leu Leu Ala Trp Arg Ala Leu Leu Glu Gln Gln Leu Gly Pro Pro Trp Gly Gln Glu Pro Ser Phe

869    ACC ATG GAC GAC CCC AGC TGC ATC CCC CTC CCT CGG AGC TGG TGT GAG AAG GCA CTG CTG GAG GCC TAT CAG GAG CAG CCC CCA AAT CAG CAC AAT
211    Thr Met Asp Asp Pro Ser Cys Ile Pro Leu Pro Arg Ser Trp Cys Glu Lys Ala Leu Leu Glu Ala Tyr Gln Glu Gln Pro Pro Asn Gln His Asn

974    CGG CAC AAG CCG GGA GAA GCC TGG ACA CAG CAG CAG CTG CTG GAC CTG GGC CTG GAA GTG CCA CCA GTG GTG GTG GAG CAG GCC ACG CTG GAG GAG CAG
246    Arg His Lys Pro Gly Glu Ala Trp Thr Gln Gln Gln Leu Leu Asp Leu Gly Leu Glu Val Pro Pro Val Val Val Glu Gln Ala Thr Leu Glu Glu Gln

1079   ACC CTG CAG ATA CCC TGC ATC CCC CTC CGT GAC AGG AGG CTG CTG GAC CTC AGC AAC GGC GAA GAC CGG ATC CAA ATC GTC AGA GTT
281    Thr Leu Gln Ile Pro Cys Ile Pro Leu Arg Asp Arg Arg Leu Leu Asp Leu Ser Asn Gly Glu Asp Arg Ile Gln Ile Val Arg Val

1184   GAC ACA AAG CAG CAG CGG CTG GAC GTG ACA CTG AAG CCA GTG CCA GAG GAA CGG AGC CGG ATC GAA GCC CAG CAG GTG GAG CAG TAT GTG GTT
316    Asp Thr Lys Gln Gln Arg Leu Asp Val Thr Leu Lys Pro Val Pro Glu Glu Arg Ser Arg Ile Glu Ala Gln Gln Val Glu Gln Tyr Val Val

1289   TCT TGG AGA CCC TCA GGC GCT CTC GCT ATC CTG CCC CTC CTG CCC ACC TGC TGC CCT TCA GAA GCC GAG GAG GTG GCC CTT
351    Ser Trp Arg Pro Ser Gly Ala Leu Ala Ile Leu Pro Leu Leu Pro Thr Cys Cys Pro Ser Glu Ala Glu Glu Val Ala Leu

1394   GTG GCC TAT AAC TCA GCC GGG ACC TCT CGG GTG TCA GAA AGC AGA GGG CCA CCA GGT CTG CAT GCC ATG GCC CGA GAC CCT CAC
386    Val Ala Tyr Asn Ser Ala Gly Thr Ser Arg Val Ser Glu Ser Arg Gly Pro Pro Gly Leu His Ala Met Ala Arg Asp Pro His
```

2024 / 596
TTG ACC CCA GCC CCA ACA GGA AGA ATC CCC TCT GGC CAA GTC TCC CAG ACC CAG CTC ACA GCA GCC TGG GCT CCT GGG TGC CCA CAA TCA TGG AGG ATC CCT
Leu Thr Pro Ala Pro Thr Gly Arg Ile Pro Ser Gly Gln Val Ser Gln Thr Gln Leu Thr Ala Ala Trp Ala Pro Gly Cys Pro Gln Ser Trp Arg Met Pro

2129 / 631
TCC AGC TGC CCG CTT GCA CCC CAC CCA TCA CCA AGC TCA AGC CGG TGC CCT GGG AGT CCC AGT ATA ACA CAG AGA CCT ATG
Ser Ser Cys Pro Ala Leu Ala Pro His Pro Ser Pro Ser Ser Arg Cys Pro Gly Ser Pro Ser Ile Thr Gln Arg Pro Met

2234 / 666
GTG GCC TCC CCA CTC TGG AGA ATG TGC AGG GGC CAA GAG CAG TTT CCA CCC AGC ATG AAA AGA ACC CCC AGT CCC AGT CTG GCA CCA GCC ATC AGG TCC TTT ATG
Val Ala Ser Pro Leu Trp Arg Met Cys Arg Gly Gln Glu Gln Phe Pro Pro Ser Met Lys Arg Thr Pro Ser Pro Ser Leu Ala Pro Ala Ile Arg Ser Phe Met

2339 / 701
GGC AGC TGC TGG TGG GCA CAA CCT CAA GCC CAG GGC CAG ACT ATC TCC CTG ACT GTG TGG CGG TGC TCT CCC AGC TCC AGT CCA CCA GCC CCA AGT CCT ATG
Gly Ser Cys Trp Trp Ala Gln Pro Gln Ala Gln Gly Gln Thr Ile Ser Leu Thr Val Trp Arg Cys Ser Pro Ser Ser Ser Pro Pro Ala Pro Ser Pro Met

2444 / 736
AGA ACC TCT GGT TCC AGG CCA GCC CCT TGG GGA CCC TGG TAA CCCCAGCCCCCAAGCCAGGAGGAGGACTGTGTCTTTGGGCCACTGC
Arg Thr Ser Gly Ser Arg Pro Ala Pro Trp Gly Pro Trp End

C

2201 / 655
ATG GAG GAG CTG CCC GGA AGA CAG CAG GGA CAG TGG CTG GGG CAG ACA TCT GAA ATG AGC CGT GCT CTC ACC CCA CAT CCT TGT GTG CAG GAT GCC TTC
Met Glu Glu Leu Pro Gly Arg Gln Gln Gly Gln Trp Leu Gly Gln Thr Ser Glu Met Ser Arg Ala Leu Thr Pro His Pro Cys Val Gln Asp Ala Phe

DNA ENCODING GRANULOCYTE COLONY-STIMULATING FACTOR RECEPTOR AND PROTEIN THEREOF

FIELD OF THE INVENTION

This invention relates to an isolated DNA encoding granulocyte colony-stimulating factor receptor. More particularly, it relates to an isolated DNA encoding a receptor peptide capable of specifically binding to a colony-stimulating factor (hereinafter, referred to as G-CSF), an expression vector containing said DNA, a transformant transformed by said vector, and a process for the production of said receptor by culturing said transformant. The present invention also relates to a recombinant G-CSF receptor prepared according to the present process.

BACKGROUND OF THE INVENTION

Proliferation and differentiation of hematopoietic cells are regulated by hormone-like growth and differentiation factors designated as colony-stimulating factors (CSF) (Metcalf, D. Nature 339, 27–30 (1989)). CSF can be classified into several factors according to the stage of the hematopoietic cells to be stimulated and the surrounding conditions as follows: granulocyte colony-stimulation factor (G-CSF), granulocyte-macrophage colony-stimulation factor (GM-CSF), macrophage colony-stimulation factor (M-CSF), and interleukin 3 (IL-3). G-CSF participates greatly in the differentiation and growth of neutrophilic granulocytes and plays an important role in the regulation or blood levels of neutrophils and the activation of mature neutrophils (Nagata, S., "Handbook of Experimental Pharmacology", volume "Peptide Growth Factors and Their Receptors", eds. Sporn, M. B. and Roberts, A. B., Spring-Verlag, Heidelberg, Vol.95/1, pp.699–722 (1990); Nicola, N. A. et al., Annu.Rev.Biochem. 58, pp.45–77 (1989)). Thus, G-CSF stimulates the growth and differentiation of neutrophilic granulocytes through the interaction between cell-surface receptors on precursors of neutrophilic granulocytes to give mainly the neutrophilic granulocytes (Nicola, N. A. & Metcalf, D., Proc. Natl. Acad., Sci. USA, 81, 3765–3769 (1984)).

G-CSF has various biological activities in addition to those mentioned above. For example, G-CSF prepared by recombinant DNA technology has proven to be a potent regulator of neutrophils in vivo using animal model systems (Tsuchiya et al., EMBO J. 6 611–616 (1987); and Nicola et al., Annu. Rev. Biochem. 58, 45–77 (1989)). Recent clinical trials in patients suffering from a variety of hemopoietic disorders have shown that the administration of G-CSF is beneficial in chemotherapy and bone marrow transplantation therapy (Morstyn et al., Trends Pharmacol. Sci. 10, 154–159 (1989)). It is also reported that G-CSF stimulates the growth of tumor cells such as myeloid leukemia cells.

Despite the biological and clinical importance of G-CSF, little is known about the mechanism through which G-CSF exerts its effects. Therefore, it has been needed to elucidate such mechanism to establish more effective treatment and diagnosis for G-CSF-related disorders. For this purpose, the biochemical characterization of specific cell-surface receptors for G-CSF and the evaluation of interaction between G-CSF and the receptor must be performed.

Several reports suggested that the target cells of G-CSF is restricted to progenitor and mature neutrophils and various myeloid leukemia cells (Nicola and Metcalf, Proc. Natl. Acad. Sci. USA, 81, 3765–3769 (1984); Begley et al., Leukemia, 1, 1–8 (1987); and Park et al., Blood 74, 56–65 (1989)). Human G-CSF is a 174 amino acid polypeptide while murine G-CSF consists of 178 amino acids. Human and mouse G-CSFs are highly homologous (72.6%) at the amino acid sequence level, in agreement with the lack of species-specificity between them (Nicola et al, Nature 314, 626–628 (1985)). What makes the research in G-CSF more interesting is that G-CSF receptor has also recently been found in non hemopoietic cells such as human endothelial cells (Bussolino et al., Nature 337, 471–473 (1989)) and placenta (Uzumaki et al., Proc. Natl. Acad. Sci. USA, 86, 9323–9326 (1989)).

As can be seen from the above, the elucidation of the interaction between G-CSF and its receptor should greatly contribute to the development of the treatment or prophylaxis of various diseases including hematopoietic disorders using G-CSF, whereby providing more effective and proper treatments on such diseases. Thus, such elucidation is important not only academically but also clinically. On the other hand, the receptor itself can be useful. For instance, a soluble form of the G-CSF receptor may be useful clinically to inhibit the proliferation of some G-CSF-dependent human myeloid leukemia cells (Santoli et al., J.Immunol. 139, 3348–3354 (1987)). The investigation into the expression of G-CSF receptor in tumor cells such as myeloid leukemia may be beneficial to establish an effective clinical application of G-CSF. Accordingly, owing to the various academic and practical usefulness, a stable supply of a G-CSF receptor-encoding gene and the G-CSF receptor has been demanded.

Recently, the technology of genetic engineering has been used for the production of various physiologically active substances. The production by the genetic engineering is generally carried out by cloning DNA encoding desired polypeptide, inserting said DNA into a suitable expression vector, transforming an appropriate host cell such as microorganism or animal cell by the expression vector, and making the transformant express the desired polypeptide.

To apply the genetic engineering technique to the production of G-CSF receptor, cloning of DNA encoding G-CSF receptor is firstly required. However, cloning cDNA encoding G-CSF receptor was hampered by the low number of receptors present on the cell surface (at most hundreds to 2,000 receptor per cell).

BRIEF DESCRIPTION OF THE DRAWINGS

FIG. 1(A–C) depicts the nucleotide sequence and deduced amino acid sequence of murine G-CSF receptor (SEQ ID NOS:1–2).

FIG. 8a depicts the nucleotide sequence and deduced amino acid sequence of plasmids pHQ3 and pHG12 (SEQ ID NOS:3-4).

FIG. 8b depicts the nucleotide sequence and deduced amino acid sequence in plasmid pHQ2, said sequence being different from that of pHQ3 and corresponding to the sequence downstream from nucleotide 2,034 in said pHQ3 (SEQ ID NOS:5-6).

FIG. 8c depicts the nucleotide sequence and deduced amino acid sequence of the insertion present in pHG11, said sequence being inserted in pHQ3 (SEQ ID NOS: 7-8).

DISCLOSURE OF THE INVENTION

Figure 2A:
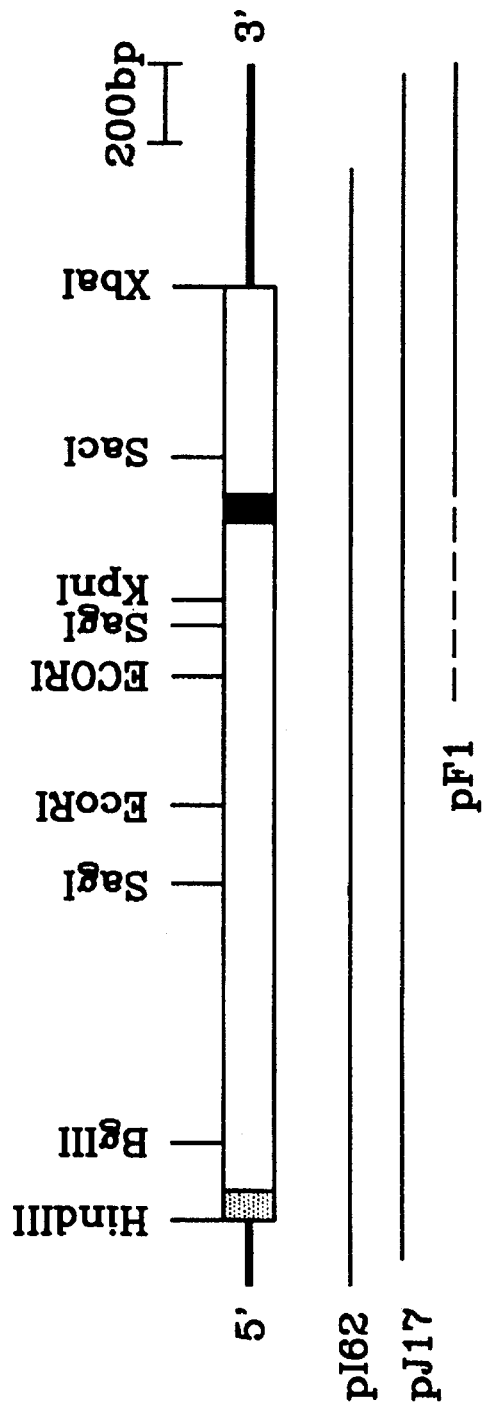
FIG. 2(A–C) depicts a schematic representation and restriction map of murine G-CSF receptor cDNAs (pI62, pJ17 and pF1), and hydropathy plots thereof.

The finding that human and mouse G-CSFs are highly homologous (72.6%) lacking species specificity lead to an presumption that these G-CSFs probably cross-react. Thus, present inventors have studied for the purpose of obtaining a G-CSF receptor which can be used in the research as well as the diagnostic analysis, and succeeded in the purification of the receptor as a protein with a molecular weight (M.W.) of 100,000 to 130,000 from a solubilized mouse G-CSF receptor from mouse myeloid leukemia NFS-60 cells. The purification can be carried out by, for example, extracting cell membrane suspension with CHPAS (3-[(3-cholamidepropyl)dimethylammonio]-1-propanesulfonic acid), treating the extract with G-CSF-affinity chromatography prepared by binding recombinant human G-CSF to the gel resin, and purifying by gel filtration.

Figure 1A:
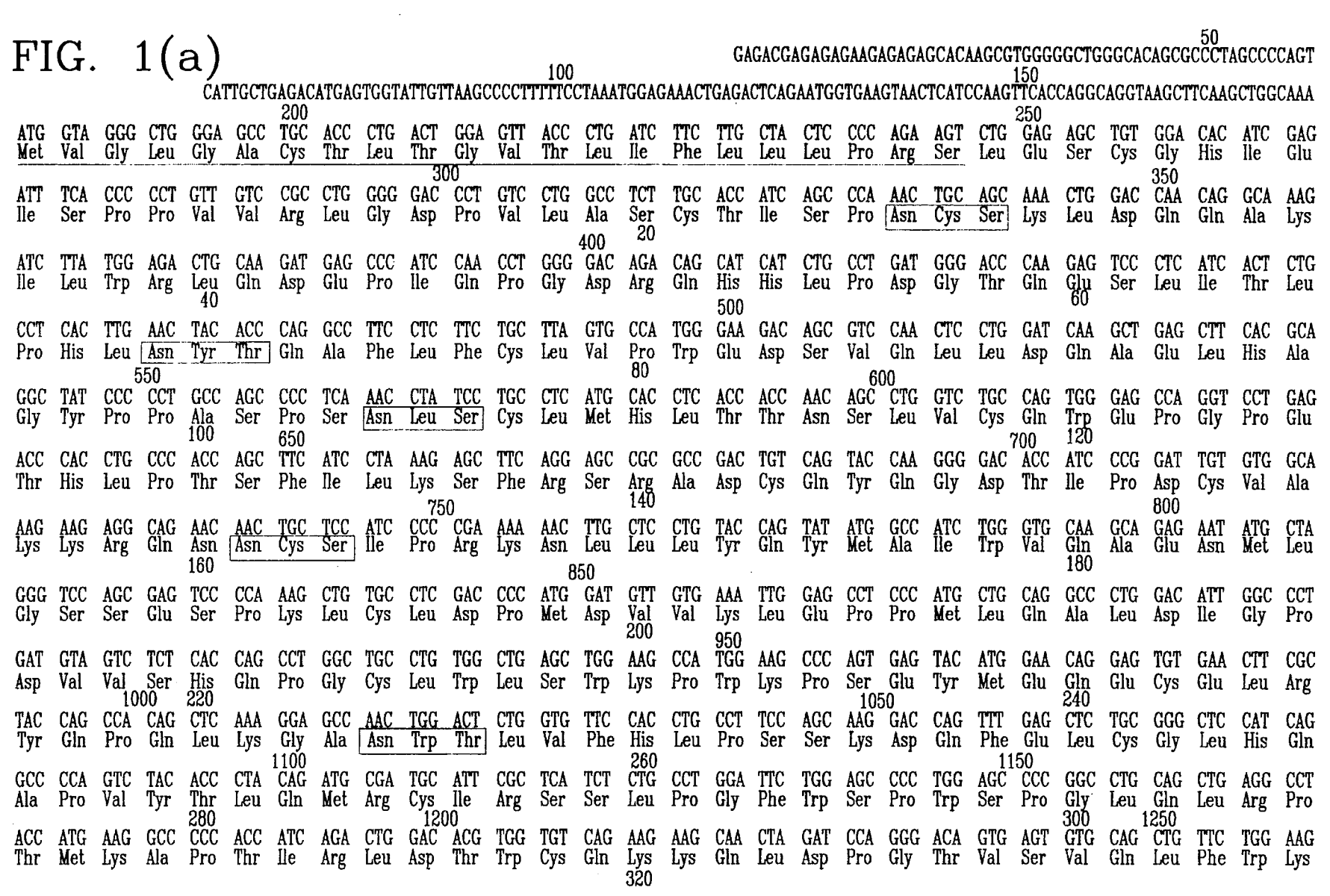
Figure 1B:
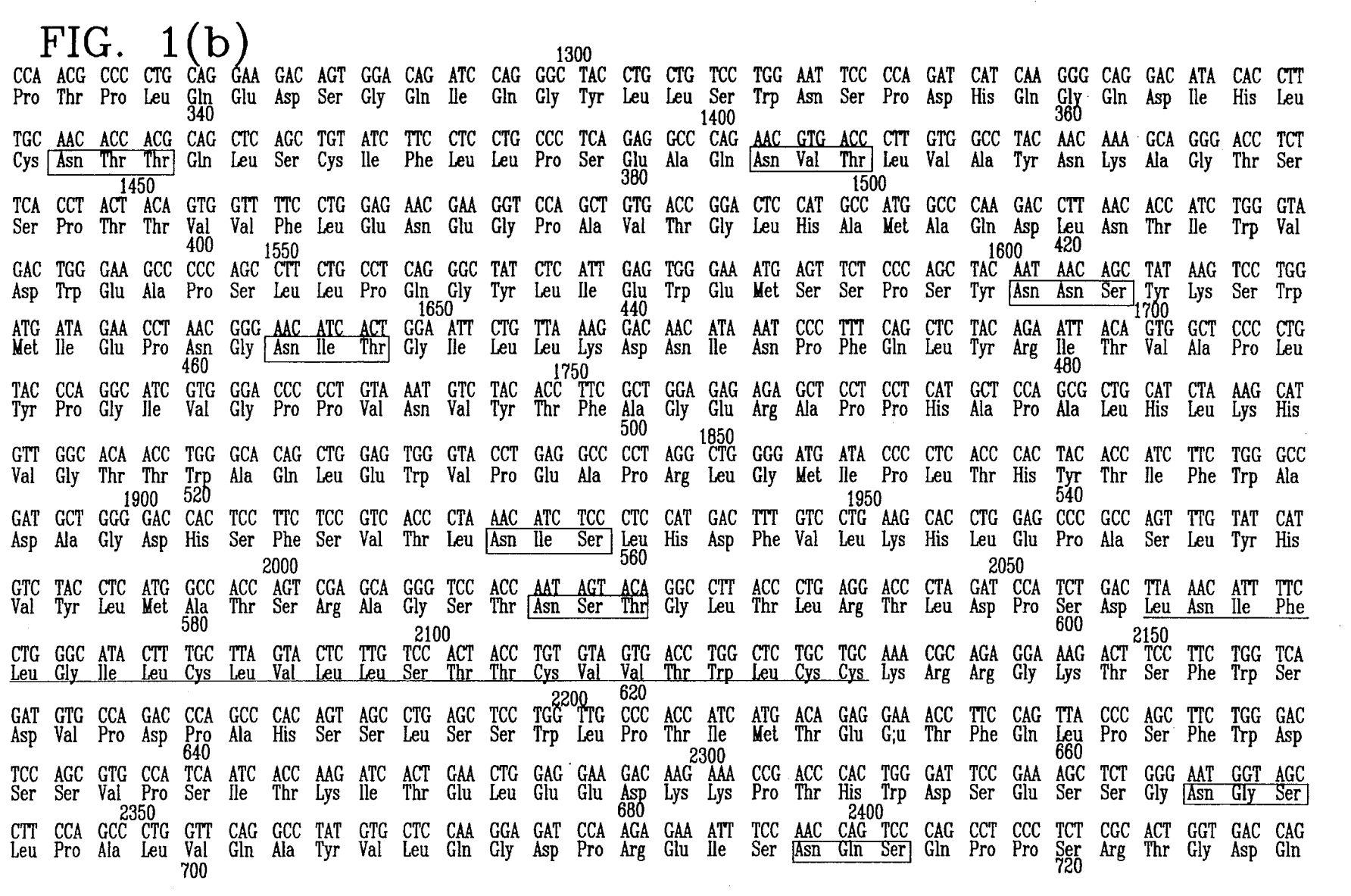
Figure 1C:
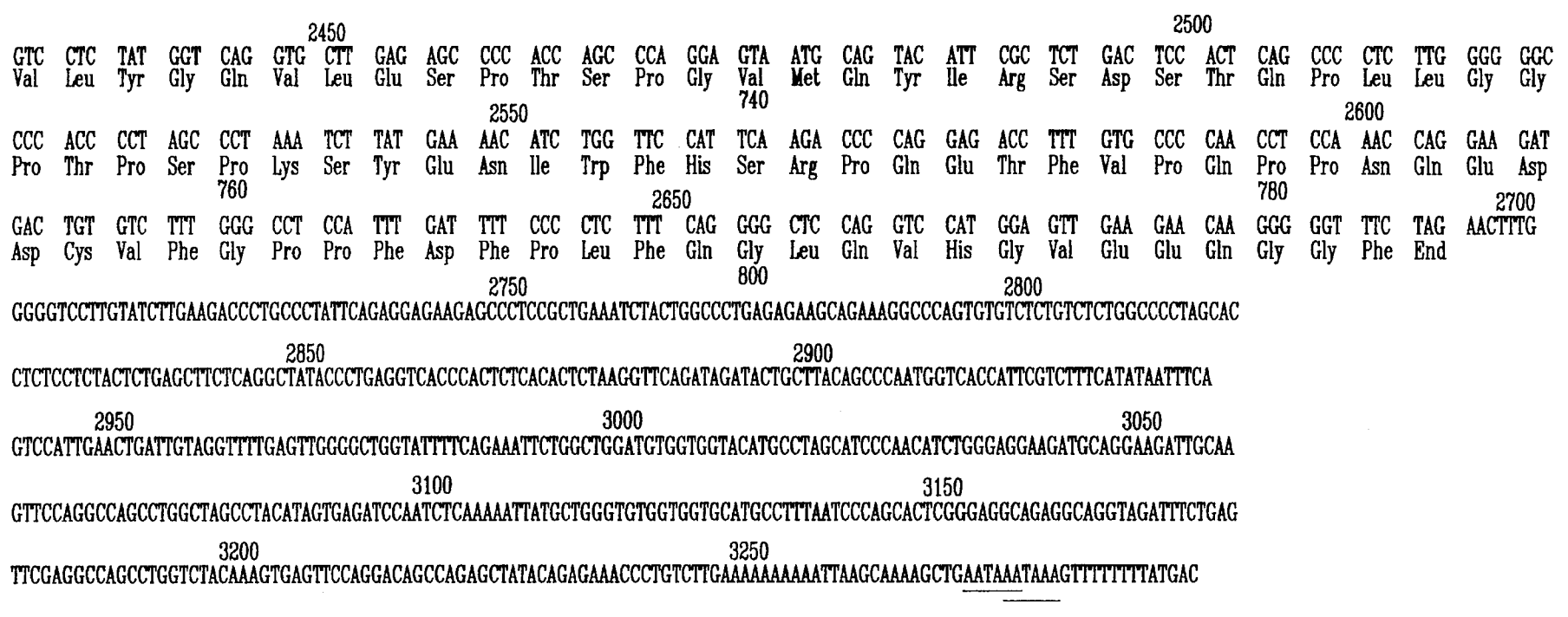

The present inventors have also succeeded in the isolation and cloning of cDNA encoding murine G-CSF receptor (hereinafter, referred to as G-CSF receptor cDNA) by the reverse transcription of mRNA isolated from NFS-60 cells for the first time. Thereafter, the nucleotide sequence of cDNA and deduced amino acid sequence were determined. The nucleotide sequence and predicted amino acid sequence of murine G-CSF receptor cDNA are shown in FIG. 1, and are identified in the Sequence Listing as SEQ ID NO:1 and SEQ ID NO:2. When COS cells were transfected with an expression cloning vector containing murine G-CSF receptor cDNA, said cells expressed a receptor which has similar properties to that of the native G-CSF receptor on NFS-60 cells. Comparison of the amino acid sequence predicted from murine G-CSF receptor cDNA with those of other members belonging to growth factor receptor family revealed that the murine G-CSF receptor possesses many properties commonly found in these members (FIG. 7). A probe prepared from thus obtained murine G-CSF receptor DNA hybridized with human G-CSF receptor, demonstrating that human and murine G-CSF receptors are highly homologous. Therefore, murine G-CSF receptor can serve as so-called "an intermediate" for the preparation of human G-CSF receptor.

As the next step, the present inventors studied with a purpose of providing sufficient amount of human G-CSF receptor and succeeded in the isolation and cloning of cDNA encoding human G-CSF receptor by isolating total mRNA from human placenta and U937 cells, constructing cDNA library, and screening said library using a probe prepared from murine G-CSF receptor cDNA.

When COS cells were transfected with a plasmid encoding human G-CSF receptor of the present invention, said cells expressed a receptor which has similar specific binding properties to that of the native human G-CSF receptor.

Accordingly, the present invention provides an isolated DNA encoding G-CSF receptor. The present invention further provides an expression vector containing G-CSF receptor DNA. The present invention also provides a method for producing G-CSF receptor which comprises transforming a host cell by the expression vector, growing said transformant in a medium, and recovering G-CSF receptor.

For purposes of the invention, the term "G-CSF receptor peptide" herein used refers to both the mature G-CSF receptor peptide and peptide fragments thereof, said fragments having an ability to bind specifically to G-CSF.

The human G-CSF receptor, which has been hardly obtained heretofore, can be easily prepared by the genetic engineering by virtue of the present invention, and in turn used for many studies directed to, for example, the elucidation of the mechanism through which the G-CSF and/or G-CSF receptor exerts the effect, the clinical (for diagnosis and treatment) application, as well as for the promotion of the practical application. Additionally, probes obtained from G-CSF receptor cDNA can facilitate the detection of G-CSF receptors on tumor cells such as leukemia cells before the clinical application of G-CSF during the treatment of patients suffering from these diseases. Therefore, said cDNA is useful to perform an effective clinical application of G-CSF. Furthermore, proteins or compounds capable of binding to G-CSF receptors can be developed by investigating into tertiary structure of soluble-form G-CSF receptor which are prepared in large scale by the DNA recombinant technology.

Cloning of DNA encoding murine G-CSF receptor was carried out as follows. Thus, G-CSF receptor was initially purified from mouse myeloid leukemia NFS-60 cells which have relatively higher expression of the G-CSF receptor and determined the molecular weight of about 100,000 to 130,000 dalton. Total RNA was prepared from NFS-60 cells by the guanidine isothiocyanate/CsCl method, and poly(A) RNA was selected, which was then used for the synthesis of double-stranded cDNA using the reverse transcriptase, DNA polymerase and the like. A cDNA library was constructed in the mammalian expression vector CDM8 (Seed, Nature 329, 840–842 (9187)), as 884 pools of 60 to 80 clones. Plasmid DNAs from each pool were prepared and introduced into COS-7 cells. Two positive pools I62 and J17 which showed significant binding of radioiodinated G-CSF were selected. From these pools were identified plasmids pI62 and pJ17 which have higher binding activity with G-CSF. When plasmids pI62 and pJ17 were transfected into COS-7 cells, resultant cells expressed receptors capable of binding to G-CSF.

The determination of nucleotide sequences of resultant plasmids pJ17 and pI62 revealed that the two cDNAs contain the complete coding sequence of G-CSF receptor but lack the poly(A) tract and poly (A) additional signal. The cDNA library was, therefore, rescreened by colony hybridization using the 2.5 kb HindIII-XbaI fragment of pJ17 as a probe. Among positive clones was selected pF1 which had 603 bp 3' non-coding region and contained two overlapping poly(A) addition signals. The composite nucleotide sequence of the three cloned cDNAs (pI62, pJ17 and pF1) is presented in FIG. 1 together with the predicted amino acid sequence, also identified in the Sequence Listing as SEQ ID NO:1 and SEQ ID NO:2. The schematic representation and restriction map of the hydropathy plot of them are presented in FIG. 2.

The murine G-CSF receptor cDNA cloned by the present invention has the following characteristics.

There is a long open reading frame starting from the initiation codon ATG at nucleotide position 180–182 and ending at the termination codon TAG at position 2691–2693 (2,511 nucleotides). At the 5' upstream from the long open reading frame, three other potential initiation codon ATGs can be found at petitions 73, 105 and 126. All of these are followed by short open reading frames. Deletion of these ATG codons from the cDNA by digesting the plasmid pI62 with HindIII did not increase or decrease the expression level of the recombinant G-CSF receptor in COS cells.

The long open reading frame starts with a stretch of hydrophobic amino acids which seems to serve as a signal sequence. By comparing the 5' portion of the sequence with typical signal peptide cleavage sites, the N-terminal 25 amino acids were assigned as the signal sequence.

The mature murine G-CSF receptor thus consists of 812 amino acids with a calculated molecular weight (M.W.) of 90,814. This M.W. is 5,000 to 35,000 daltons smaller than the M.W. (95,000 to 125,000) estimated from the $^{125}$I-G-CSF cross-linking experiment (Example 2 (2), FIG. 5), or the M.W. of the purified murine G-CSF receptor. The difference is probably due to the attachment of sugar moieties to some of the 11 putative N-glycosylation sites (Asn-X-Thr/Ser) which are found on the extracellular domain of the G-CSF receptor (FIG. 1).

According to the hydropathy plot (FIG. 2, B) (Kyte and Doolite, J.Mol.Biol., 157, 105–132 (1982)) of the amino acid sequence of the mature G-CSF receptor, there exists a stretch of 24 uncharged amino acids extending from Leu-602 to Cys-625, which is followed by three basic amino acids. These properties are consistent with those observed in the membrane-spanning segments of many proteins.

The mature G-CSF receptor thus appears to consist of an extracellular domain of 601 amino acids, a membrane-spanning domain of 24 amino acids (single trans-membrane domain), and a cytoplasmic domain of 187 amino acids. The NH$_2$-terminal half of the extracellular domain is abundant in cysteine residues (17 residues in 373 amino acids), which seems to be a feature common to the ligand-binding domain of many receptors (McDonald et al., British Medical Bulletin 455, 54–569 (1989)). As found in erythropoietin receptor (D'Andrea et al., Cell 57, 277–285 (1989)), the G-CSF receptor is rich in proline (80 residues, 9.9%). Furthermore, the content of tryptophan residues in murine G-CSF receptor is relatively high (26 residues, 3.2%).

As mentioned above, the murine G-CSF receptor of the present invention consists of N-terminal signal sequence, single transmembrane domain, extracellular domain at N-terminal region, and cytoplasmic domain at C-terminal region, which are commonly found features among growth and differentiation factors.

Comparison of amino acid sequence of the murine G-CSF receptor with that of other growth factor receptors, such as growth hormone, prolactin, erythropoietin, IL-6, IL-2, IL-4, IL-3, and GM-CSF receptors revealed the following facts (FIG. 7). In the G-CSF receptor, as is often found in the growth factor receptors, the consensus cysteine and tryptophan residues are conserved, and the "WSXWS" motif (Gearing et al., EMBO J. 83, 667–3676 (1989); and Itoh et al., Science 247, 324–326 (1990)) is also found at amino acid residues 294–298, suggesting that the G-CSF receptor belongs to the family (see, FIG. 7(a)). In this comparison of the G-CSF with other hemopoietic growth factor receptors, it may be noteworthy that the similarity (44.6%) of the G-CSF and IL-6 receptors is less pronounced than that of the G-CSF and prolactin receptors. Furthermore, as shown in FIG. 7(b), the amino acid sequence from 376 to 601 in the extracellular domain of the G-CSF receptor has a significant similarity (42.9%) with a part of the extracellular domain of chicken contactin (Ranscht, J.Cell.Biol. 107, 1561–1573 (1988)). Contactin is a neuronal cell surface glycoprotein of 130 KD and seems to be involved in cellular communication in the nervous system. Since the region from amino acid residues 737 to 818 of contactin can be aligned with the fibronectin type III segment which participates in binding to cells, heparin and DNA, it is possible that this region plays an important role in cell adhesion.

Granulopoiesis occurs daily in bone marrow, and the direct interaction of the neutrophilic progenitor cells with the bone marrow stroma cells has been proposed (Roberts et al., Nature 332 376–378 (1988)). The similarity between a part of extracellular domain of the G-CSF and that of contactin may suggest that this region is involved in the communication of neutrophilic progenitor cells and stroma cells.

The cytoplasmic domain of G-CSF receptor, as observed in other growth factor receptors, is rich in serine (12.8%) and proline (12.3%). When the sequences of transmembrane and cytoplasmic domains of the G-CSF receptor are compared with those of IL-4, a significant similarity was found.

As shown in FIG. 7(c), the transmembrane domain and the first 46 amino acids of the cytoplasmic domain of the G-CSF receptor are homologous (50.0%) to the corresponding regions of the murine IL-4 receptor. Furthermore, amino acid residues 672 to 808 of the G-CSF receptor show significant similarity (45.4%) with amino acid residues 557 to 694 on the IL-4 receptor. These results suggest that the signal transduction by G-CSF and IL-4 may be mediated by a similar mechanism.

In the illustrated Examples of the present invention, cDNA was obtained by reversely transcribing the mRNA isolated from murine leukemia NFS-60 cells. However, the same cDNA can be obtained from other murine cells such as WEHI-3B D$^+$ and bone marrow cells (see, FIG. 6). The cDNA is also homologous to that of other species including human being.

The 3.7 kb mRNA for the G-CSF receptor was detected not only in NFS-60 cells but also in WEHI-3B D$^+$ cells (FIG. 6), suggesting that the same G-CSF receptor is involved in G-CSF-induced proliferation of NFS-60 cells, and differentiation of WEHI-3B D$^+$ cells. The different effects of G-CSF on NFS-60 and WEHI-3B D$^+$ cells, that is, it stimulates the proliferation of NFS-60 cells, while it stimulates the differentiation of WEHI-3B D$^+$ cells, may therefore be mediated by different signal transduction mechanisms downstream of the receptor. In this regard, it is interesting that the c-myb and evi-1 locus, which appear to participate in differentiation of myeloid cells, are rearranged in NFS-60 cells but not WEHI-3B D$^+$ cells (Morishita, et al., Cell 54, 831–840 (1989).

The DNA encoding murine G-CSF receptor can be prepared according to the nucleotide sequence presented in FIG. 1, identified in the Sequence Listing as SEQ ID NO:1. It is available from *Escherichia coli* pI62 by a conventional method, which was originally deposited as a domestic microorganism deposit (FERM P-11353) at the Fermentation Research Institute, Agency of Industrial Science and Technology, Ministry of International Trade and Industry, Japan, on Mar. 9, 1990 and converted into an international one (FERM BP-3312) on Mar. 16, 1991 under the provision of Budapest Treaty. It also can be prepared, for example, by chemical synthesis, or by probing a genomic library or cDNA library using a probe of about 30 nucleotide synthesized on the basis of the sequence of FIG. 1. Such libraries can be constructed from any species expressing G-CSF receptor, for example, human, mouse, rat and the like. The synthesis of a DNA fragment used as a probe, construction of genomic or cDNA library, and the hybridization procedures are well-known to persons ordinary skilled in the art.

Figure 14:
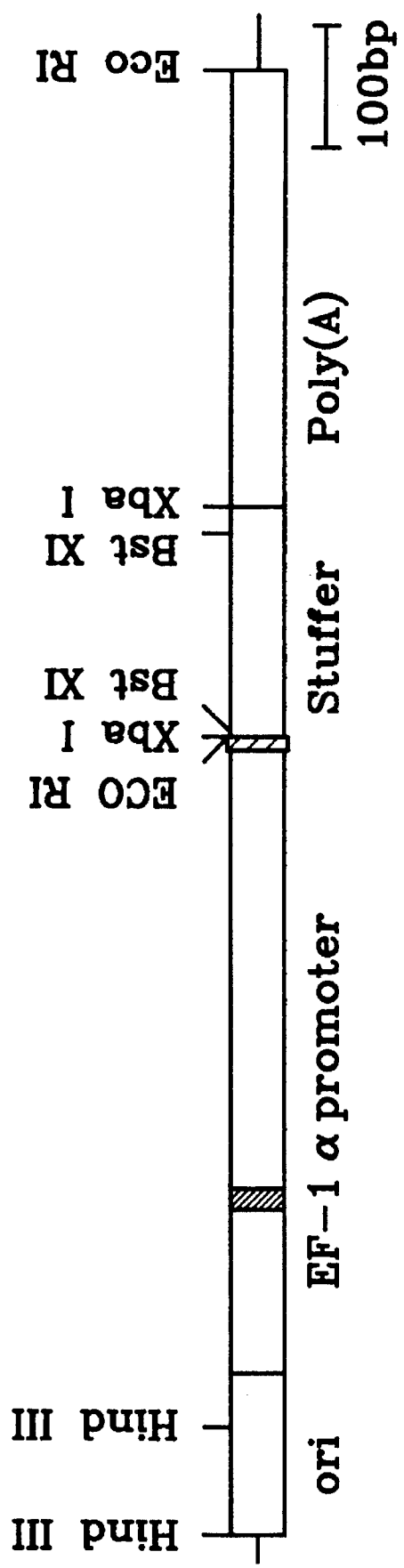
FIG. 14 depicts schematic representation map of expression vector pEF-BOS.

Cloning of cDNA encoding human G-CSF receptor was carried out as follows. Poly (A)RNA was selected from total RNA isolated from human placenta cells and U 937 cells (human histiocytic lymphoma, ATCC CRL 1593), which was used for the synthesis of double-stranded cDNA using a reverse transcriptase, DNA polymerase and the like. A cDNA library was prepared using the mammalian expression vector pEF-BOS (FIG. 14). The cDNA library was screened by colony hybridization or plaque hybridization using a probe prepared from the above-mentioned DNA encoding murine G-CSF receptor and positive clones were selected.

From the cDNA library constructed from mRNA prepared from U937 cells, 5 positive clones (pHQ1–pHQ5) were identified. From the cDNA library constructed from mRNA prepared from human placenta cells, more than 100 positive clones were identified and 6 clones were isolated among them, and digested with EcoRI. The resultant EcoRI fragment was subcloned in pBluescript SK(+). The isolated cDNA clones were analyzed by restriction enzyme mapping and DNA sequence analyses, which revealed that they can be divided into three classes. Most of cDNA clones isolated from U937 and placenta cDNA libraries belonged to class 1.

Class 1: plasmids pHQ3 and pHG 12 (isolated from U937 and placenta cDNA library, respectively).

Figure 8B:
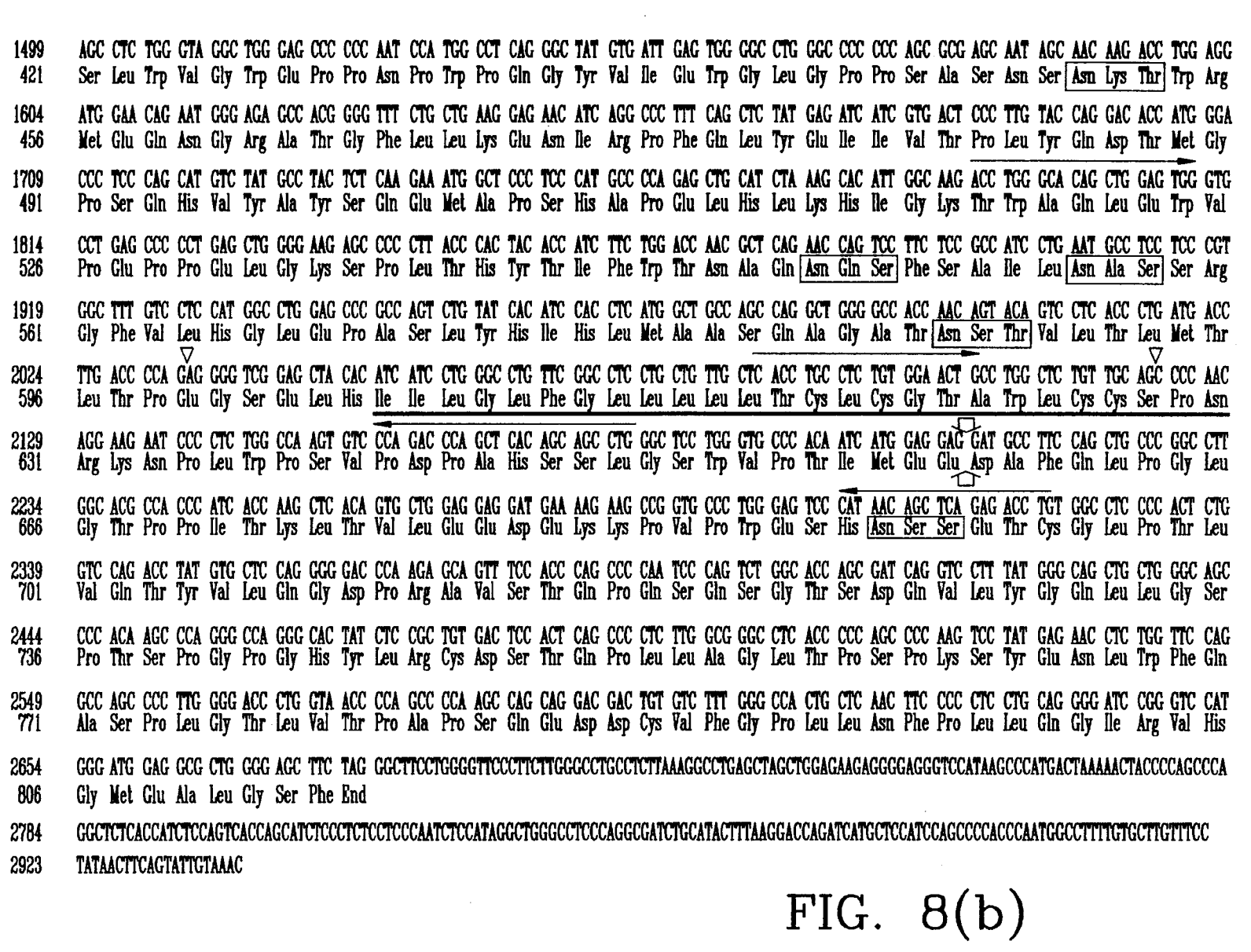

Clones of this class contain a large open reading frame that encodes a protein consisting of 836 amino acids. The nucleotide sequence and deduced amino acid sequence of this cDNA clone is given in FIG. 8A, identified in the Sequence Listing as SEQ ID NO:3 and SEQ ID NO:4. The hydropathy analysis of the predicted amino acid sequence has indicated that the N-terminal 23 amino acid residues correspond to the signal sequence, and following 604, 26 and 183 residues constitute the extracellular, transmembrane and cytoplasmic domains, respectively. The schematic representation and restriction map of plasmid pHQ3 (same as that of pHG12) is given in FIG. 9.

The calculated M.W. (89,743) of mature human G-CSF receptor (813 amino acids) encoded by said plasmid differs from that reported for the native human G-CSF receptor by 30,000–60,000 daltons. This difference may be explained by N-glycosylation at some of 9 potential N-glycosylation sites on the extracellular domain of the receptor.

The overall similarity of human G-CSF receptor to the murine G-CSF receptor is 72% at the nucleotide sequence level and 62.5% at the amino acid sequence level. The amino acid sequence homology is relatively constant over the entire region of the polypeptide. In the extracellular domain of human G-CSF receptor, there are 17 cysteine residues of which 14 are conserved between human and mouse receptors. Furthermore, the "WSXWS" motif conserved in members of a cytokine receptor family can be found in the extracellular domain, which indicates that human G-CSF receptor is one of such members.

Class 2: plasmid pHQ2 (isolated from U937 cDNA library)

The nucleotide sequence of plasmid pHQ2 is identical to that of pHQ3 except that it lacks a region consisting of 88 nucleotide from the nucleotide number 2,034 to 2,121 of pHQ3, which encodes the transmembrane domain. The nucleotide sequence and predicted amino acid sequence in pHQ2, which occurs following the deletion is given in FIG. 8B, identified in the Sequence Listing as SEQ ID NO:5 and SEQ ID NO:6. This deletion results in altered translational reading frame that encodes the additional 150 amino acids downstream from the deletion point. Thus, polypeptide coded by pHQ2 seems to be a secreted, soluble form of G-CSF receptor, which consists of 748 amino acids with a calculated M.W. of 82,707.

Class 3: plasmid pHG11 and pHG5 (isolated from placenta cDNA library)

Figure 9:
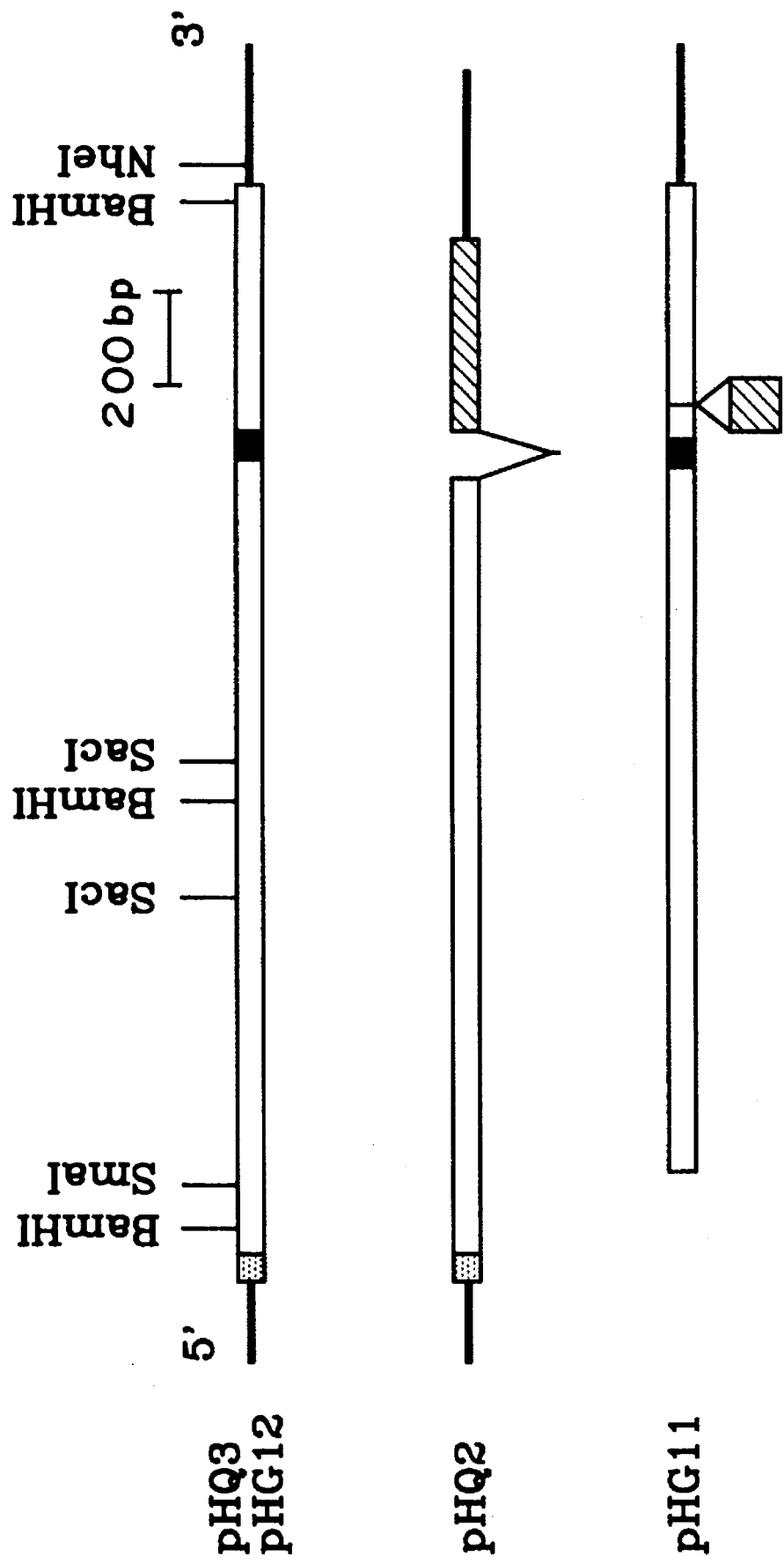
FIG. 9 depicts a schematic representation and restriction map of pHQ3, pHG12, pHQ2 and pHG11 described in FIG. 8.

These plasmids have a 81 bp insertion at nucleotide number 2,210 of plasmid pHQ3. The insertion is in the cytoplasmic domain of the G-CSF receptor, and it does not change the translational open reading frame. The nucleotide sequence and deduced amino acid sequence of the insertion is given in FIG. 8C, identified in the Sequence Listing as SEQ ID NO:7 and SEQ ID NO:8. The putative polypeptide coded by this class of cDNA, therefore, is 27 amino acids (M.W. 2,957) larger than that coded by the class 1 G-CSF receptor. The schematic representation and restriction map of cDNA having this insertion is shown in FIG. 9.

The above three classes of cDNA encoding human G-CSF receptor were examined as to the binding specificity to G-CSF. Murine $^{125}$I-G-CSF could bind to COS cells transfected with pHQ3 in a saturating manner with an equilibrium dissociation constant of 550 pM and $3.4 \times 10^4$ receptor/cell. The dissociation constant of the binding of murine G-CSF to human G-CSF receptor expressed in COS cells was almost similar to that observed in binding of murine G-CSF to murine G-CSF receptor. Since the native human G-CSF receptor expressed on the cell surface of U937 cells can bind human G-CSF with an equilibrium dissociation constant of 424 pM (Park, L. S., Waldron, P. E., Friend, D., Sassenfeld, H. M., Price, V., Anderson, D., Cosman, D., Adrews, R. G., Bernstein, I. D. & Urdal, D. L. Blood 74: 56–65 (1989)), these results suggest that the polypeptide coded by the cDNA in pHQ3 is sufficient to express the high-affinity receptor for human G-CSF.

When binding of murine $^{125}$I-G-CSF to COS cells transfected with pHQ2 of class 2 was examined, a very low level of binding was observed, owing to the deletion present in polypeptide coded by pHQ2. The binding sites per cell were $6 \times 10^3$ and the dissociation constant was 440 pM. These results suggest that the receptor coded by PHQ2, which lacks the transmembrane domain, is probably the one secreted from cells as a soluble form.

To examine the binding specificity of the third class of G-CSF receptor cDNA, an expression plasmid pQw11 was constructed by inserting 5' half of pHQ3 cDNA and 3' half of pHG11 cDNA into a mammalian expression vector pEF-BOS. The resultant transformants were analyzed as to the binding property to the murine $^{125}$I-G-CSF. The results showed that the 27 amino acid insertion in the cytoplasmic domain of the receptor has little effect on the binding of G-CSF to the receptor.

The nucleotide sequence of the DNA of the invention which encodes human G-CSF receptor is shown in FIG. 8, identified in the Sequence Listing as SEQ ID NO:3–SEQ ID NO:8. The DNAs encoding human G-CSF receptor can be isolated from *Escherichia coli* pHQ2, pHQ3 and pHG11 by a conventional method, which were originally deposited as a domestic microorganism deposit (FERM P-11566, 11567, and 11568, respectively) at the Fermentation Research Institute, Agency of Industrial Science and Technology, Ministry of International Trade and Industry, Japan, on Jun. 28, 1990 and transferred to an international one (*Escherichia coli* pHQ2: FERM BP-3313; *Escherichia coli* pHQ3: FERM BP-3314; and *Escherichia coli* pHG11: FERM BP-3315) on Mar. 16, 1991 under the provision of Budapest Treaty.

The present inventors further investigated into various human cells for the presence of G-CSF receptor RNAs by Northern hybridization using probes prepared from human G-CSF receptor cDNA. A single band of 3.7 kb was observed in RNAs from U937, placenta and KG-1 cells. It was confirmed that placenta cells express the largest amounts of G-CSF receptor mRNA among them.

PCR (polymerase chain reaction) was carried out to detect which class of receptor is expressed in these cells. It was concluded by the PCR that both U937 and placenta cells express the class 1 G-CSF receptor. In addition, U937 cells express the soluble form of the class 2 G-CSF receptor, while the G-CSF receptor of class 3 containing the insertion in the cytoplasmic domain is significantly expressed in placenta cells.

The number of the gene coding for G-CSF receptor was examined by Southern hybridization and it was proved that there can be a single gene for G-CSF receptor per human haploid genom.

Since the present invention discloses the nucleotide sequence of DNA encoding human G-CSF receptor, the production of recombinant human G-CSF receptor can be easily accomplished by constructing an expression vector functional in an appropriate host systems using said DNA, transforming a microorganism with the resultant expression vector, and cultivating the transformant. Thus produced recombinant human G-CSF receptor can be used for many purposes such as the diagnosis of leukemia and the elucidation of mechanism of the action of human G-CSF and so on.

The nucleotide sequence of cDNA encoding murine G-CSF receptor is shown in FIGS. 1(*a*), 1(*b*) and 1(*c*), identified in the Sequence Listing as SEQ ID NO:1 ad SEQ ID NO:2, and that of cDNA encoding human G-CSF receptor is shown in FIGS. 8(*a*), 8(*b*) and 8(*c*) identified in the Sequence Listing as SEQ ID NO:3–SEQ ID NO:8. Persons ordinary skilled in the art will appreciates that it is easy to obtain derivatives having a similar activities by modifying said sequence using conventional methods, such as site specific mutation of DNA which comprises the insertion, substitution or deletion of nucleotide(s). Thus obtained DNA derivatives also fall within the scope of the present invention.

It is not always required to use the entire molecule of the mature G-CSF receptor polypeptide for the attainment of purposes of the present invention, but a fragment thereof can be preferably used in some cases subject to that said fragment retains the ability to bind to G-CSF. Similarly, a DNA fragment encoding such a poly peptide fragment of mature G-CSF receptor is useful, as well as the DNA fragment encoding the entire mature G-CSF receptor.

Thus, the present invention provides a receptor peptide capable of binding to G-CSF, and a DNA encoding said peptide.

As can be seen from the above, the DNA of the present invention which encodes G-CSF receptor peptide encompasses a DNA encoding mature G-CSF receptor and DNA fragments encoding peptide fragments having a binding activity to G-CSF.

It is possible to isolate a DNA encoding G-CSF receptor from cells of various animals using the DNA of the invention, construct an expression vector containing said DNA, transform said expression vector into an appropriate cultured cell, and make the resultant transformant produce G-CSF receptor.

The construction of expression vectors containing DNA encoding G-CSF receptor of the invention can be carried out by any of various known methods. Therefore, persons ordinary skilled in the art can select an appropriate method from them. Examples of suitable vectors for the expression of G-CSF receptor are those having a promotor which initiate the transcription, nearby upstream from the site where the DNA is inserted. Appropriate promoters are also known to persons ordinary skilled in the art and can be selected depending on the functional specificity in host cells. For instance, mouse metallothionine promotor and SV40 small T antigen promotor can be used for mouse and simian cells, respectively. Bacterial promoters are also useful for the G-CSF expression in bacterial cells. It is desired that a poly (A) signal exists downstream from the site of the insertion of G-CSF receptor sequence. It is also desired that vectors contain a selectable marker such as a drug-resistance. A particularly preferable marker is a neomycin resistant gene.

The construction of expression vectors can be conducted by inserting the DNA encoding G-CSF receptor in a suitable vector. Suitable vector can be selected from those known to persons ordinary skilled in the art by considering various factors such as promotor, poly(A) signal, selective marker and the like. Examples of vectors in which the cDNA of the invention is inserted to yield an expression vector which in turn is used to transform cultured cells for the expression of cDNA are pSV2, bovine papilloma virus DNA and the like.

Any cultured cells may be used for the expression of G-CSF receptor of the invention as long as they are self-replicable and are capable of expressing the DNAs presented in FIG. 1 or 8 and in the Sequence Listing. Examples of host cells include procaryotic microorganisms such as *Escherichia coli*, eucaryotic cells such as *S. cerevisiae*, and mammalian cells. Tissue cultured cell lines include cultured cells derived from birds, mammalian such as mouse, rat, ape and the like. Selection of suitable host-vector systems and their use are known to persons ordinary skilled in the art and any systems suitable for the expression of cDNA encoding G-CSF receptor can be selected among them.

The following Examples further illustrate and detail the invention disclosed, but should not be considered to limit the invention.

EXAMPLE 1

Cloning of DNA Encoding Murine G-CSF Receptor

1) Cells

Murine myeloid leukemia NFS-60 cells (Weistein et al., Proc.Natl.Acad. Sci. USA, 83, 5010–5014 (1986); and provided by Dr. J.Ihle, St. Jude Children's Research Hospital) were grown in RPMI 1640 medium supplemented with 10% fetal calf serum (FCS) and 10 to 20 units/ml of recombinant mouse IL-3.

COS-7 cells were routainly maintained in a Dulbecco's modified Eagle's medium (DMEM) containing 10% FCS.

2) Growth, Proliferation Factors such as Recombinant G-CSF

Human recombinant G-CSF was purified from medium conditioned with mouse C127I cells which were transformed with the bovine papilloma virus expression vector (Fukunaga et al., Proc. Natl. Acad. Sci. USA 81, 5086–5090 (1984)) carrying human G-CSF cDNA (Tsuchiya et al., 1987, ibid.). Mouse G-CSF was produced by using a similar expression system and purified as homogenous protein. Human recombinant G-CSF and M-CSF produced by chinese hamster ovary cells were provided by Chugai Pharmaceutical Co., LTD.

Human recombinant G-CSF produced by E.coli was purchased from Amersham.

Mouse recombinant IL-3 and GM-CSF were generous gifts from Drs. Miyajima and Arai, DNAX Institute.

Mouse recombinant IL-6 and mouse recombinant LIF were generously provided by Dr. Hirano, Osaka University, and N. Nicola, Walter Eliza Hall Institute, respectively.

Rat prolactin was purchased from Chemicon International Inc.

Mouse recombinant G-CSF was radioiodinated by the IODO-GEN method (Fraker and Speck, Biochem. Biophys. Res. Commun. 80, 849–857 (1978)) with a slight modification. Specific radioactivities ranged from 6 to $8 \times 10^4$ cpm/ng protein (1,200–1,600 cpm/fmole).

3) CDM8 cDNA Library

Total RNA was prepared from exponentially growing NFS-60 cells by the guanidine isothiocyanate/CsCl method, and poly(A) RNA was selected by oligo (dT)-cellulose column chromatography. Double-stranded cDNA was synthesized as described [Nagata, S. et al., Nature 319: 415–418 (1986)] using a kit from Amersham except for the reverse transcriptase which was purchased from Seikagaku Kogyo Co.

To the resultant blunt-ended cDNA was added BstXI adaptor and electrophoresed on 1% agarose gel. From the gel were recovered cDNAs longer than 1.8 kb, which were then ligated to BstXI-digested CDM8 mammalian expression vector (Seed, 1987, ibid) and transformed into E.coli MC1061/p3 cells by electroporation [Dower et al, Nucl.Acids Res., 16, 6127–6145 (1988)].

4) Preparation of DNA

A total of $6 \times 10^4$ bacterial colonies were plated on a 24-well microtiter plate at the density of 60–80 colonies per well. Glycerol cultures were prepared for each pool of colonies. LB broth was inoculated with aliquot from each glycerol culture, and plasmid DNAs were prepared by the boiling method (Maniatis et al., Molecular Cloning: A laboratory Manual, 1982) followed by phenol extraction and ethanol precipitation.

5) Transfection of COS-7 Cells

Monolayers of COS-7 cells were grown in 6-well microtiter plates, and transfection of plasmid DNA into COS-7 cells was carried out by a modified DEAE-dextran method (Sompayrac and Danna, Proc. Natl. Acad. Sci. USA, 78, 7575–7578 (1981)).

In brief, about 50% confluent cells were washed three times with serum-free DMEM, and incubated for 8 hr at 37° C. with 0.6 ml of DMEM containing 50 mM Tris-HCl (pH 7.3), 0.3 mg/ml DEAE-dextran and 1 μg of plasmid DNA. After glycerol shock with Tris-HCl-buffered saline containing 20% glycerol for 2 min at room temperature, cells were washed twice with DMEM, and incubated in DMEM containing 10% FCS.

6) Screening of COS-7 Cells (transformants) Expressing G-CSF Receptor

At 72 hr after the transfection, COS-7 cells were washed with DMEM containing 10% FCS and 20 mM HEPES (pH 7.3) (binding medium), and incubated at 37° C. for 2 hr with $1.7 \times 10^5$ cpm (200 pM) of $^{125}$I-G-CSF in 0.6 ml of the binding medium. Unbound radioiodinated G-CSF was removed, and cells were successively washed three times with phosphate-buffered saline (PBS) supplemented with 0.7 mM $CaCl_2$ and 0.5 mM $MgCl_2$ and once with PBS. Cells were then recovered by trypsinization, and the radioactivity bound to cells was counted using an AUTO-GAMMA 5000 MINAXI γ-counter (Packard). Background binding of $^{125}$I-G-CSF to COS-7 cells transfected with the CDM8 vector was 308±38 (SD) cpm. Two positive pools (I62, J17) were identified, which showed significant binding of radioiodinated G-CSF (500 and 912 cpm) to the transfected COS cells. From each positive pool (I62, J17), 144 independent clones were grown in 24-well microtiter plates (six plates), and subjected to sib selection (Maniatis et al., 1982, ibid) using a matrix of 12×12 clones. After a final round of mini-preparation of plasmid and transfection into COS-7 cells, a single clone was identified from each positive pool by the binding with $^{125}$I-G-CSF.

Figure 2B:
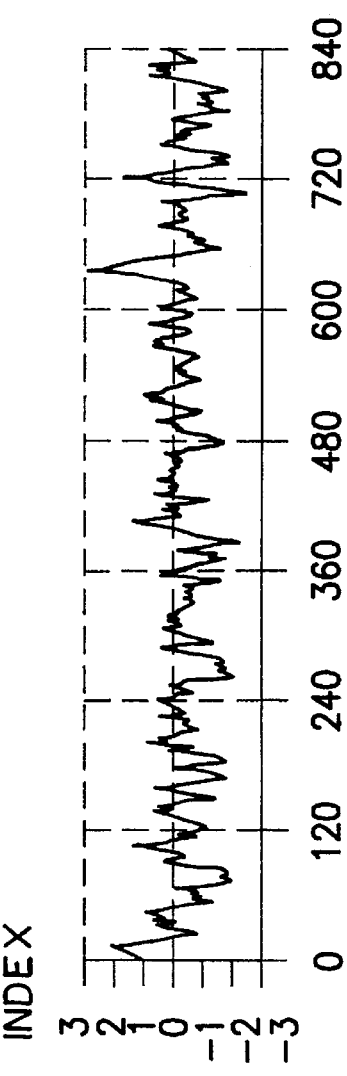

Thus, bacterial clones of pools I62 and J17 were arranged in 12 subgroups of 12 clones each, and assayed as above. Some subgroups gave positive responses, that is, binding reaction of 3,710 to 4,010 cpm of $^{125}$I-G-CSF to COS cells. By assaying single clone from each positive subgroup, two independent clones (pI62 and pJ17) were identified. When plasmid DNAs from pI62 and pJ17 were transfected into COS-7 cells, the binding assay gave values of 30,300 cpm and 31,600 cpm, respectively. When the plasmid DNAs from pI 62 and pJ17 were sequenced, it was found that the two cDNAs contained the complete coding sequence for the G-CSF receptor though, they contained neither the poly(A) tract nor the poly(A) additional signal. The cDNA library was, therefore, rescreened by colony hybridization using the 2.5 kb HindIII-XbaI fragment of pJ17 as a probe, and one positive clone (pF1) was isolated from positive ones. The pF1 clone had 603 bp of 3' non-coding region containing two overlapping poly(A) additional signals. The composite nucleotide sequence of the three cloned cDNAs (pI62, pJ17, and pF1) is presented in FIG. 1 identified in the Sequence Listing as SEQ ID NO:1, together with the predicted amino acid sequence identified in the Sequence Listing as SEQ ID NO:2. Schematic representation and restriction map of three independent cDNAs and hydropathy plot are shown in FIG. 2.

EXAMPLE 2

Characterization of the Cloned Murine G-CSF Receptor

1) Binding activity of the Cloned G-CSF Receptor

The binding of $^{125}$I-G-CSF to COS or NFS-60 cells was examined. COS cells grown on 15 cm plates were transfected with 20 µg of the pI62 or pJ17 plasmid. Cells were split into 6-well microtiter plates at 12 hr after the glycerol shock, and grown for 60 hr in DMEM containing 10% FCS. Cells were washed with binding medium, and incubated at 4° C. for 4 hr with $^{125}$I-G-CSF (10 pM to 1.2 nM range). To determine the non-specific binding of $^{125}$I-G-CSF to cells, a large excess of unlabeled G-CSF (800 nM) was incubated in the assay mixture, and the radioactivity bound to the cells was subtracted from the total binding to yield the specific binding.

Figure 3A:
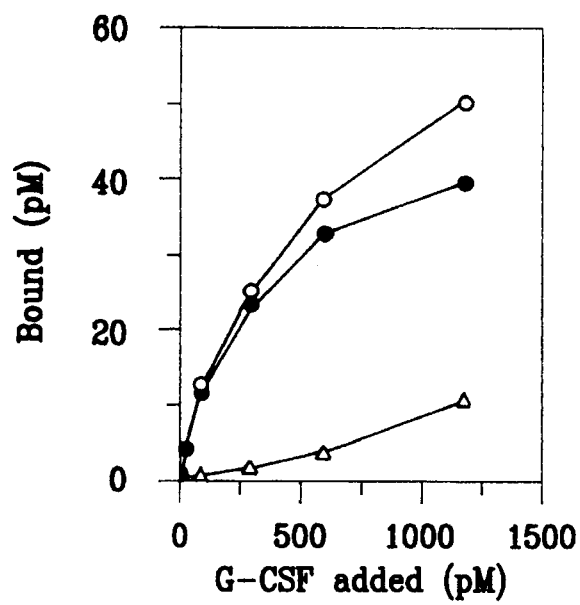
FIG. 3a depicts the saturation binding of murine $^{125}$I-G-CSF to COS cells.
Figure 3B:
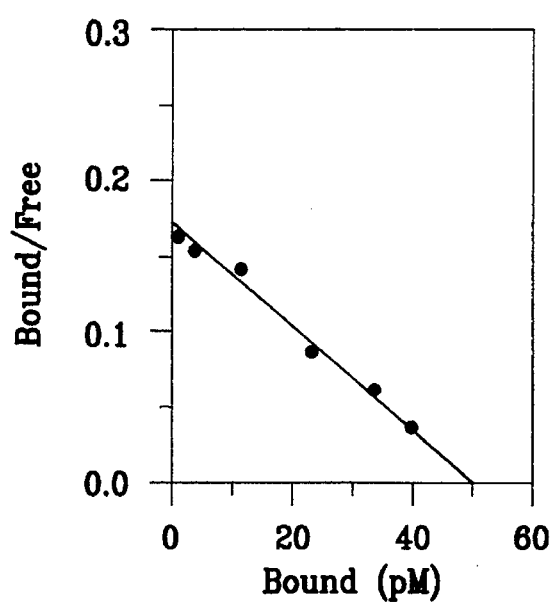
FIG. 3b depicts scatchard plot of binding data of murine $^{125}$I-G-CSF to COS cells.
Figure 3C:
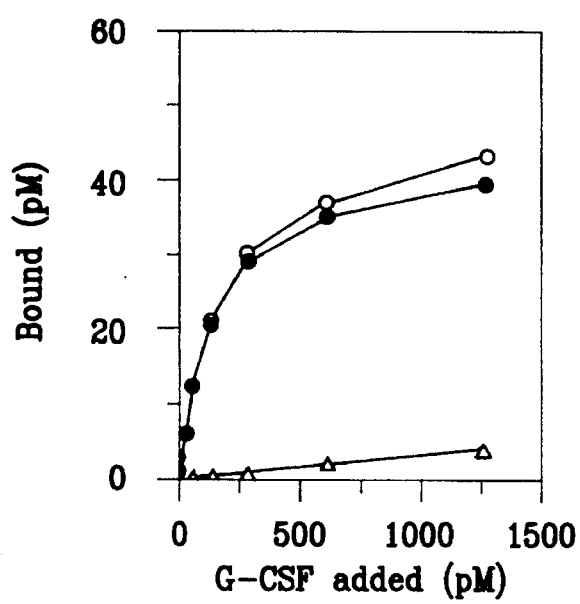
FIG. 3c depicts saturation binding of murine $^{125}$I-G-CSF to NFS-60 cells.
Figure 3D:
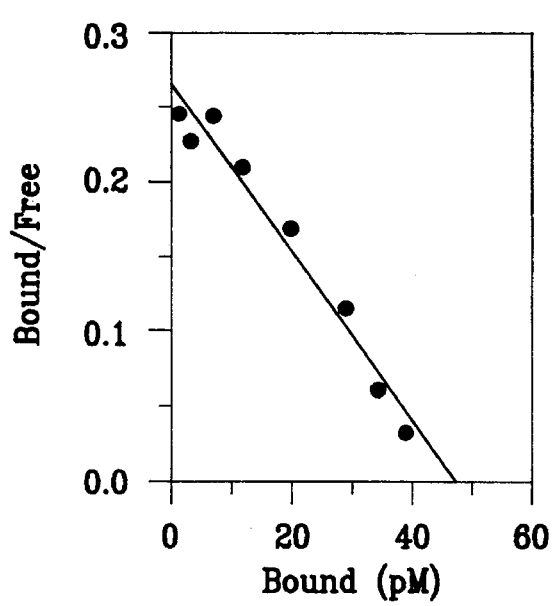
FIG. 3d depicts scatchard plot of binding data of murine $^{125}$I-G-CSF to NFS-60 cells.

For binding of G-CSF to NFS-60 cells, $5.2 \times 10^6$ cells were incubated at 4° C. for 4 hr with various concentrations of $^{125}$I-G-CSF in 0.3 ml of RPMI-1640 medium containing 10% FCS and 20 mM HEPES (pH 7.3). Results are shown in FIG. 3. As mentioned above, $1 \times 10^6$ COS cells transfected with the plasmid pJ17 were incubated with various amounts of $^{125}$I-G-CSF with or without an excess of unlabeled G-CSF. In the FIG. 3A, the specific binding (●) is shown as the difference between total (○) and non-specific binding (Δ). FIG. 3B is the scatchard plot of G-CSF binding data in COS cells, and FIG. 3C is the saturated binding of $^{125}$I-G-CSF to NFS-60 cells, showing total (○), non-specific (Δ) and specific (●) binding to cells. The specific binding is the difference between the total and non-specific binding. FIG. 3D is the scatchard plot of G-CSF binding data on NFS-60 cells. Said Figure shows that the G-CSF receptor expressed on COS cells contains a single species of binding site with an equilibrium dissociation constant of 290 pM and $3.0 \times 10^4$ receptors per cell. If the transfection efficiency of COS cells was assumed to be 10 to 20% (Sympayrac and Danna, Proc. Natl. Acad. Sci. USA, 78, 7575–7578 (1981)), the positively transfected COS cells probably expressed the recombinant G-CSF receptor at $1.5-3.0 \times 10^5$ molecules per cell. Since the native G-CSF receptor on NFS-60 cells has an equilibrium dissociation constant of 180 pM (FIG. 3D), these results suggest that the cDNA coded by the plasmid pJ17 is sufficient to express the high affinity receptor for murine G-CSF.

Figure 4:
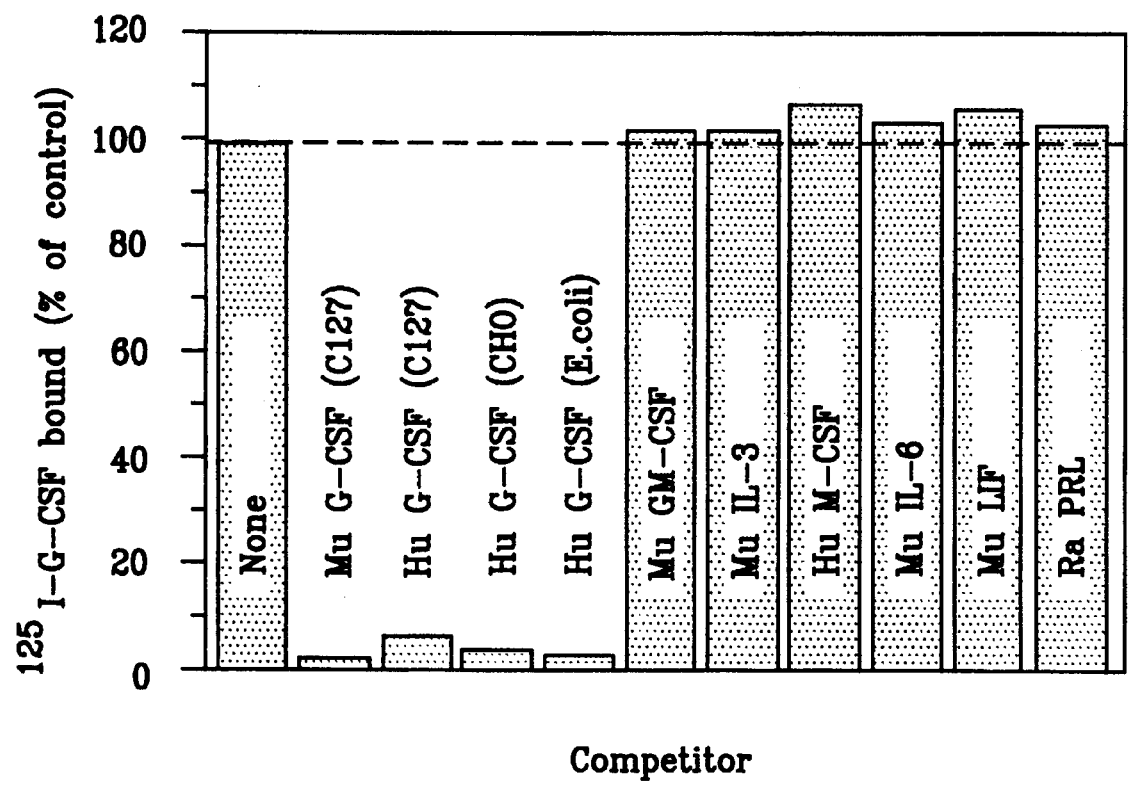
FIG. 4 depicts specific binding of murine G-CSF to recombinant murine G-CSF receptor expressed by COS cells.

The binding specificity of recombinant G-CSF receptor expressed by COS cells to G-CSF was then examined. As mentioned above, COS cells transfected with the cDNA for the G-CSF receptor (pJ17) were incubated with 2 ng of $^{125}$I-mouse-G-CSF in the absence or presence of 1 µg of unlabeled murine G-CSF, human G-CSF, murine GM-CSF, human M-CSF, murine IL-6, murine leukemia inhibitory factor (LIF) or rat prolactin. As human G-CSF, human recombinant G-CSFs produced in mouse C127 cells, Chinese hamster ovary cells or *E. coli* were used. Results are shown in FIG. 4. The radioactivities of $^{125}$I-G-CSF bound to COS cells in each experiment are expressed as a percentage of that obtained without competitor.

Human G-CSF competes with mouse G-CSF for binding to mouse WEHI 3B D$^+$ cells (Nicola et al., 1885, ibid). Accordingly, unlabeled recombinant human G-CSFs produced either by mammalian cells or *E.coli* could compete well with labeled mouse G-CSF for binding to COS cells transfected with the plasmid pJ17 (FIG. 4). On the contrary, no inhibition of binding of $^{125}$I-G-CSF to COS-7 cells was observed in the presence of unlabeled recombinant murine GM-CSF, murine IL-3, murine IL-6, murine LIF, rat prolactin or human M-CSF.

2) Cross-Linking Reaction

The chemical cross-linking reaction of $^{125}$I-G-CSF to the receptor expressed in COS cells was performed as follows.

Figure 5:
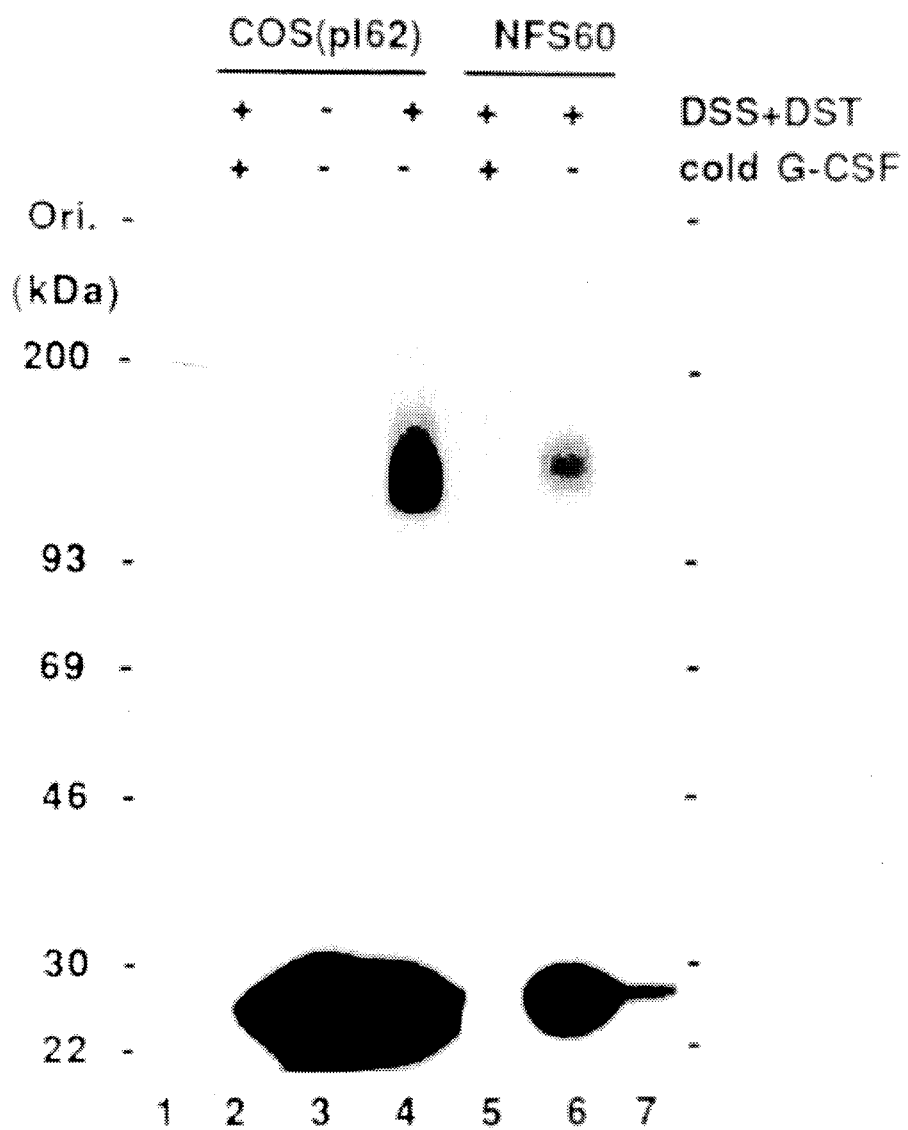
FIG. 5 depicts crosslinking of murine G-CSF receptor expressed in COS cells and those expressed by NFS-60 cells with $^{125}$I-G-CSF.

As mentioned above, $8 \times 10^5$ of COS cells (on 3.5 cm plate) tranfected with the plasmid pI62 were incubated at 4° C. for 2.5 hr with 1.2 nM of the radioiodinated G-CSF in the presence or absence of 1.5 µM of unlabeled G-CSF in 0.6 ml of the binding medium. The cells were scraped from the plate using a cell lifter and washed three times with 1 ml of PBS. Cross-linking reaction was carried out on ice for 20 min in 1 ml of PBS containing 150 µM disuccinimidyl suberate (DSS) and 150 µM disuccunimidyl tartrate (DST). The reaction was terminated by the addition of 50 µl of 1M Tris-HCl (pH 7.4) and cells were collected by centrifugation and were lysed with 15 µl of 1% Triton X-100 containing a mixture of protease inhibitors (2 mM EDTA, 2 mM (p-aminophenyl)methanesulfonylfluoride hydrochloride, 2 mM O-phenanthroline, 0.1 mM leupeptin, 1 µg/ml pepstatin A and 100 units/ml aprotinin). After centrifugation, the clear lysate (10 µl) was analyzed by electrophoresis on a 4–20% gradient polyacrylamide gel in the presence of SDS (Laemmli, Nature 227, 680–685, 1970) and exposed to X-ray film at −80° C. for 2 days with intensifying screens. In the electrophoresis, $^{14}$C-labelled molecular weight standard (Rainbowmarker, Amarsham) was applied as size markers in parallel. Results are shown in FIG. 5. In the figure, lane 2 shows the result obtained by cross-linking reaction in the presence of an excess of unlabeled murine G-CSF, and lanes 3 and 4 show the results obtained in the absence of the same (in the reaction for lane 3, DSS and DST were also omitted). Mouse NFS-60 cells were similarly incubated with $^{125}$I-G-CSF with (lane 5) or without (lane 6) an excess of unlabeled G-CSF which both were cross-linked with DSS and DST. As size markers, $^{14}$C-labeled molecular weight standards (rainbow marker, Amersham) were electrophoresed in parallel (lanes, 1 and 7), and sizes of standard proteins are shown in kd.

The cross-linking reaction of the G-CSF receptor on NFS-60 cells with labeled mouse G-CSF (M.W. 25,000) yielded a band which has an apparent M.W. of 125,000–155,000 (lane 6), indicating that the M.W. of the murine G-CSF receptor on NFS-60 cells is 100,000–130,000. Similarly, cross-linking reaction of $^{125}$I-mouse G-CSF to the receptor expressed on COS cells gave a major band of M.W. 120,000–150,000 (lane 4), which is slightly smaller than that detected on NFS-60 cells. These bands were not observed when the cross-linking reaction was carried out in the presence of unlabeled G-CSF (lanes, 2 and 5) or when the cross-linking agents were omitted (lane 3). The slightly different M.W. observed in COS cells may be explained by the differential glycosylation of receptor in these cell lines.

3) Hybridization

Figure 6:
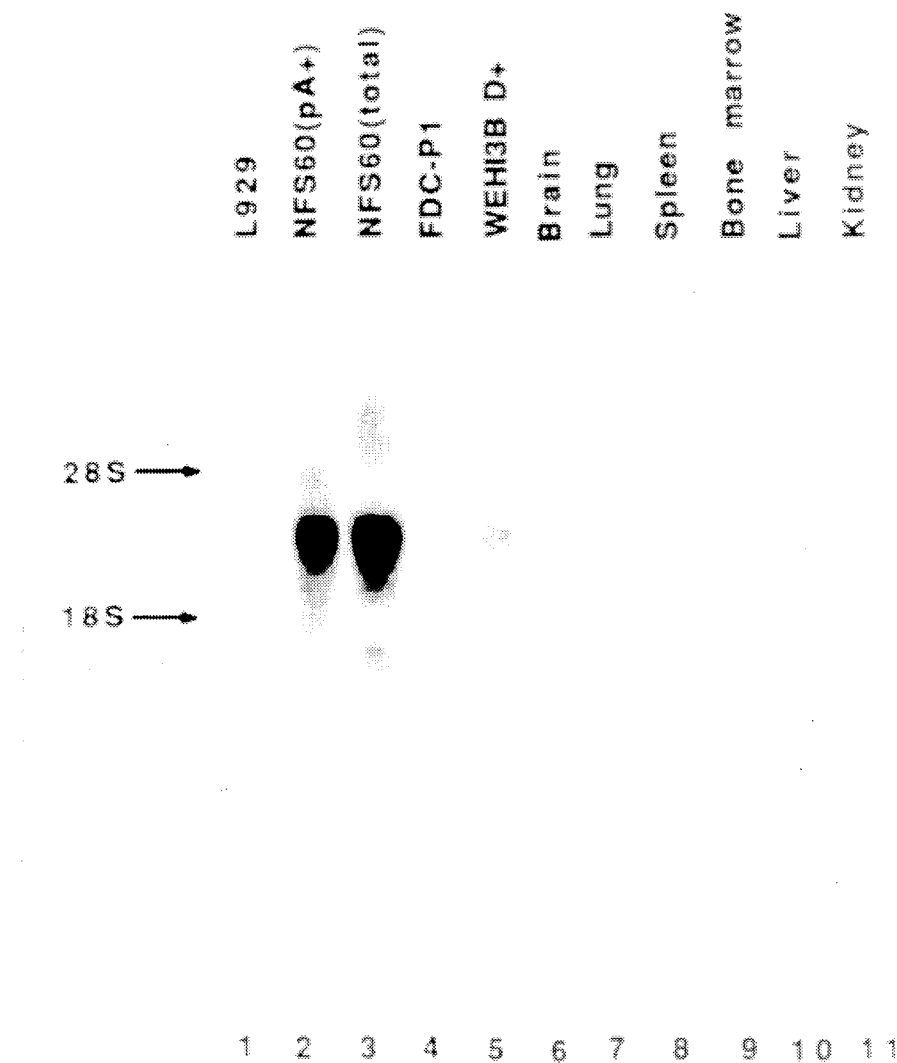
FIG. 6 depicts northern hybridization analysis of murine G-CSF receptor mRNA.

Colony hybridization and Northern hybridization were carried out as described (Maniatis et al., Cold Spring Harbor, N.Y.; Cold Spring Harbor Laboratory (1982)). As a probe, the 2.5 kb HindIII-XbaI fragment of clone pJ17 was labeled with $^{32}$P by the random primer labeling method (Feinberg and Vogelstein, Anal.Biochem. 132, 6–13 (1983)). Results of Northern hybridization are shown in FIG. 6.

Total RNA or poly(A) RNA was prepared from mouse cell lines; L929 (lane 1), NFS-60 (lanes, 2 and 3), FDC-P1 (lane 4), and WEHI-3B D$^+$ (lane 5) or mouse tissues; brain (lane 6), lung (lane 7), spleen (lane 8), bone marrow (lane 9), liver (lane 10), and kidney (lane 11). Total RNA (30 µg; lanes 1, and 3–11) or 2 µg of poly(A) RNA (lane 2) was electrophoresed on a 1.3% agarose gel containing 6.6% formaldehyde, and analyzed by Northern hybridization as described in the above literature.

EXAMPLE 3

Nucleotide Sequence of Cloned Mouse G-CSF Receptor DNA and Amino Acid Sequence of Polypeptide coded by said DNA 1) Determination of Nucleotide Sequence DNA sequencing was performed by the dideoxynucleotide chain termination method using T7-DNA polymerase (Pharmacia) and $\alpha$-$^{35}$S dATP$\alpha$S (Amersham). Results are shown in FIGS. 1 and 2. FIG. 1 represents the nucleotide sequence of murine G-CSF receptor cDNAs (pI62, pJ17 and pF1) and deduced amino acid sequence. Numbers above and below each line refer to nucleotide position and amino acid position, respectively. Amino acids are numbered starting at Cys-1 of the mature G-CSF receptor. On the amino acid sequence, the signal sequence and the transmembrane domain are underlined. Two overlapping poly(A) additional signals (AATAAA) are also underlined. Potential N-glycosylation sites (Asn-X-Ser/Thr) (11 in the extracellular domain and 2 in the cytoplasmic domain) are boxed.

In the FIG. 2 for murine G-CSF receptor cDNA, A gives the schematic representation and restriction map of three independent cDNAs (pI62, pJ17 and pF1) for murine G-CSF receptor. The box represents the open reading frame. The dotted and filled regions indicate the signal sequence and the transmembrane region, respectively. The cleavage sites for restriction enzymes are shown. B is the hydropathy plot of the amino acid sequence of murine G-CSF receptor. The hydropathy plot was obtained by the method of Kyte and Doolite (1982) using a window of 10 residues. The numbers under the figure indicate positions of the amino acid residues of the precursor protein.

2) Comparison of the Amino Acid Sequence of the G-CSF Receptor with that of Other Growth Factor Receptors (FIG. 7)

FIG. 7(a): alignment of the G-CSF receptor with prolactin and growth hormone receptors. The amino acid sequence from 96 to 317 of murine G-CSF receptor is aligned with rat prolactin and human growth hormone receptors to give maximum homology by introducing several gaps (-). Identical residues in two sequences are enclosed by solid lines, and residues regarded as favored substitutions are enclosed by dotted lines. Favored amino acid substitutions are defined as pairs of residues belonging to one of the following groups: S,T,P,A and G; N,D,E and Q; H,R and K; M,I,L and V; F,Y and W. Amino acids conserved in 9 members of the growth factor receptor family (G-CSF, prolactin, growth hormone, erythropoietin, GM-CSF, IL-2β, IL-3, IL-4, and IL-6) are shown under each line with or without brackets. The residues without brackets are conserved in more than 8 members, while the residues with brackets are conserved in 5–7 members in the family.

FIG. 7(b): alignment of the murine G-CSF receptor with contactin. The amino acid sequence from 376 to 601 of the mouse G-CSF receptor is aligned with the amino acid sequence of chicken contactin as described in FIG. 7(a).

FIG. 7(c): alignment of the G-CSF receptor with the IL-4 receptor. The amino acid sequence from 602 to 808 of the mouse G-CSF receptor is aligned with two corresponding regions of mouse IL-4 receptor as above.

Figure 7D:
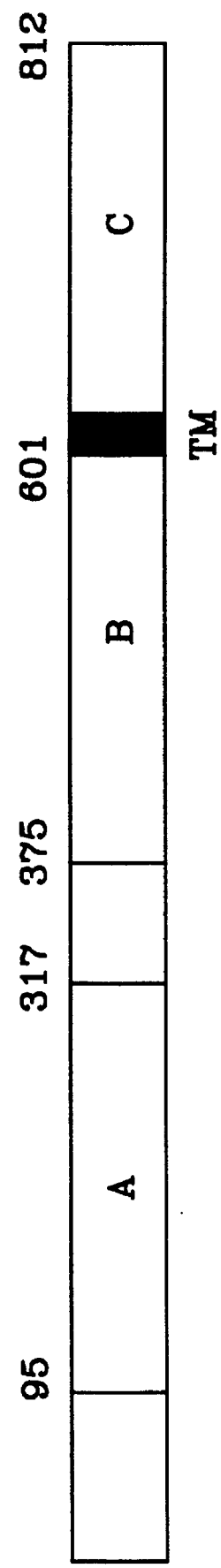
FIG. 7(A–D) depicts alignment of amino acid sequence of murine G-CSF receptor and those of other growth factors and schematic representation of murine G-CSF receptor.

FIG. 7(d): schematic representation of the mouse G-CSF receptor. The box indicates the mature G-CSF receptor. "TM" represents the transmembrane domain. Region "A" indicates a domain (222 amino acids) which has similarity to other growth factor receptors including prolactin and growth hormone receptors, and contains the "WSXWS" motif. Region "B" (226 amino acids) of the mouse G-CSF receptor shows similarity to chicken contactin. Region "C" (211 amino acids) includes the transmembrane domain (underlined) and the cytoplasmic domain of the G-CSF receptor, and is similar to two regions of the mouse IL-4 receptor.

EXAMPLE 4

Cloning of Human G-CSF Receptor (1) Isolation of Human G-CSF Receptor cDNA Clones The preparation of poly(A) RNA from U937 cell and the synthesis of double-stranded cDNA were carried out according to a method described in a literature [Nagata et al., Nature 319: 415–418 (1986)] using a cDNA synthesis kit from Amersham except for the reverse transcriptase which was purchased from Seikagaku Kogyo. To the resultant blunt-ended cDNA was added BstXI adaptor and electrophoresed on 1% agarose gel. From the gel were recovered cDNAs longer than 2.5 kb, which were then ligated to mammalian expression vector pEF-BOS (FIG. 14) and transformed into E.coli DH1 cells by electroporation [Dower et al, Nucl.Acids Res., 16: 6127–6145 (1988)].

A total of $3.4 \times 10^4$ clones of the library was screened by colony hybridization. As a hybridization probe, 2.5 kb HindIII - XbaI DNA fragment of murine G-CSF receptor cDNA was labeled with $^{32}$P using the random oligonucleotide primer labeling method [Sambrook, J., Fritsch, E. F. & Maniatis, T. (1989) Molecular Cloning: A laboratory Manual, 2nd edition (Cold Spring Harbor, N.Y.: Cold Spring Harbor Laboratory)]. The murine G-CSF receptor cDNA (pI62) was used for this purpose whose nucleotide sequence and a deduced amino acid sequence are shown in FIG. 1 identified in the Sequence Listing as SEQ ID NO:1 and SEQ ID NO:2. In the FIG. 1, the signal sequence and transmembrane domain are underlined and potential N-glycosylation sites are boxed.

The hybridization was carried out as described [Fukunaga, R., Matsuyama, M. Okamura, H., Nagata, K, Nagata, S. & Sokawa, Y. Nucl. Res. 14: 4421–4436 (1986)] except that the hybridization temperature was lowered to 28° C. and the filter was washed at 37° C. in 150 mM NaCl/15 mM sodium citrate, pH 7.0/0.1% NaDodSO$_4$. Thus, a replica filter of colony was prepared and each nitrocellulose filter was subjected to hybridization at 28° C. for 12 hr with a probe which had been prepared by heating at 95° C. for 5 min and cooling promptly. The filter was washed as described (ibid) and screened for the presence of desired clones by autoradiography.

A human placental cDNA library prepared in λgt11 (Clonetech) was screened by plaque-hybridization using murine G-CSF receptor cDNA as a probe as described above.

Thus, about $1.5 \times 10^6$ clones of phage DNA were transferred onto nitrocellulose filter as described [Benton, W. D. & Davis, R. W., Science, 196: 180–182 (1977)], which was followed by the screening by plaque hybridization. The screening was conducted using the same probe DNA and under the same conditions as those used in the screening of U937 cDNA library as mentioned above.

Five positive clones (pHQ1–pHQ5) were identified and isolated from U937 cDNA library.

The plaque hybridization between human placenta cDNA library ($1.5 \times 10^6$ clones) and murine G-CSF receptor cDNA gave more than 100 clones having positive signal. EcoRI DNA fragments of six positive clones (λHG4, 5, 11, 12, 14 and 18) were subcloned in pBluescript SK(+) vector to give plasmids pHG4, 5, 11, 12, 14 and 18.

For the DNA sequencing analysis, a series of deletion plasmids, each plasmid containing about 300 bp deletion, was generated using Exonuclease III and mung bean nuclease (Sambrook et al, ibid). The sequencing reaction was performed by the dideoxy chain termination method using T7-DNA polymerase, deaza dGTP and α-$^{35}$SdATPα-S.

The DNA sequencing analysis of the isolated cDNA clones from U937 and placental cDNA libraries has revealed that they can be divided into the following three groups.

Class 1: plasmids pHQ3 and pHG 12 (U937 and placenta cells, respectively).

Most of cDNA clones isolated from U937 and placenta cDNA libraries belong to this class. The nucleotide sequence and deduced amino acid sequence of these plasmids is shown in FIG. 8 (a), and in the Sequence Listing as SEQ ID NO:3 and SEQ ID NO:4, and the restriction map of them is given in FIG. 9.

Plasmid of this class 1 contain a large open reading frame that encodes a protein consisting of 836 amino acids. The hydropathy analysis of the predicted amino acid sequence has indicated that the N-terminal 23 amino acid residues correspond to the signal sequence, and following 604, 26 and 183 residues constitute the extracellular, transmembrane and cytoplasmic domains, respectively, as can be seen from the Figure. There are nine potential N-glycosylation sites on the extracellular domain of the receptor.

In the extracellular domain of the peptide encoded by this cDNA, there are 17 cysteine residues and 14 of which are conserved between human and mouse receptors. Furthermore, the "WSXWS" motif conserved in members of a cytokine receptor family can be found in the extracellular domain, which indicates that human G-CSF receptor is one of such members.

The overall homology of human G-CSF receptor (813 amino acids) to the murine G-CSF receptor is 72% at the nucleotide sequence level and 62.5% at the amino acid sequence level. The amino acid sequence homology is relatively constant over the entire region of the polypeptide.

Class 2: plasmid pHQ2 (U937 cell)

The nucleotide sequence of plasmid pHQ2 is identical to that of pHQ3 except that it lacks 88 nucleotide from 2,034 to 2,121. The ends of the deletion in pHQ 2 is shown by filled arrowheads in FIG. 8 (a). As can be seen from the figure, the deleted region includes the transmembrane domain. The nucleotide sequence which occurs following the 88 bp deletion is given in FIG. 8 (b).

The plasmid pHQ2, in which the deletion results in altered translation reading frame that encodes the additional 150 amino acids after the deletion point (FIG. 9), seems to encode a secreted and soluble form of G-CSF receptor. The soluble form of G-CSF receptor consists of 748 amino acids with a calculated M.W. of 82,707.

Class 3: plasmid pHG11 and pHG5 (placenta)

These plasmids have a 81 bp insertion at nucleotide number 2,210 of plasmid pHQ3. The insertion is in the cytoplasmic domain of the G-CSF receptor. The site of insertion is shown by an arrow of thick line in FIG. 8 (a). The translational open reading frame is not changed. The nucleotide sequence and deduced amino acid sequence of the insertion is given in FIG. 8 (c), identified in the Sequence Listing as SEQ ID NO:7 and SEQ ID NO:8. The putative polypeptide coded by this class of cDNA, therefore, is 27 amino acids (M.W. 2,957) larger than that coded by the class I G-CSF receptor.

The nucleotide sequence and deduced amino acid sequence of plasmids of the above 3 classes are shown in FIG. 8, identified in the Sequence Listing as SEQ ID NO:3–SEQ ID NO:8. In FIG. 8A, numbering of the amino acid sequence of pHQ2 starts at Glu-1 of the putative mature G-CSF receptor. The signal sequence and the transmembrane domain are underlined by thick lines and potential N-glycosylation sites (Asn-X-Thr/Ser) are boxed. The "WSXWS" motif conserved in members of a cytokine receptor family is doubtly underlined. Filled arrowheads mark the ends of the deletion in pHQ2, while the thick arrows indicate the site of the insertion in pHG11. The thin arrows indicate the oligonucleotide primers used for PCR which will be hereinafter described. On B in FIG. 8(c), identified in the Sequence Listing as SEQ ID NO:5 and SEQ ID NO:6, the sequence following the open arrowhead is the nucleotide sequence in pHQ2 and a deduced amino acid sequence, said nucleotide sequence downstream from nucleotide 2,034 being deleted in pHQ3. C in FIG. 8(c), identified in the Sequence Listing as SEQ ID NO:7 and SEQ ID NO:8, shows the nucleotide sequence and deduced amino acid sequence of the insertion present in pHG11, said insertion occurs following amino acid 657 of pHQ3. The inserted sequence is bracketed.

Schematic restriction map of the plasmids of the above 3 classes are shown in FIG. 9. In the figure, boxes represent open reading frames. The shadowed and filled regions represent the signal sequence and transmembrane domain, respectively. The slashed region in pHQ2 indicates that the amino acid sequence in this region differs from those in other cDNAs as a result of an altered open reading frame. The slashed region in pHG11 shows the 27 amino acids encoded by the inserted sequence.

(2) Detection of G-CSF Receptor mRNA in Human Cells

PCR (polymerase chain reaction) was carried out to detect G-CSF receptor mRNA using primers prepared from the above cDNAs.

Figure 12:
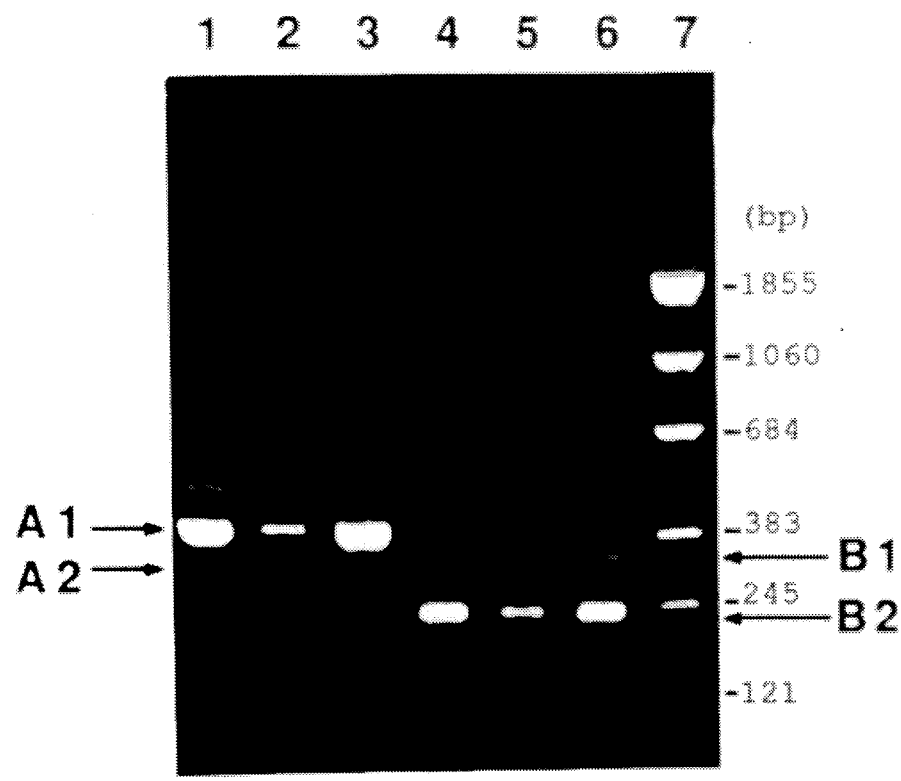
FIG. 12 depicts detection of human G-CSF receptor mRNA by PCR.

The synthesis of single stranded cDNA and PCR was carried out essentially according to the method described by Kawasaki [Kawsaki, E. S. In PCR Protocols, "A guide to methods and application" eds. Innis, M. A., Gelfand, D. H., Shinskly, J. J. & White, T. J. (Academic Press, San Diego, Calif.), pp. 21–27 (1990)]. The results are shown in FIG. 12.

Total RNA (lanes 2 and 5) or poly(A) RNA (lanes 1 and 4) from human U937 cells, or total RNA from human placenta (lanes 3 and 6) was amplified by PCR. Thus, 2 μg of total or poly(A) RNA was subjected to cDNA synthesis in a 50 μl of reaction mixture with 0.5 μg of random hexamer and 80 units of AMV reverse transcriptase as described (Kawasaki, E. S. et al, ibid).

An aliquot (5 μl) of the reaction mixture was diluted with 100 μl of PCR buffer containing 50 pmol each of forward and reverse primer, and placed on a DNA thermal cycler (Perkin-Elmer-Cetus) which was preheated at 80° C. The reaction was started by adding 2.5 units of Taq polymerase, and the conditions for the PCR were: 1.5 min at 95° C.; 1.5 min at 70° C.; 1.5 min at 72° C. for 30 cycles.

When the reaction completes, the products (10% of the reaction mixture) were analyzed by electrophoresis on 1.5% agarose gel in TBE buffer and visualized by ethidium bromide fluorescence. As size markers, BamHI and MvaI-digested pBR322 was electrophoresed in parallel, and sizes of DNA fragments (A1, A2, B1 and B2) corresponding to the isolated cDNAs are indicated by arrows.

In FIG. 12, samples in lanes 1–3 were amplified using the first set of forward and reverse primers from nucleotide 1,790 to 1,810 and 2,179 to 2,156, respectively, while samples in lanes 4–6 were amplified using the second set of primers from nucleotide 2,086 to 2,105 and 2,322 to 2,303. The FIG. 12 demonstrates that both U937 and placental cells express the class 1 G-CSF receptor. In addition, U937 cells express soluble G-CSF receptor, and the placental cells express the G-CSF receptor having the insertion in the cytoplasmic domain.

EXAMPLE 5

Transfection of COS Cells by the Cloned Human G-CSF Receptor cDNA and the Binding Activity of Transformed Cells The binding assay was conducted using COS cells transformed as described in Example 4 and murine $^{125}$I-G-CSF. Labeling of recombinant murine G-CSF, transfection of COS cells with an expression vector containing human G-CSF receptor cDNA and the binding assay using the COS cells and $^{125}$I-G-CSF were carried out in accordance with the procedures described in the aforementioned Examples for murine G-CSF receptor.

A full length cDNA having an insertion in cytoplasmic region was constructed using plasmid pHG11. Thus, plasmid pHG11 was digested thoroughly with restriction enzyme NheI (Takara Shuzo) and then partially digested with BstXI (1,425) (Takara Shuzo). The enzymatic reaction was carried out under the conditions indicated by the manufacture.

An expression plasmid pQW11 was then constructed by ligating 1.38 kb BstXI-NheI fragment and 6.9 kb BstXI-NheI fragment of pHQ3 in the presence of T4 DNA ligase (Takara Shuzo). COS cells were transfected by either of expression plasmids pHQ2, pHQ3 or pQw11 and the binding activity of transfectants to $^{125}$I-G-CSF was analyzed.

Figure 10B:
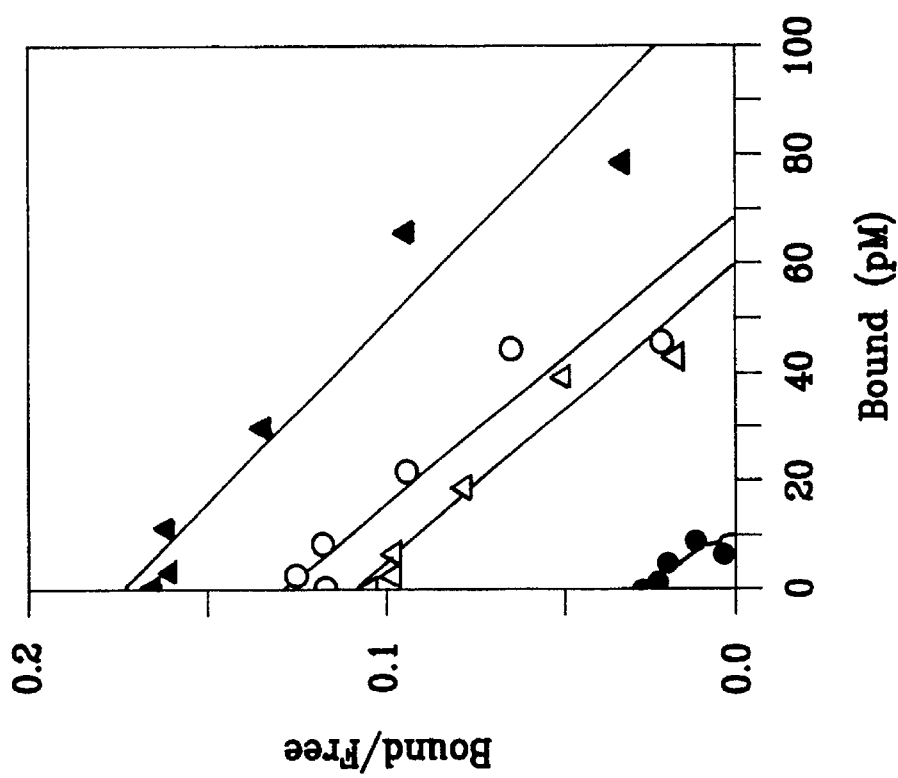
FIG. 10b depicts scatchard plot of G-CSF binding data.
Figure 10A:
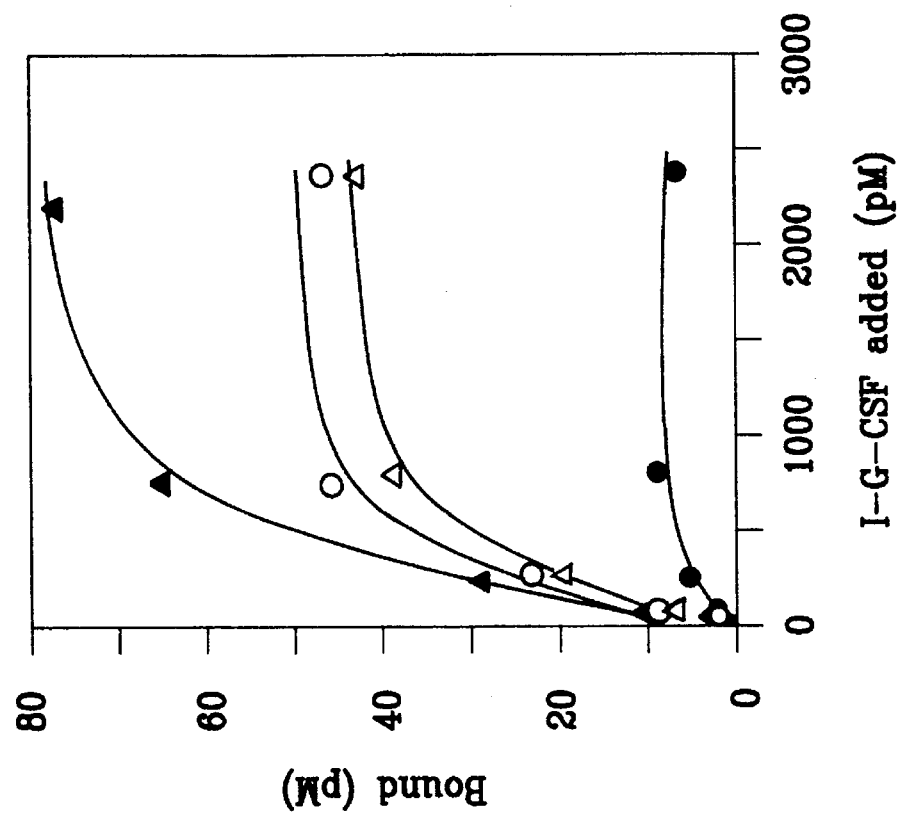
FIG. 10a depicts saturation binding of murine I-CGF to COS cells.

COS cells grown on 15 cm plate were transfected with 20 μg of pHQ2, pHQ3 or pQW11. Cells were divided in 6-well microtiterplate at twelve hours after the glycerin shock and incubated in 10% FCS-containing DMEM for 60 hr. Cells were washed in binding medium (DMEM containing 10% FCS and 20 mM HEPES (pH 7.3)) and incubated with different amounts of $^{125}$I-G-CSF (10 pM to 1.2 nM) at 4° C. for 4 hr. For the determination of non-specific binding between $^{125}$I-G-CSF and cells, the binding reaction was carried out in the presence of a large excess of non-labeled G-CSF (800 nM). The specific binding of $^{125}$I-G-CSF was determined after subtracting the radioactivity bound non-specifically from the total binding activity. FIG. 10A shows the saturation binding of $^{125}$I-G-CSF to COS cells while FIG. 10B shows the scatchard plot of G-CSF binding data. The binding of G-CSF to COS cells transfected with murine G-CSF receptor cDNA was also examined.

In FIG. 10, closed triangle refers to COS cells transfected with murine G-CSF receptor cDNA. Among COS cells transfected with human G-CSF cDNA, cells transfected with pHQ3, pHQ2 and pQW11 are shown by open circle, closed circle and open triangle, respectively.

As shown in FIG. 10, COS cells transfected with pHQ3 or pHQ11 have a strong affinity for murine $^{125}$I-G-CSF. The dissociation constant of the specific binding is 550 pM and the number of receptor per cell is $3.4 \times 10^4$. On the other hand, COS cells transfected with pHQ2 cDNA, which encodes a polypeptide having a deletion, can bind to $^{125}$I-G-CSF in very low level (dissociation constant: 440 pM; binding sites: $6 \times 10^3$/cell). This strongly indicates that the receptor coded by PHQ2, which lacks the transmembrane domain, is probably secreted from cell and accumulated in medium.

Further, COS cells transfected with plasmid pHQ11 has the similar binding activity as that of COS cells transfected with plasmid pHQ3, indicating that 27 amino acid insertion in the cytoplasmic domain has little effect on the binding of G-CSF to the receptor.

The purification of human G-CSF receptor expressed by transformants can be conducted in the similar manner as that described for the purification of native murine G-CSF receptor.

EXAMPLE 6

Analysis of DNA and mRNA Encoding Human G-CSF Receptor

DNA or RNA encoding human G-CSF receptor was analyzed by Northern or Southern Hybridization.

Total RNA was prepared from various cell lines and fresh human full-term placenta by guanidine isothiocyanate/CsCl method as described, and cellular DNA was prepared from human T lymphocytes as described previously (Fukunaga et al, Nucl.Acids Res.,14: 4421–4436 (1986)). Hybridization for Southern and Northern blots were carried out using a 3 kb XhoI DNA fragment of pHQ3 containing human G-CSF receptor cDNA in accordance with the process described in a literature (Maniatis, T. et al, Molecular Cloning, Cold Spring Harbor Laboratory (1982)).

1) Analysis of G-CSF Receptor Transcripts and Genomic DNA

Figure 11:
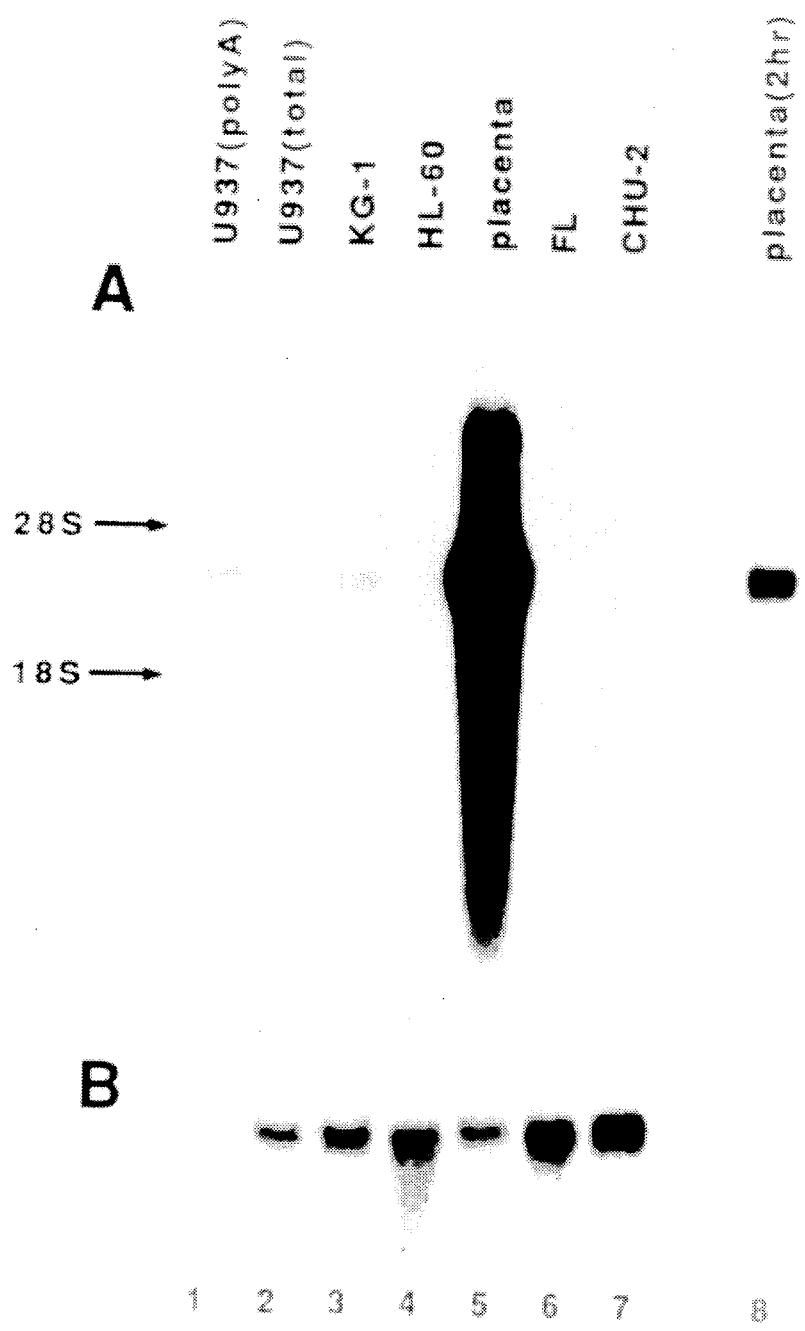
FIG. 11 depicts northern hybridization analysis of human G-CSF receptor mRNA.

Northern hybridization was carried out with mRNAs from various cells using murine G-CSF receptor cDNA as a probe. Results are shown in FIG. 11. Cells used are as follows.

Human U937 (lanes 1 and 2), human KG-1 (lane 3), human HL-60 (lane 4), human FL (lane 6), human CHU-2 (lane 7), human placenta (lanes 5 and 8).

U937: human histiocytic lymphoma, ATCC CRL 1593
KG-1: human acute myelogenous leukemia, ATCC CCL 246
HL-60: human promyelocyte leukemia, ATCC CCL 240
FL: human amnion, ATCC CCL 62

Total RNA (20 μg) (lanes 2 to 6) or poly(A) RNA (1 μg) (Lanes 1 and 7) were used.

In the analysis shown in FIG. 11A, human G-CSF receptor cDNA was used as DNA probes, and the filter was exposed to X-ray film for 40 hr except that the lane 8 was exposed for 2 hr.

A single band of 3.7 kb is observed in RNAs from U937, placenta and KG-1 cells. The signal detected with RNAs from placenta is 20 times or over stronger than that detected with RNAs from U937 cells.

In the analysis shown in panel B, blot was rehybridized with $^{32}$P-labeled human elongation factor 1 α cDNA (Uetsuki, T., Naito, A., Nagata, S. & Kaziro, Y. J. Biol. Chem., 264: 5791–5798 (1990)) and the filter was exposed to X-ray film for 1 hr. In this case, RNAs from various cells give almost the similar signals. These results indicate that the placenta cells express the G-CSF receptor mRNA abundantly, and suggest that G-CSF may have an ability to stimulate the growth and maturation of placenta.

2) Southern Hybridization

The number of the gene coding G-CSF receptor was examined by Southern hybridization.

Figure 13:
FIG. 13 depicts southern hybridization analysis of human G-CSF receptor gene.

Ten microgram of human genomic DNA was digested with EcoRI, HindIII, BamHI, BglII, XbaI, PstI, SacI or ApaI, and electrophoresed on a 0.8% agarose gel. DNA was transferred to a nitrocellulose filter, and hybridized using $^{32}$P labeled human G-CSF receptor cDNA. The DNA size marker was electrophoresed in parallel and is given in kilobases. In FIG. 13, fragments of human genomic DNA generated by the digestion with EcoRI (lane 1), HindIII (lane 2), BamHI (lane 3), BglII (lane 4), XbaI (lane 5), PstI (lane 6), SacI (lane 7), and ApaI (lane 8) were analyzed. One or two bands are observed in EcoRI, HindIII, BglII and XbaI-digested DNA, while digested products of DNA with BamHI, PstI, SacI and ApaI yield 4 to 5 bands, respectively. As can be seen from FIG. 9, human G-CSF receptor cDNA contains 3 BamHI, 6 PstI, 2 SacI and 3 ApaI sites. Accordingly, these results suggest that there is a single gene for G-CSF receptor per human haploid genome.

We claim:

1. An isolated DNA encoding murine G-CSF receptor which encodes the amino acid sequence in SEQ ID NO.: 2.

2. A recombinantly produced murine G-CSF receptor protein having the amino acid sequence of SEQ ID NO.: 2.

3. A recombinantly produced human G-CSF receptor protein having the amino acid sequence of SEQ ID NO.: 6.

4. A recombinantly produced human G-CSF receptor protein having the amino acid sequence of SEQ ID NO.: 8.

5. An isolated DNA encoding murine G-CSF receptor which has the nucleotide sequence in SEQ ID NO.: 1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 3293 base pairs
( B ) TYPE: nucleic acid
( C ) STRANDEDNESS: single
( D ) TOPOLOGY: linear ( i i ) MOLECULE TYPE: cDNA to mRNA ( i x ) FEATURE:
( A ) NAME/KEY: CDS
( B ) LOCATION: 180..2690

( x i ) SEQUENCE DESCRIPTION: SEQ ID NO:1:

```
GAGACGAGAG AGAAGAGAGA GCACAAGCGT GGGGGCTGGG CACAGCGCCC TAGCCCCAGT        60

CATTGCTGAG ACATGAGTGG TATTGTTAAG CCCCTTTTTC CTAAATGGAG AAACTGAGAC       120

TCAGAATGGT GAAGTAACTC ATCCAAGTTC ACCAGGCAGG TAAGCTTCAA GCTGGCAAA        179

ATG GTA GGG CTG GGA GCC TGC ACC CTG ACT GGA GTT ACC CTG ATC TTC         227
Met Val Gly Leu Gly Ala Cys Thr Leu Thr Gly Val Thr Leu Ile Phe
  1               5                  10                  15

TTG CTA CTC CCC AGA AGT CTG GAG AGC TGT GGA CAC ATC GAG ATT TCA         275
Leu Leu Leu Pro Arg Ser Leu Glu Ser Cys Gly His Ile Glu Ile Ser
             20                  25                  30

CCC CCT GTT GTC CGC CTG GGG GAC CCT GTC CTG GCC TCT TGC ACC ATC         323
Pro Pro Val Val Arg Leu Gly Asp Pro Val Leu Ala Ser Cys Thr Ile
         35                  40                  45

AGC CCA AAC TGC AGC AAA CTG GAC CAA CAG GCA AAG ATC TTA TGG AGA         371
Ser Pro Asn Cys Ser Lys Leu Asp Gln Gln Ala Lys Ile Leu Trp Arg
     50                  55                  60

CTG CAA GAT GAG CCC ATC CAA CCT GGG GAC AGA CAG CAT CAT CTG CCT         419
Leu Gln Asp Glu Pro Ile Gln Pro Gly Asp Arg Gln His His Leu Pro
 65                  70                  75                  80

GAT GGG ACC CAA GAG TCC CTC ATC ACT CTG CCT CAC TTG AAC TAC ACC         467
Asp Gly Thr Gln Glu Ser Leu Ile Thr Leu Pro His Leu Asn Tyr Thr
                 85                  90                  95

CAG GCC TTC CTC TTC TGC TTA GTG CCA TGG GAA GAC AGC GTC CAA CTC         515
Gln Ala Phe Leu Phe Cys Leu Val Pro Trp Glu Asp Ser Val Gln Leu
            100                 105                 110

CTG GAT CAA GCT GAG CTT CAC GCA GGC TAT CCC CCT GCC AGC CCC TCA         563
Leu Asp Gln Ala Glu Leu His Ala Gly Tyr Pro Pro Ala Ser Pro Ser
        115                 120                 125

AAC CTA TCC TGC CTC ATG CAC CTC ACC ACC AAC AGC CTG GTC TGC CAG         611
Asn Leu Ser Cys Leu Met His Leu Thr Thr Asn Ser Leu Val Cys Gln
    130                 135                 140

TGG GAG CCA GGT CCT GAG ACC CAC CTG CCC ACC AGC TTC ATC CTA AAG         659
Trp Glu Pro Gly Pro Glu Thr His Leu Pro Thr Ser Phe Ile Leu Lys
145                 150                 155                 160

AGC TTC AGG AGC CGC GCC GAC TGT CAG TAC CAA GGG GAC ACC ATC CCG         707
Ser Phe Arg Ser Arg Ala Asp Cys Gln Tyr Gln Gly Asp Thr Ile Pro
                165                 170                 175

GAT TGT GTG GCA AAG AAG AGG CAG AAC AAC TGC TCC ATC CCC CGA AAA         755
Asp Cys Val Ala Lys Lys Arg Gln Asn Asn Cys Ser Ile Pro Arg Lys
            180                 185                 190

AAC TTG CTC CTG TAC CAG TAT ATG GCC ATC TGG GTG CAA GCA GAG AAT         803
Asn Leu Leu Leu Tyr Gln Tyr Met Ala Ile Trp Val Gln Ala Glu Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 195 |     |     |     |     | 200 |     |     |     |     |     | 205 |     |     |     |      |
| ATG | CTA | GGG | TCC | AGC | GAG | TCC | CCA | AAG | CTG | TGC | CTC | GAC | CCC | ATG | GAT | 851  |
| Met | Leu | Gly | Ser | Ser | Glu | Ser | Pro | Lys | Leu | Cys | Leu | Asp | Pro | Met | Asp |      |
|     | 210 |     |     |     |     | 215 |     |     |     |     | 220 |     |     |     |     |      |
| GTT | GTG | AAA | TTG | GAG | CCT | CCC | ATG | CTG | CAG | GCC | CTG | GAC | ATT | GGC | CCT | 899  |
| Val | Val | Lys | Leu | Glu | Pro | Pro | Met | Leu | Gln | Ala | Leu | Asp | Ile | Gly | Pro |      |
| 225 |     |     |     |     | 230 |     |     |     |     | 235 |     |     |     |     | 240 |      |
| GAT | GTA | GTC | TCT | CAC | CAG | CCT | GGC | TGC | CTG | TGG | CTG | AGC | TGG | AAG | CCA | 947  |
| Asp | Val | Val | Ser | His | Gln | Pro | Gly | Cys | Leu | Trp | Leu | Ser | Trp | Lys | Pro |      |
|     |     |     |     | 245 |     |     |     |     | 250 |     |     |     |     | 255 |     |      |
| TGG | AAG | CCC | AGT | GAG | TAC | ATG | GAA | CAG | GAG | TGT | GAA | CTT | CGC | TAC | CAG | 995  |
| Trp | Lys | Pro | Ser | Glu | Tyr | Met | Glu | Gln | Glu | Cys | Glu | Leu | Arg | Tyr | Gln |      |
|     |     |     | 260 |     |     |     |     | 265 |     |     |     |     | 270 |     |     |      |
| CCA | CAG | CTC | AAA | GGA | GCC | AAC | TGG | ACT | CTG | GTG | TTC | CAC | CTG | CCT | TCC | 1043 |
| Pro | Gln | Leu | Lys | Gly | Ala | Asn | Trp | Thr | Leu | Val | Phe | His | Leu | Pro | Ser |      |
|     |     | 275 |     |     |     |     | 280 |     |     |     |     | 285 |     |     |     |      |
| AGC | AAG | GAC | CAG | TTT | GAG | CTC | TGC | GGG | CTC | CAT | CAG | GCC | CCA | GTC | TAC | 1091 |
| Ser | Lys | Asp | Gln | Phe | Glu | Leu | Cys | Gly | Leu | His | Gln | Ala | Pro | Val | Tyr |      |
|     | 290 |     |     |     |     | 295 |     |     |     |     | 300 |     |     |     |     |      |
| ACC | CTA | CAG | ATG | CGA | TGC | ATT | CGC | TCA | TCT | CTG | CCT | GGA | TTC | TGG | AGC | 1139 |
| Thr | Leu | Gln | Met | Arg | Cys | Ile | Arg | Ser | Ser | Leu | Pro | Gly | Phe | Trp | Ser |      |
| 305 |     |     |     |     | 310 |     |     |     |     | 315 |     |     |     |     | 320 |      |
| CCC | TGG | AGC | CCC | GGC | CTG | CAG | CTG | AGG | CCT | ACC | ATG | AAG | GCC | CCC | ACC | 1187 |
| Pro | Trp | Ser | Pro | Gly | Leu | Gln | Leu | Arg | Pro | Thr | Met | Lys | Ala | Pro | Thr |      |
|     |     |     |     | 325 |     |     |     |     | 330 |     |     |     |     | 335 |     |      |
| ATC | AGA | CTG | GAC | ACG | TGG | TGT | CAG | AAG | AAG | CAA | CTA | GAT | CCA | GGG | ACA | 1235 |
| Ile | Arg | Leu | Asp | Thr | Trp | Cys | Gln | Lys | Lys | Gln | Leu | Asp | Pro | Gly | Thr |      |
|     |     |     | 340 |     |     |     |     | 345 |     |     |     |     | 350 |     |     |      |
| GTG | AGT | GTG | CAG | CTG | TTC | TGG | AAG | CCA | ACG | CCC | CTG | CAG | GAA | GAC | AGT | 1283 |
| Val | Ser | Val | Gln | Leu | Phe | Trp | Lys | Pro | Thr | Pro | Leu | Gln | Glu | Asp | Ser |      |
|     |     | 355 |     |     |     |     | 360 |     |     |     |     | 365 |     |     |     |      |
| GGA | CAG | ATC | CAG | GGC | TAC | CTG | CTG | TCC | TGG | AAT | TCC | CCA | GAT | CAT | CAA | 1331 |
| Gly | Gln | Ile | Gln | Gly | Tyr | Leu | Leu | Ser | Trp | Asn | Ser | Pro | Asp | His | Gln |      |
| 370 |     |     |     |     | 375 |     |     |     |     | 380 |     |     |     |     |     |      |
| GGG | CAG | GAC | ATA | CAC | CTT | TGC | AAC | ACC | ACG | CAG | CTC | AGC | TGT | ATC | TTC | 1379 |
| Gly | Gln | Asp | Ile | His | Leu | Cys | Asn | Thr | Thr | Gln | Leu | Ser | Cys | Ile | Phe |      |
| 385 |     |     |     |     | 390 |     |     |     |     | 395 |     |     |     |     | 400 |      |
| CTC | CTG | CCC | TCA | GAG | GCC | CAG | AAC | GTG | ACC | CTT | GTG | GCC | TAC | AAC | AAA | 1427 |
| Leu | Leu | Pro | Ser | Glu | Ala | Gln | Asn | Val | Thr | Leu | Val | Ala | Tyr | Asn | Lys |      |
|     |     |     |     | 405 |     |     |     |     | 410 |     |     |     |     | 415 |     |      |
| GCA | GGG | ACC | TCT | TCA | CCT | ACT | ACA | GTG | GTT | TTC | CTG | GAG | AAC | GAA | GGT | 1475 |
| Ala | Gly | Thr | Ser | Ser | Pro | Thr | Thr | Val | Val | Phe | Leu | Glu | Asn | Glu | Gly |      |
|     |     |     | 420 |     |     |     |     | 425 |     |     |     |     | 430 |     |     |      |
| CCA | GCT | GTG | ACC | GGA | CTC | CAT | GCC | ATG | GCC | CAA | GAC | CTT | AAC | ACC | ATC | 1523 |
| Pro | Ala | Val | Thr | Gly | Leu | His | Ala | Met | Ala | Gln | Asp | Leu | Asn | Thr | Ile |      |
|     |     | 435 |     |     |     |     | 440 |     |     |     |     | 445 |     |     |     |      |
| TGG | GTA | GAC | TGG | GAA | GCC | CCC | AGC | CTT | CTG | CCT | CAG | GGC | TAT | CTC | ATT | 1571 |
| Trp | Val | Asp | Trp | Glu | Ala | Pro | Ser | Leu | Leu | Pro | Gln | Gly | Tyr | Leu | Ile |      |
|     | 450 |     |     |     |     | 455 |     |     |     |     | 460 |     |     |     |     |      |
| GAG | TGG | GAA | ATG | AGT | TCT | CCC | AGC | TAC | AAT | AAC | AGC | TAT | AAG | TCC | TGG | 1619 |
| Glu | Trp | Glu | Met | Ser | Ser | Pro | Ser | Tyr | Asn | Asn | Ser | Tyr | Lys | Ser | Trp |      |
| 465 |     |     |     |     | 470 |     |     |     |     | 475 |     |     |     |     | 480 |      |
| ATG | ATA | GAA | CCT | AAC | GGG | AAC | ATC | ACT | GGA | ATT | CTG | TTA | AAG | GAC | AAC | 1667 |
| Met | Ile | Glu | Pro | Asn | Gly | Asn | Ile | Thr | Gly | Ile | Leu | Leu | Lys | Asp | Asn |      |
|     |     |     |     | 485 |     |     |     |     | 490 |     |     |     |     | 495 |     |      |
| ATA | AAT | CCC | TTT | CAG | CTC | TAC | AGA | ATT | ACA | GTG | GCT | CCC | CTG | TAC | CCA | 1715 |
| Ile | Asn | Pro | Phe | Gln | Leu | Tyr | Arg | Ile | Thr | Val | Ala | Pro | Leu | Tyr | Pro |      |
|     |     |     |     | 500 |     |     |     |     | 505 |     |     |     |     | 510 |     |      |
| GGC | ATC | GTG | GGA | CCC | CCT | GTA | AAT | GTC | TAC | ACC | TTC | GCT | GGA | GAG | AGA | 1763 |
| Gly | Ile | Val | Gly | Pro | Pro | Val | Asn | Val | Tyr | Thr | Phe | Ala | Gly | Glu | Arg |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 515 |     |     |     |     | 520 |     |     |     |     | 525 |     |     |     |      |
| GCT | CCT | CCT | CAT | GCT | CCA | GCG | CTG | CAT | CTA | AAG | CAT | GTT | GGC | ACA | ACC | 1811 |
| Ala | Pro | Pro | His | Ala | Pro | Ala | Leu | His | Leu | Lys | His | Val | Gly | Thr | Thr |      |
|     | 530 |     |     |     | 535 |     |     |     |     |     | 540 |     |     |     |     |      |
| TGG | GCA | CAG | CTG | GAG | TGG | GTA | CCT | GAG | GCC | CCT | AGG | CTG | GGG | ATG | ATA | 1859 |
| Trp | Ala | Gln | Leu | Glu | Trp | Val | Pro | Glu | Ala | Pro | Arg | Leu | Gly | Met | Ile |      |
| 545 |     |     |     |     |     | 550 |     |     |     |     | 555 |     |     |     | 560 |      |
| CCC | CTC | ACC | CAC | TAC | ACC | ATC | TTC | TGG | GCC | GAT | GCT | GGG | GAC | CAC | TCC | 1907 |
| Pro | Leu | Thr | His | Tyr | Thr | Ile | Phe | Trp | Ala | Asp | Ala | Gly | Asp | His | Ser |      |
|     |     |     |     | 565 |     |     |     |     | 570 |     |     |     |     | 575 |     |      |
| TTC | TCC | GTC | ACC | CTA | AAC | ATC | TCC | CTC | CAT | GAC | TTT | GTC | CTG | AAG | CAC | 1955 |
| Phe | Ser | Val | Thr | Leu | Asn | Ile | Ser | Leu | His | Asp | Phe | Val | Leu | Lys | His |      |
|     |     |     | 580 |     |     |     |     | 585 |     |     |     |     | 590 |     |     |      |
| CTG | GAG | CCC | GCC | AGT | TTG | TAT | CAT | GTC | TAC | CTC | ATG | GCC | ACC | AGT | CGA | 2003 |
| Leu | Glu | Pro | Ala | Ser | Leu | Tyr | His | Val | Tyr | Leu | Met | Ala | Thr | Ser | Arg |      |
|     |     | 595 |     |     |     |     | 600 |     |     |     |     | 605 |     |     |     |      |
| GCA | GGG | TCC | ACC | AAT | AGT | ACA | GGC | CTT | ACC | CTG | AGG | ACC | CTA | GAT | CCA | 2051 |
| Ala | Gly | Ser | Thr | Asn | Ser | Thr | Gly | Leu | Thr | Leu | Arg | Thr | Leu | Asp | Pro |      |
|     | 610 |     |     |     |     | 615 |     |     |     |     | 620 |     |     |     |     |      |
| TCT | GAC | TTA | AAC | ATT | TTC | CTG | GGC | ATA | CTT | TGC | TTA | GTA | CTC | TTG | TCC | 2099 |
| Ser | Asp | Leu | Asn | Ile | Phe | Leu | Gly | Ile | Leu | Cys | Leu | Val | Leu | Leu | Ser |      |
| 625 |     |     |     |     | 630 |     |     |     |     | 635 |     |     |     |     | 640 |      |
| ACT | ACC | TGT | GTA | GTG | ACC | TGG | CTC | TGC | TGC | AAA | CGC | AGA | GGA | AAG | ACT | 2147 |
| Thr | Thr | Cys | Val | Val | Thr | Trp | Leu | Cys | Cys | Lys | Arg | Arg | Gly | Lys | Thr |      |
|     |     |     |     | 645 |     |     |     |     | 650 |     |     |     |     | 655 |     |      |
| TCC | TTC | TGG | TCA | GAT | GTG | CCA | GAC | CCA | GCC | CAC | AGT | AGC | CTG | AGC | TCC | 2195 |
| Ser | Phe | Trp | Ser | Asp | Val | Pro | Asp | Pro | Ala | His | Ser | Ser | Leu | Ser | Ser |      |
|     |     |     | 660 |     |     |     |     | 665 |     |     |     |     | 670 |     |     |      |
| TGG | TTG | CCC | ACC | ATC | ATG | ACA | GAG | GAA | ACC | TTC | CAG | TTA | CCC | AGC | TTC | 2243 |
| Trp | Leu | Pro | Thr | Ile | Met | Thr | Glu | Glu | Thr | Phe | Gln | Leu | Pro | Ser | Phe |      |
|     |     | 675 |     |     |     |     | 680 |     |     |     |     | 685 |     |     |     |      |
| TGG | GAC | TCC | AGC | GTG | CCA | TCA | ATC | ACC | AAG | ATC | ACT | GAA | CTG | GAG | GAA | 2291 |
| Trp | Asp | Ser | Ser | Val | Pro | Ser | Ile | Thr | Lys | Ile | Thr | Glu | Leu | Glu | Glu |      |
|     | 690 |     |     |     |     | 695 |     |     |     |     | 700 |     |     |     |     |      |
| GAC | AAG | AAA | CCG | ACC | CAC | TGG | GAT | TCC | GAA | AGC | TCT | GGG | AAT | GGT | AGC | 2339 |
| Asp | Lys | Lys | Pro | Thr | His | Trp | Asp | Ser | Glu | Ser | Ser | Gly | Asn | Gly | Ser |      |
| 705 |     |     |     |     | 710 |     |     |     |     | 715 |     |     |     |     | 720 |      |
| CTT | CCA | GCC | CTG | GTT | CAG | GCC | TAT | GTG | CTC | CAA | GGA | GAT | CCA | AGA | GAA | 2387 |
| Leu | Pro | Ala | Leu | Val | Gln | Ala | Tyr | Val | Leu | Gln | Gly | Asp | Pro | Arg | Glu |      |
|     |     |     |     | 725 |     |     |     |     | 730 |     |     |     |     | 735 |     |      |
| ATT | TCC | AAC | CAG | TCC | CAG | CCT | CCC | TCT | CGC | ACT | GGT | GAC | CAG | GTC | CTC | 2435 |
| Ile | Ser | Asn | Gln | Ser | Gln | Pro | Pro | Ser | Arg | Thr | Gly | Asp | Gln | Val | Leu |      |
|     |     |     | 740 |     |     |     |     | 745 |     |     |     |     | 750 |     |     |      |
| TAT | GGT | CAG | GTG | CTT | GAG | AGC | CCC | ACC | AGC | CCA | GGA | GTA | ATG | CAG | TAC | 2483 |
| Tyr | Gly | Gln | Val | Leu | Glu | Ser | Pro | Thr | Ser | Pro | Gly | Val | Met | Gln | Tyr |      |
|     | 755 |     |     |     |     | 760 |     |     |     |     | 765 |     |     |     |     |      |
| ATT | CGC | TCT | GAC | TCC | ACT | CAG | CCC | CTC | TTG | GGG | GGC | CCC | ACC | CCT | AGC | 2531 |
| Ile | Arg | Ser | Asp | Ser | Thr | Gln | Pro | Leu | Leu | Gly | Gly | Pro | Thr | Pro | Ser |      |
|     | 770 |     |     |     |     | 775 |     |     |     |     | 780 |     |     |     |     |      |
| CCT | AAA | TCT | TAT | GAA | AAC | ATC | TGG | TTC | CAT | TCA | AGA | CCC | AGG | GAG | ACC | 2579 |
| Pro | Lys | Ser | Tyr | Glu | Asn | Ile | Trp | Phe | His | Ser | Arg | Pro | Gln | Glu | Thr |      |
| 785 |     |     |     |     | 790 |     |     |     |     | 795 |     |     |     |     | 800 |      |
| TTT | GTG | CCC | CAA | CCT | CCA | AAC | CAG | GAA | GAT | GAC | TGT | GTC | TTT | GGG | CCT | 2627 |
| Phe | Val | Pro | Gln | Pro | Pro | Asn | Gln | Glu | Asp | Asp | Cys | Val | Phe | Gly | Pro |      |
|     |     |     |     | 805 |     |     |     |     | 810 |     |     |     |     | 815 |     |      |
| CCA | TTT | GAT | TTT | CCC | CTC | TTT | CAG | GGG | CTC | CAG | GTC | CAT | GGA | GTT | GAA | 2675 |
| Pro | Phe | Asp | Phe | Pro | Leu | Phe | Gln | Gly | Leu | Gln | Val | His | Gly | Val | Glu |      |
|     |     |     | 820 |     |     |     |     | 825 |     |     |     |     | 830 |     |     |      |
| GAA | CAA | GGG | GGT | TTC | TAGAACTTTG | GGGGTCCTTG | TATCTTGAAG | ACCCTGCCCT | | | | | | | | 2730 |
| Glu | Gln | Gly | Gly | Phe |     |     |     |     |     |     |     |     |     |     |     |      |

```
                 835
ATTCAGAGGA   GAAGAGCCCT   CCGCTGAAAT   CTACTGGCCC   TGAGAGAAGC   AGAAAGGCCC      2790

AGTGTGTCTC   TGTCTCTGGC   CCCTAGCACC   TCTCCTCTAC   TCTGAGCTTC   TCAGGCTATA      2850

CCCTGAGGTC   ACCCACTCTC   ACACTCTAAG   GTTCAGATAG   ATACTGCTTA   CAGCCCAATG      2910

GTCACCATTC   GTCTTTCATA   TAATTTCAGT   CCATTGAACT   GATTGTAGGT   TTTGAGTTGG      2970

GGCTGGTATT   TTCAGAAATT   CTGGCTGGAT   GTGGTGGTAC   ATGCCTAGCA   TCCCAACATC      3030

TGGGAGGAAG   ATGCAGGAAG   ATTGCAAGTT   CCAGGCCAGC   CTGGCTAGCC   TACATAGTGA      3090

GATCCAATCT   CAAAAATTAT   GCTGGGTGTG   GTGGTGCATG   CCTTTAATCC   CAGCACTCGG      3150

GAGGCAGAGG   CAGGTAGATT   TCTGAGTTCG   AGGCCAGCCT   GGTCTACAAA   GTGAGTTCCA      3210

GGACAGCCAG   AGCTATACAG   AGAAACCCTG   TCTTGAAAAA   AAAAATTAAG   CAAAAGCTGA      3270

ATAAATAAAG   TTTTTTTTAT   GAC                                                    3293
```

( 2 ) INFORMATION FOR SEQ ID NO:2:

( i ) SEQUENCE CHARACTERISTICS:
        ( A ) LENGTH: 837 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Val   Gly   Leu   Gly   Ala   Cys   Thr   Leu   Thr   Gly   Val   Thr   Leu   Ile   Phe
 1                       5                          10                         15

Leu   Leu   Leu   Pro   Arg   Ser   Leu   Glu   Ser   Cys   Gly   His   Ile   Glu   Ile   Ser
                        20                          25                         30

Pro   Pro   Val   Val   Arg   Leu   Gly   Asp   Pro   Val   Leu   Ala   Ser   Cys   Thr   Ile
                  35                          40                         45

Ser   Pro   Asn   Cys   Ser   Lys   Leu   Asp   Gln   Gln   Ala   Lys   Ile   Leu   Trp   Arg
            50                          55                         60

Leu   Gln   Asp   Glu   Pro   Ile   Gln   Pro   Gly   Asp   Arg   Gln   His   His   Leu   Pro
 65                          70                         75                         80

Asp   Gly   Thr   Gln   Glu   Ser   Leu   Ile   Thr   Leu   Pro   His   Leu   Asn   Tyr   Thr
                        85                          90                         95

Gln   Ala   Phe   Leu   Phe   Cys   Leu   Val   Pro   Trp   Glu   Asp   Ser   Val   Gln   Leu
                  100                         105                        110

Leu   Asp   Gln   Ala   Glu   Leu   His   Ala   Gly   Tyr   Pro   Pro   Ala   Ser   Pro   Ser
            115                         120                        125

Asn   Leu   Ser   Cys   Leu   Met   His   Leu   Thr   Thr   Asn   Ser   Leu   Val   Cys   Gln
            130                         135                        140

Trp   Glu   Pro   Gly   Pro   Glu   Thr   His   Leu   Pro   Thr   Ser   Phe   Ile   Leu   Lys
145                         150                        155                        160

Ser   Phe   Arg   Ser   Arg   Ala   Asp   Cys   Gln   Tyr   Gln   Gly   Asp   Thr   Ile   Pro
                        165                         170                        175

Asp   Cys   Val   Ala   Lys   Lys   Arg   Gln   Asn   Asn   Cys   Ser   Ile   Pro   Arg   Lys
                  180                         185                        190

Asn   Leu   Leu   Leu   Tyr   Gln   Tyr   Met   Ala   Ile   Trp   Val   Gln   Ala   Glu   Asn
            195                         200                        205

Met   Leu   Gly   Ser   Ser   Glu   Ser   Pro   Lys   Leu   Cys   Leu   Asp   Pro   Met   Asp
            210                         215                        220

Val   Val   Lys   Leu   Glu   Pro   Pro   Met   Leu   Gln   Ala   Leu   Asp   Ile   Gly   Pro
225                         230                        235                        240

Asp   Val   Val   Ser   His   Gln   Pro   Gly   Cys   Leu   Trp   Leu   Ser   Trp   Lys   Pro
```

|     |     |     |     |     | 245 |     |     |     | 250 |     |     |     |     | 255 |     |
| --- | --- | --- | --- | --- | --- | --- | --- | --- | --- | --- | --- | --- | --- | --- | --- |
| Trp | Lys | Pro | Ser | Glu | Tyr | Met | Glu | Gln | Glu | Cys | Glu | Leu | Arg | Tyr | Gln |
|     |     |     | 260 |     |     |     |     | 265 |     |     |     | 270 |     |     |     |
| Pro | Gln | Leu | Lys | Gly | Ala | Asn | Trp | Thr | Leu | Val | Phe | His | Leu | Pro | Ser |
|     |     | 275 |     |     |     | 280 |     |     |     |     | 285 |     |     |     |     |
| Ser | Lys | Asp | Gln | Phe | Glu | Leu | Cys | Gly | Leu | His | Gln | Ala | Pro | Val | Tyr |
|     | 290 |     |     |     | 295 |     |     |     |     | 300 |     |     |     |     |     |
| Thr | Leu | Gln | Met | Arg | Cys | Ile | Arg | Ser | Ser | Leu | Pro | Gly | Phe | Trp | Ser |
| 305 |     |     |     |     | 310 |     |     |     |     | 315 |     |     |     |     | 320 |
| Pro | Trp | Ser | Pro | Gly | Leu | Gln | Leu | Arg | Pro | Thr | Met | Lys | Ala | Pro | Thr |
|     |     |     |     | 325 |     |     |     |     | 330 |     |     |     |     | 335 |     |
| Ile | Arg | Leu | Asp | Thr | Trp | Cys | Gln | Lys | Lys | Gln | Leu | Asp | Pro | Gly | Thr |
|     |     |     | 340 |     |     |     |     | 345 |     |     |     | 350 |     |     |     |
| Val | Ser | Val | Gln | Leu | Phe | Trp | Lys | Pro | Thr | Pro | Leu | Gln | Glu | Asp | Ser |
|     |     | 355 |     |     |     | 360 |     |     |     |     | 365 |     |     |     |     |
| Gly | Gln | Ile | Gln | Gly | Tyr | Leu | Leu | Ser | Trp | Asn | Ser | Pro | Asp | His | Gln |
|     | 370 |     |     |     | 375 |     |     |     |     | 380 |     |     |     |     |     |
| Gly | Gln | Asp | Ile | His | Leu | Cys | Asn | Thr | Thr | Gln | Leu | Ser | Cys | Ile | Phe |
| 385 |     |     |     |     | 390 |     |     |     |     | 395 |     |     |     |     | 400 |
| Leu | Leu | Pro | Ser | Glu | Ala | Gln | Asn | Val | Thr | Leu | Val | Ala | Tyr | Asn | Lys |
|     |     |     |     | 405 |     |     |     |     | 410 |     |     |     |     | 415 |     |
| Ala | Gly | Thr | Ser | Ser | Pro | Thr | Thr | Val | Val | Phe | Leu | Glu | Asn | Glu | Gly |
|     |     |     | 420 |     |     |     |     | 425 |     |     |     |     | 430 |     |     |
| Pro | Ala | Val | Thr | Gly | Leu | His | Ala | Met | Ala | Gln | Asp | Leu | Asn | Thr | Ile |
|     |     |     | 435 |     |     |     |     | 440 |     |     |     | 445 |     |     |     |
| Trp | Val | Asp | Trp | Glu | Ala | Pro | Ser | Leu | Leu | Pro | Gln | Gly | Tyr | Leu | Ile |
|     | 450 |     |     |     |     | 455 |     |     |     |     | 460 |     |     |     |     |
| Glu | Trp | Glu | Met | Ser | Ser | Pro | Ser | Tyr | Asn | Asn | Ser | Tyr | Lys | Ser | Trp |
| 465 |     |     |     |     | 470 |     |     |     |     | 475 |     |     |     |     | 480 |
| Met | Ile | Glu | Pro | Asn | Gly | Asn | Ile | Thr | Gly | Ile | Leu | Leu | Lys | Asp | Asn |
|     |     |     |     | 485 |     |     |     |     | 490 |     |     |     |     | 495 |     |
| Ile | Asn | Pro | Phe | Gln | Leu | Tyr | Arg | Ile | Thr | Val | Ala | Pro | Leu | Tyr | Pro |
|     |     |     | 500 |     |     |     |     | 505 |     |     |     | 510 |     |     |     |
| Gly | Ile | Val | Gly | Pro | Pro | Val | Asn | Val | Tyr | Thr | Phe | Ala | Gly | Glu | Arg |
|     |     |     | 515 |     |     |     |     | 520 |     |     |     |     | 525 |     |     |
| Ala | Pro | Pro | His | Ala | Pro | Ala | Leu | His | Leu | Lys | His | Val | Gly | Thr | Thr |
|     |     | 530 |     |     |     | 535 |     |     |     |     | 540 |     |     |     |     |
| Trp | Ala | Gln | Leu | Glu | Trp | Val | Pro | Glu | Ala | Pro | Arg | Leu | Gly | Met | Ile |
| 545 |     |     |     |     | 550 |     |     |     |     | 555 |     |     |     |     | 560 |
| Pro | Leu | Thr | His | Tyr | Thr | Ile | Phe | Trp | Ala | Asp | Ala | Gly | Asp | His | Ser |
|     |     |     |     | 565 |     |     |     |     | 570 |     |     |     |     | 575 |     |
| Phe | Ser | Val | Thr | Leu | Asn | Ile | Ser | Leu | His | Asp | Phe | Val | Leu | Lys | His |
|     |     |     | 580 |     |     |     |     | 585 |     |     |     |     | 590 |     |     |
| Leu | Glu | Pro | Ala | Ser | Leu | Tyr | His | Val | Tyr | Leu | Met | Ala | Thr | Ser | Arg |
|     |     | 595 |     |     |     |     | 600 |     |     |     |     | 605 |     |     |     |
| Ala | Gly | Ser | Thr | Asn | Ser | Thr | Gly | Leu | Thr | Leu | Arg | Thr | Leu | Asp | Pro |
|     | 610 |     |     |     |     | 615 |     |     |     |     | 620 |     |     |     |     |
| Ser | Asp | Leu | Asn | Ile | Phe | Leu | Gly | Ile | Leu | Cys | Leu | Val | Leu | Leu | Ser |
| 625 |     |     |     |     | 630 |     |     |     |     | 635 |     |     |     |     | 640 |
| Thr | Thr | Cys | Val | Val | Thr | Trp | Leu | Cys | Cys | Lys | Arg | Arg | Gly | Lys | Thr |
|     |     |     |     | 645 |     |     |     |     | 650 |     |     |     |     | 655 |     |
| Ser | Phe | Trp | Ser | Asp | Val | Pro | Asp | Pro | Ala | His | Ser | Ser | Leu | Ser | Ser |
|     |     |     | 660 |     |     |     |     | 665 |     |     |     | 670 |     |     |     |

| | | | | | | | | | | | | | | |
|---|---|---|---|---|---|---|---|---|---|---|---|---|---|---|
|Trp|Leu|Pro|Thr|Ile|Met|Thr|Glu|Glu|Thr|Phe|Gln|Leu|Pro|Ser|Phe|
| | |675| | | |680| | | |685| | | | |

| | | | | | | | | | | | | | | |
|---|---|---|---|---|---|---|---|---|---|---|---|---|---|---|
|Trp|Asp|Ser|Ser|Val|Pro|Ser|Ile|Thr|Lys|Ile|Thr|Glu|Leu|Glu|Glu|
| |690| | | |695| | | |700| | | | | |

| | | | | | | | | | | | | | | |
|---|---|---|---|---|---|---|---|---|---|---|---|---|---|---|
|Asp|Lys|Lys|Pro|Thr|His|Trp|Asp|Ser|Glu|Ser|Ser|Gly|Asn|Gly|Ser|
|705| | | | |710| | | |715| | | | | |720|

| | | | | | | | | | | | | | | |
|---|---|---|---|---|---|---|---|---|---|---|---|---|---|---|
|Leu|Pro|Ala|Leu|Val|Gln|Ala|Tyr|Val|Leu|Gln|Gly|Asp|Pro|Arg|Glu|
| | | | |725| | | |730| | | | |735| |

| | | | | | | | | | | | | | | |
|---|---|---|---|---|---|---|---|---|---|---|---|---|---|---|
|Ile|Ser|Asn|Gln|Ser|Gln|Pro|Pro|Ser|Arg|Thr|Gly|Asp|Gln|Val|Leu|
| | | |740| | | |745| | | | |750| | |

| | | | | | | | | | | | | | | |
|---|---|---|---|---|---|---|---|---|---|---|---|---|---|---|
|Tyr|Gly|Gln|Val|Leu|Glu|Ser|Pro|Thr|Ser|Pro|Gly|Val|Met|Gln|Tyr|
| | |755| | | |760| | | |765| | | | |

| | | | | | | | | | | | | | | |
|---|---|---|---|---|---|---|---|---|---|---|---|---|---|---|
|Ile|Arg|Ser|Asp|Ser|Thr|Gln|Pro|Leu|Leu|Gly|Gly|Pro|Thr|Pro|Ser|
| |770| | | | |775| | | |780| | | | |

| | | | | | | | | | | | | | | |
|---|---|---|---|---|---|---|---|---|---|---|---|---|---|---|
|Pro|Lys|Ser|Tyr|Glu|Asn|Ile|Trp|Phe|His|Ser|Arg|Pro|Gln|Glu|Thr|
|785| | | |790| | | |795| | | | | |800|

| | | | | | | | | | | | | | | |
|---|---|---|---|---|---|---|---|---|---|---|---|---|---|---|
|Phe|Val|Pro|Gln|Pro|Pro|Asn|Gln|Glu|Asp|Asp|Cys|Val|Phe|Gly|Pro|
| | | |805| | | |810| | | | |815| | |

| | | | | | | | | | | | | | | |
|---|---|---|---|---|---|---|---|---|---|---|---|---|---|---|
|Pro|Phe|Asp|Phe|Pro|Leu|Phe|Gln|Gly|Leu|Gln|Val|His|Gly|Val|Glu|
| | |820| | | |825| | | | |830| | | |

| | | | |
|---|---|---|---|
|Glu|Gln|Gly|Gly|Phe|
| | |835| |

(2) INFORMATION FOR SEQ ID NO:3:

(i) SEQUENCE CHARACTERISTICS:
        (A) LENGTH: 2943 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: CDS
        (B) LOCATION: 170..2677

(xi) SEQUENCE DESCRIPTION: SEQ ID NO:3:

```
GAAGCTGGAC TGCAGCTGGT TTCAGGAACT TCTCTTGACG AGAAGAGAGA CCAAGGAGGC      60

CAAGCAGGGG CTGGGCCAGA GGTGCCAACA TGGGGAAACT GAGGCTCGGC TCGGAAAGGT     120

GAAGTAACTT GTCCAAGATC ACAAAGCTGG TGAACATCAA GTTGGTGCT ATG GCA        175
                                                      Met Ala
                                                       1
```

| | | | | | | | | | | | | | | | | |
|---|---|---|---|---|---|---|---|---|---|---|---|---|---|---|---|---|
|AGG|CTG|GGA|AAC|TGC|AGC|CTG|ACT|TGG|GCT|GCC|CTG|ATC|ATC|CTG|CTG| |223|
|Arg|Leu|Gly|Asn|Cys|Ser|Leu|Thr|Trp|Ala|Ala|Leu|Ile|Ile|Leu|Leu| | |
| |5| | | | |10| | | | |15| | | | | | |

| | | | | | | | | | | | | | | | | |
|---|---|---|---|---|---|---|---|---|---|---|---|---|---|---|---|---|
|CTC|CCC|GGA|AGT|CTG|GAG|GAG|TGC|GGG|CAC|ATC|AGT|GTC|TCA|GCC|CCC| |271|
|Leu|Pro|Gly|Ser|Leu|Glu|Glu|Cys|Gly|His|Ile|Ser|Val|Ser|Ala|Pro| | |
| |20| | | | |25| | | | |30| | | | | | |

| | | | | | | | | | | | | | | | | |
|---|---|---|---|---|---|---|---|---|---|---|---|---|---|---|---|---|
|ATC|GTC|CAC|CTG|GGG|GAT|CCC|ATC|ACA|GCC|TCC|TGC|ATC|ATC|AAG|CAG| |319|
|Ile|Val|His|Leu|Gly|Asp|Pro|Ile|Thr|Ala|Ser|Cys|Ile|Ile|Lys|Gln| | |
|35| | | | |40| | | | |45| | | | |50| | |

| | | | | | | | | | | | | | | | | |
|---|---|---|---|---|---|---|---|---|---|---|---|---|---|---|---|---|
|AAC|TGC|AGC|CAT|CTG|GAC|CCG|GAG|CCA|CAG|ATT|CTG|TGG|AGA|CTG|GGA| |367|
|Asn|Cys|Ser|His|Leu|Asp|Pro|Glu|Pro|Gln|Ile|Leu|Trp|Arg|Leu|Gly| | |
| | | | |55| | | | |60| | | | |65| | | |

| | | | | | | | | | | | | | | | | |
|---|---|---|---|---|---|---|---|---|---|---|---|---|---|---|---|---|
|GCA|GAG|CTT|CAG|CCC|GGG|GGC|AGG|CAG|CAG|CGT|CTG|TCT|GAT|GGG|ACC| |415|
|Ala|Glu|Leu|Gln|Pro|Gly|Gly|Arg|Gln|Gln|Arg|Leu|Ser|Asp|Gly|Thr| | |
| | | |70| | | | |75| | | | |80| | | | |

| | | | | | | | | | | | | | | | | |
|---|---|---|---|---|---|---|---|---|---|---|---|---|---|---|---|---|
|CAG|GAA|TCT|ATC|ATC|ACC|CTG|CCC|CAC|CTC|AAC|CAC|ACT|CAG|GCC|TTT| |463|
|Gln|Glu|Ser|Ile|Ile|Thr|Leu|Pro|His|Leu|Asn|His|Thr|Gln|Ala|Phe| | |

```
                        85                           90                              95
CTC  TCC  TGC  TGC  CTG  AAC  TGG  GGC  AAC  AGC  CTG  CAG  ATC  CTG  GAC  CAG            511
Leu  Ser  Cys  Cys  Leu  Asn  Trp  Gly  Asn  Ser  Leu  Gln  Ile  Leu  Asp  Gln
     100                      105                      110

GTT  GAG  CTG  CGC  GCA  GGC  TAC  CCT  CCA  GCC  ATA  CCC  CAC  AAC  CTC  TCC            559
Val  Glu  Leu  Arg  Ala  Gly  Tyr  Pro  Pro  Ala  Ile  Pro  His  Asn  Leu  Ser
115                      120                      125                      130

TGC  CTC  ATG  AAC  CTC  ACA  ACC  AGC  AGC  CTC  ATC  TGC  CAG  TGG  GAG  CCA            607
Cys  Leu  Met  Asn  Leu  Thr  Thr  Ser  Ser  Leu  Ile  Cys  Gln  Trp  Glu  Pro
                    135                      140                      145

GGA  CCT  GAG  ACC  CAC  CTA  CCC  ACC  AGC  TTC  ACT  CTG  AAG  AGT  TTC  AAG            655
Gly  Pro  Glu  Thr  His  Leu  Pro  Thr  Ser  Phe  Thr  Leu  Lys  Ser  Phe  Lys
               150                      155                      160

AGC  CGG  GGC  AAC  TGT  CAG  ACC  CAA  GGG  GAC  TCC  ATC  CTG  GAC  TGC  GTG            703
Ser  Arg  Gly  Asn  Cys  Gln  Thr  Gln  Gly  Asp  Ser  Ile  Leu  Asp  Cys  Val
          165                      170                      175

CCC  AAG  GAC  GGG  CAG  AGC  CAC  TGC  TGC  ATC  CCA  CGC  AAA  CAC  CTG  CTG            751
Pro  Lys  Asp  Gly  Gln  Ser  His  Cys  Cys  Ile  Pro  Arg  Lys  His  Leu  Leu
     180                      185                      190

TTG  TAC  CAG  AAT  ATG  GGC  ATC  TGG  GTG  CAG  GCA  GAG  AAT  GCG  CTG  GGG            799
Leu  Tyr  Gln  Asn  Met  Gly  Ile  Trp  Val  Gln  Ala  Glu  Asn  Ala  Leu  Gly
195                      200                      205                      210

ACC  AGC  ATG  TCC  CCA  CAA  CTG  TGT  CTT  GAT  CCC  ATG  GAT  GTT  GTG  AAA            847
Thr  Ser  Met  Ser  Pro  Gln  Leu  Cys  Leu  Asp  Pro  Met  Asp  Val  Val  Lys
                    215                      220                      225

CTG  GAG  CCC  CCC  ATG  CTG  CGG  ACC  ATG  GAC  CCC  AGC  CCT  GAA  GCG  GCC            895
Leu  Glu  Pro  Pro  Met  Leu  Arg  Thr  Met  Asp  Pro  Ser  Pro  Glu  Ala  Ala
               230                      235                      240

CCT  CCC  CAG  GCA  GGC  TGC  CTA  CAG  CTG  TGC  TGG  GAG  CCA  TGG  CAG  CCA            943
Pro  Pro  Gln  Ala  Gly  Cys  Leu  Gln  Leu  Cys  Trp  Glu  Pro  Trp  Gln  Pro
          245                      250                      255

GGC  CTG  CAC  ATA  AAT  CAG  AAG  TGT  GAG  CTG  CGC  CAC  AAG  CCG  CAG  CGT            991
Gly  Leu  His  Ile  Asn  Gln  Lys  Cys  Glu  Leu  Arg  His  Lys  Pro  Gln  Arg
     260                      265                      270

GGA  GAA  GCC  AGC  TGG  GCA  CTG  GTG  GGC  CCC  CTC  CCC  TTG  GAG  GCC  CTT           1039
Gly  Glu  Ala  Ser  Trp  Ala  Leu  Val  Gly  Pro  Leu  Pro  Leu  Glu  Ala  Leu
275                      280                      285                      290

CAG  TAT  GAG  CTC  TGC  GGG  CTC  CTC  CCA  GCC  ACG  GCC  TAC  ACC  CTG  CAG           1087
Gln  Tyr  Glu  Leu  Cys  Gly  Leu  Leu  Pro  Ala  Thr  Ala  Tyr  Thr  Leu  Gln
                    295                      300                      305

ATA  CGC  TGC  ATC  CGC  TGG  CCC  CTG  CCT  GGC  CAC  TGG  AGC  GAC  TGG  AGC           1135
Ile  Arg  Cys  Ile  Arg  Trp  Pro  Leu  Pro  Gly  His  Trp  Ser  Asp  Trp  Ser
               310                      315                      320

CCC  AGC  CTG  GAG  CTG  AGA  ACT  ACC  GAA  CGG  GCC  CCC  ACT  GTC  AGA  CTG           1183
Pro  Ser  Leu  Glu  Leu  Arg  Thr  Thr  Glu  Arg  Ala  Pro  Thr  Val  Arg  Leu
          325                      330                      335

GAC  ACA  TGG  TGG  CGG  CAG  AGG  CAG  CTG  GAC  CCC  AGG  ACA  GTG  CAG  CTG           1231
Asp  Thr  Trp  Trp  Arg  Gln  Arg  Gln  Leu  Asp  Pro  Arg  Thr  Val  Gln  Leu
     340                      345                      350

TTC  TGG  AAG  CCA  GTG  CCC  CTG  GAG  GAA  GAC  AGC  GGA  CGG  ATC  CAA  GGT           1279
Phe  Trp  Lys  Pro  Val  Pro  Leu  Glu  Glu  Asp  Ser  Gly  Arg  Ile  Gln  Gly
355                      360                      365                      370

TAT  GTG  GTT  TCT  TGG  AGA  CCC  TCA  GGC  CAG  GCT  GGG  GCC  ATC  CTG  CCC           1327
Tyr  Val  Val  Ser  Trp  Arg  Pro  Ser  Gly  Gln  Ala  Gly  Ala  Ile  Leu  Pro
                    375                      380                      385

CTC  TGC  AAC  ACC  ACA  GAG  CTC  AGC  TGC  ACC  TTC  CAC  CTG  CCT  TCA  GAA           1375
Leu  Cys  Asn  Thr  Thr  Glu  Leu  Ser  Cys  Thr  Phe  His  Leu  Pro  Ser  Glu
               390                      395                      400

GCC  CAG  GAG  GTG  GCC  CTT  GTG  GCC  TAT  AAC  TCA  GCC  GGG  ACC  TCT  CGC           1423
Ala  Gln  Glu  Val  Ala  Leu  Val  Ala  Tyr  Asn  Ser  Ala  Gly  Thr  Ser  Arg
```

```
                  405                          410                                  415
CCC  ACC  CCG  GTG  GTC  TTC  TCA  GAA  AGC  AGA  GGC  CCA  GCT  CTG  ACC  AGA      1471
Pro  Thr  Pro  Val  Val  Phe  Ser  Glu  Ser  Arg  Gly  Pro  Ala  Leu  Thr  Arg
     420                      425                      430

CTC  CAT  GCC  ATG  GCC  CGA  GAC  CCT  CAC  AGC  CTC  TGG  GTA  GGC  TGG  GAG      1519
Leu  His  Ala  Met  Ala  Arg  Asp  Pro  His  Ser  Leu  Trp  Val  Gly  Trp  Glu
435                      440                      445                          450

CCC  CCC  AAT  CCA  TGG  CCT  CAG  GGC  TAT  GTG  ATT  GAG  TGG  GGC  CTG  GGC      1567
Pro  Pro  Asn  Pro  Trp  Pro  Gln  Gly  Tyr  Val  Ile  Glu  Trp  Gly  Leu  Gly
               455                      460                           465

CCC  CCC  AGC  GCG  AGC  AAT  AGC  AAC  AAG  ACC  TGG  AGG  ATG  GAA  CAG  AAT      1615
Pro  Pro  Ser  Ala  Ser  Asn  Ser  Asn  Lys  Thr  Trp  Arg  Met  Glu  Gln  Asn
          470                      475                      480

GGG  AGA  GCC  ACG  GGG  TTT  CTG  CTG  AAG  GAG  AAC  ATC  AGG  CCC  TTT  CAG      1663
Gly  Arg  Ala  Thr  Gly  Phe  Leu  Leu  Lys  Glu  Asn  Ile  Arg  Pro  Phe  Gln
          485                      490                      495

CTC  TAT  GAG  ATC  ATC  GTG  ACT  CCC  TTG  TAC  CAG  GAC  ACC  ATG  GGA  CCC      1711
Leu  Tyr  Glu  Ile  Ile  Val  Thr  Pro  Leu  Tyr  Gln  Asp  Thr  Met  Gly  Pro
          500                      505                      510

TCC  CAG  CAT  GTC  TAT  GCC  TAC  TCT  CAA  GAA  ATG  GCT  CCC  TCC  CAT  GCC      1759
Ser  Gln  His  Val  Tyr  Ala  Tyr  Ser  Gln  Glu  Met  Ala  Pro  Ser  His  Ala
515                      520                      525                          530

CCA  GAG  CTG  CAT  CTA  AAG  CAC  ATT  GGC  AAG  ACC  TGG  GCA  CAG  CTG  GAG      1807
Pro  Glu  Leu  His  Leu  Lys  His  Ile  Gly  Lys  Thr  Trp  Ala  Gln  Leu  Glu
               535                      540                      545

TGG  GTG  CCT  GAG  CCC  CCT  GAG  CTG  GGG  AAG  AGC  CCC  CTT  ACC  CAC  TAC      1855
Trp  Val  Pro  Glu  Pro  Pro  Glu  Leu  Gly  Lys  Ser  Pro  Leu  Thr  His  Tyr
          550                      555                      560

ACC  ATC  TTC  TGG  ACC  AAC  GCT  CAG  AAC  CAG  TCC  TTC  TCC  GCC  ATC  CTG      1903
Thr  Ile  Phe  Trp  Thr  Asn  Ala  Gln  Asn  Gln  Ser  Phe  Ser  Ala  Ile  Leu
          565                      570                      575

AAT  GCC  TCC  TCC  CGT  GGC  TTT  GTC  CTC  CAT  GGC  CTG  GAG  CCC  GCC  AGT      1951
Asn  Ala  Ser  Ser  Arg  Gly  Phe  Val  Leu  His  Gly  Leu  Glu  Pro  Ala  Ser
580                      585                      590

CTG  TAT  CAC  ATC  CAC  CTC  ATG  GCT  GCC  AGC  CAG  GCT  GGG  GCC  ACC  AAC      1999
Leu  Tyr  His  Ile  His  Leu  Met  Ala  Ala  Ser  Gln  Ala  Gly  Ala  Thr  Asn
595                      600                      605                          610

AGT  ACA  GTC  CTC  ACC  CTG  ATG  ACC  TTG  ACC  CCA  GAG  GGG  TCG  GAG  CTA      2047
Ser  Thr  Val  Leu  Thr  Leu  Met  Thr  Leu  Thr  Pro  Glu  Gly  Ser  Glu  Leu
               615                      620                      625

CAC  ATC  ATC  CTG  GGC  CTG  TTC  GGC  CTC  CTG  CTG  TTG  CTC  ACC  TGC  CTC      2095
His  Ile  Ile  Leu  Gly  Leu  Phe  Gly  Leu  Leu  Leu  Leu  Leu  Thr  Cys  Leu
               630                      635                      640

TGT  GGA  ACT  GCC  TGG  CTC  TGT  TGC  AGC  CCC  AAC  AGG  AAG  AAT  CCC  CTC      2143
Cys  Gly  Thr  Ala  Trp  Leu  Cys  Cys  Ser  Pro  Asn  Arg  Lys  Asn  Pro  Leu
          645                      650                      655

TGG  CCA  AGT  GTC  CCA  GAC  CCA  GCT  CAC  AGC  AGC  CTG  GGC  TCC  TGG  GTG      2191
Trp  Pro  Ser  Val  Pro  Asp  Pro  Ala  His  Ser  Ser  Leu  Gly  Ser  Trp  Val
660                      665                      670

CCC  ACA  ATC  ATG  GAG  GAG  GAT  GCC  TTC  CAG  CTG  CCC  GGC  CTT  GGC  ACG      2239
Pro  Thr  Ile  Met  Glu  Glu  Asp  Ala  Phe  Gln  Leu  Pro  Gly  Leu  Gly  Thr
675                      680                      685                          690

CCA  CCC  ATC  ACC  AAG  CTC  ACA  GTG  CTG  GAG  GAG  GAT  GAA  AAG  AAG  CCG      2287
Pro  Pro  Ile  Thr  Lys  Leu  Thr  Val  Leu  Glu  Glu  Asp  Glu  Lys  Lys  Pro
               695                      700                      705

GTG  CCC  TGG  GAG  TCC  CAT  AAC  AGC  TCA  GAG  ACC  TGT  GGC  CTC  CCC  ACT      2335
Val  Pro  Trp  Glu  Ser  His  Asn  Ser  Ser  Glu  Thr  Cys  Gly  Leu  Pro  Thr
          710                      715                      720

CTG  GTC  CAG  ACC  TAT  GTG  CTC  CAG  GGG  GAC  CCA  AGA  GCA  GTT  TCC  ACC      2383
Leu  Val  Gln  Thr  Tyr  Val  Leu  Gln  Gly  Asp  Pro  Arg  Ala  Val  Ser  Thr
```

|  |  |  |  |  |  |  |  |  |  |  |  |  |  |  |  |
|---|---|---|---|---|---|---|---|---|---|---|---|---|---|---|---|
|  |  |  | 725 |  |  |  | 730 |  |  |  | 735 |  |  |  |  |
| CAG | CCC | CAA | TCC | CAG | TCT | GGC | ACC | AGC | GAT | CAG | GTC | CTT | TAT | GGG | CAG | 2431 |
| Gln | Pro | Gln | Ser | Gln | Ser | Gly | Thr | Ser | Asp | Gln | Val | Leu | Tyr | Gly | Gln |  |
|  | 740 |  |  |  | 745 |  |  |  | 750 |  |  |  |  |  |  |
| CTG | CTG | GGC | AGC | CCC | ACA | AGC | CCA | GGG | CCA | GGG | CAC | TAT | CTC | CGC | TGT | 2479 |
| Leu | Leu | Gly | Ser | Pro | Thr | Ser | Pro | Gly | Pro | Gly | His | Tyr | Leu | Arg | Cys |  |
| 755 |  |  |  |  | 760 |  |  |  |  | 765 |  |  |  |  | 770 |  |
| GAC | TCC | ACT | CAG | CCC | CTC | TTG | GCG | GGC | CTC | ACC | CCC | AGC | CCC | AAG | TCC | 2527 |
| Asp | Ser | Thr | Gln | Pro | Leu | Leu | Ala | Gly | Leu | Thr | Pro | Ser | Pro | Lys | Ser |  |
|  |  |  |  | 775 |  |  |  |  | 780 |  |  |  |  | 785 |  |  |
| TAT | GAG | AAC | CTC | TGG | TTC | CAG | GCC | AGC | CCC | TTG | GGG | ACC | CTG | GTA | ACC | 2575 |
| Tyr | Glu | Asn | Leu | Trp | Phe | Gln | Ala | Ser | Pro | Leu | Gly | Thr | Leu | Val | Thr |  |
|  |  |  | 790 |  |  |  |  | 795 |  |  |  |  | 800 |  |  |  |
| CCA | GCC | CCA | AGC | CAG | GAG | GAC | GAC | TGT | GTC | TTT | GGG | CCA | CTG | CTC | AAC | 2623 |
| Pro | Ala | Pro | Ser | Gln | Glu | Asp | Asp | Cys | Val | Phe | Gly | Pro | Leu | Leu | Asn |  |
|  |  | 805 |  |  |  |  |  | 810 |  |  |  |  | 815 |  |  |  |
| TTC | CCC | CTC | CTG | CAG | GGG | ATC | CGG | GTC | CAT | GGG | ATG | GAG | GCG | CTG | GGG | 2671 |
| Phe | Pro | Leu | Leu | Gln | Gly | Ile | Arg | Val | His | Gly | Met | Glu | Ala | Leu | Gly |  |
|  | 820 |  |  |  |  | 825 |  |  |  |  | 830 |  |  |  |  |  |
| AGC | TTC | TAGGGCTTCC | | TGGGGTTCCC | | TTCTTGGGCC | | TGCCTCTTAA | | AGGCCTGAGC | | | | | | 2727 |
| Ser | Phe |  |  |  |  |  |  |  |  |  |  |  |  |  |  |  |
| 835 |  |  |  |  |  |  |  |  |  |  |  |  |  |  |  |  |

TAGCTGGAGA AGAGGGGAGG GTCCATAAGC CCATGACTAA AAACTACCCC AGCCCAGGCT     2787

CTCACCATCT CCAGTCACCA GCATCTCCCT CTCCTCCCAA TCTCCATAGG CTGGGCCTCC     2847

CAGGCGATCT GCATACTTTA AGGACCAGAT CATGCTCCAT CCAGCCCCAC CCAATGGCCT     2907

TTTGTGCTTG TTTCCTATAA CTTCAGTATT GTAAAC     2943

( 2 ) INFORMATION FOR SEQ ID NO:4:

( i ) SEQUENCE CHARACTERISTICS:
        ( A ) LENGTH: 836 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Arg | Leu | Gly | Asn | Cys | Ser | Leu | Thr | Trp | Ala | Ala | Leu | Ile | Ile |
|---|---|---|---|---|---|---|---|---|---|---|---|---|---|---|---|
| 1 |  |  |  | 5 |  |  |  |  | 10 |  |  |  |  | 15 |  |
| Leu | Leu | Leu | Pro | Gly | Ser | Leu | Glu | Glu | Cys | Gly | His | Ile | Ser | Val | Ser |
|  |  |  | 20 |  |  |  |  | 25 |  |  |  |  | 30 |  |  |
| Ala | Pro | Ile | Val | His | Leu | Gly | Asp | Pro | Ile | Thr | Ala | Ser | Cys | Ile | Ile |
|  |  | 35 |  |  |  |  | 40 |  |  |  |  | 45 |  |  |  |
| Lys | Gln | Asn | Cys | Ser | His | Leu | Asp | Pro | Glu | Pro | Gln | Ile | Leu | Trp | Arg |
|  | 50 |  |  |  |  | 55 |  |  |  |  | 60 |  |  |  |  |
| Leu | Gly | Ala | Glu | Leu | Gln | Pro | Gly | Gly | Arg | Gln | Gln | Arg | Leu | Ser | Asp |
| 65 |  |  |  |  | 70 |  |  |  |  | 75 |  |  |  |  | 80 |
| Gly | Thr | Gln | Glu | Ser | Ile | Ile | Thr | Leu | Pro | His | Leu | Asn | His | Thr | Gln |
|  |  |  |  | 85 |  |  |  |  | 90 |  |  |  |  | 95 |  |
| Ala | Phe | Leu | Ser | Cys | Cys | Leu | Asn | Trp | Gly | Asn | Ser | Leu | Gln | Ile | Leu |
|  |  |  | 100 |  |  |  |  | 105 |  |  |  |  | 110 |  |  |
| Asp | Gln | Val | Glu | Leu | Arg | Ala | Gly | Tyr | Pro | Pro | Ala | Ile | Pro | His | Asn |
|  |  | 115 |  |  |  |  | 120 |  |  |  |  | 125 |  |  |  |
| Leu | Ser | Cys | Leu | Met | Asn | Leu | Thr | Thr | Ser | Ser | Leu | Ile | Cys | Gln | Trp |
|  | 130 |  |  |  |  | 135 |  |  |  |  | 140 |  |  |  |  |
| Glu | Pro | Gly | Pro | Glu | Thr | His | Leu | Pro | Thr | Ser | Phe | Thr | Leu | Lys | Ser |
| 145 |  |  |  |  | 150 |  |  |  |  | 155 |  |  |  |  | 160 |

```
Phe Lys Ser Arg Gly Asn Cys Gln Thr Gln Gly Asp Ser Ile Leu Asp
            165                 170                 175
Cys Val Pro Lys Asp Gly Gln Ser His Cys Cys Ile Pro Arg Lys His
            180                 185                 190
Leu Leu Leu Tyr Gln Asn Met Gly Ile Trp Val Gln Ala Glu Asn Ala
            195                 200                 205
Leu Gly Thr Ser Met Ser Pro Gln Leu Cys Leu Asp Pro Met Asp Val
            210                 215                 220
Val Lys Leu Glu Pro Pro Met Leu Arg Thr Met Asp Pro Ser Pro Glu
225                 230                 235                 240
Ala Ala Pro Pro Gln Ala Gly Cys Leu Gln Leu Cys Trp Glu Pro Trp
            245                 250                 255
Gln Pro Gly Leu His Ile Asn Gln Lys Cys Glu Leu Arg His Lys Pro
            260                 265                 270
Gln Arg Gly Glu Ala Ser Trp Ala Leu Val Gly Pro Leu Pro Leu Glu
            275                 280                 285
Ala Leu Gln Tyr Glu Leu Cys Gly Leu Leu Pro Ala Thr Ala Tyr Thr
            290                 295                 300
Leu Gln Ile Arg Cys Ile Arg Trp Pro Leu Pro Gly His Trp Ser Asp
305                 310                 315                 320
Trp Ser Pro Ser Leu Glu Leu Arg Thr Thr Glu Arg Ala Pro Thr Val
            325                 330                 335
Arg Leu Asp Thr Trp Trp Arg Gln Arg Gln Leu Asp Pro Arg Thr Val
            340                 345                 350
Gln Leu Phe Trp Lys Pro Val Pro Leu Glu Glu Asp Ser Gly Arg Ile
            355                 360                 365
Gln Gly Tyr Val Val Ser Trp Arg Pro Ser Gly Gln Ala Gly Ala Ile
            370                 375                 380
Leu Pro Leu Cys Asn Thr Thr Glu Leu Ser Cys Thr Phe His Leu Pro
385                 390                 395                 400
Ser Glu Ala Gln Glu Val Ala Leu Val Ala Tyr Asn Ser Ala Gly Thr
            405                 410                 415
Ser Arg Pro Thr Pro Val Val Phe Ser Glu Ser Arg Gly Pro Ala Leu
            420                 425                 430
Thr Arg Leu His Ala Met Ala Arg Asp Pro His Ser Leu Trp Val Gly
            435                 440                 445
Trp Glu Pro Pro Asn Pro Trp Pro Gln Gly Tyr Val Ile Glu Trp Gly
            450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
            485                 490                 495
Phe Gln Leu Tyr Glu Ile Ile Val Thr Pro Leu Tyr Gln Asp Thr Met
            500                 505                 510
Gly Pro Ser Gln His Val Tyr Ala Tyr Ser Gln Glu Met Ala Pro Ser
            515                 520                 525
His Ala Pro Glu Leu His Leu Lys His Ile Gly Lys Thr Trp Ala Gln
            530                 535                 540
Leu Glu Trp Val Pro Glu Pro Pro Glu Leu Gly Lys Ser Pro Leu Thr
545                 550                 555                 560
His Tyr Thr Ile Phe Trp Thr Asn Ala Gln Asn Gln Ser Phe Ser Ala
            565                 570                 575
Ile Leu Asn Ala Ser Ser Arg Gly Phe Val Leu His Gly Leu Glu Pro
            580                 585                 590
```

| | | | | | | | | | | | | | | |
|---|---|---|---|---|---|---|---|---|---|---|---|---|---|---|
| Ala | Ser | Leu<br>595 | Tyr | His | Ile | His | Leu<br>600 | Met | Ala | Ala | Ser<br>605 | Gln | Ala | Gly | Ala |
| Thr | Asn<br>610 | Ser | Thr | Val | Leu<br>615 | Leu | Met | Thr | Leu<br>620 | Thr | Pro | Glu | Gly | Ser |
| Glu<br>625 | Leu | His | Ile | Ile | Leu<br>630 | Gly | Leu | Phe | Gly | Leu<br>635 | Leu | Leu | Leu | Thr<br>640 |
| Cys | Leu | Cys | Gly | Thr<br>645 | Ala | Trp | Leu | Cys | Cys<br>650 | Ser | Pro | Asn | Arg | Lys<br>655 | Asn |
| Pro | Leu | Trp | Pro<br>660 | Ser | Val | Pro | Asp | Pro<br>665 | Ala | His | Ser | Ser<br>670 | Leu | Gly | Ser |
| Trp | Val | Pro<br>675 | Thr | Ile | Met | Glu | Glu<br>680 | Asp | Ala | Phe | Gln<br>685 | Leu | Pro | Gly | Leu |
| Gly | Thr<br>690 | Pro | Pro | Ile | Thr | Lys<br>695 | Leu | Thr | Val | Leu | Glu<br>700 | Glu | Asp | Glu | Lys |
| Lys<br>705 | Pro | Val | Pro | Trp | Glu<br>710 | Ser | His | Asn | Ser | Ser<br>715 | Glu | Thr | Cys | Gly | Leu<br>720 |
| Pro | Thr | Leu | Val | Gln<br>725 | Thr | Tyr | Val | Leu | Gln<br>730 | Gly | Asp | Pro | Arg | Ala<br>735 | Val |
| Ser | Thr | Gln | Pro<br>740 | Gln | Ser | Gln | Ser | Gly<br>745 | Thr | Ser | Asp | Gln | Val<br>750 | Leu | Tyr |
| Gly | Gln | Leu<br>755 | Leu | Gly | Ser | Pro | Thr<br>760 | Ser | Pro | Gly | Pro | Gly<br>765 | His | Tyr | Leu |
| Arg | Cys<br>770 | Asp | Ser | Thr | Gln | Pro<br>775 | Leu | Leu | Ala | Gly | Leu<br>780 | Thr | Pro | Ser | Pro |
| Lys<br>785 | Ser | Tyr | Glu | Asn | Leu<br>790 | Trp | Phe | Gln | Ala | Ser<br>795 | Pro | Leu | Gly | Thr | Leu<br>800 |
| Val | Thr | Pro | Ala | Pro<br>805 | Ser | Gln | Glu | Asp | Asp<br>810 | Cys | Val | Phe | Gly | Pro<br>815 | Leu |
| Leu | Asn | Phe | Pro<br>820 | Leu | Leu | Gln | Gly | Ile<br>825 | Arg | Val | His | Gly | Met<br>830 | Glu | Ala |
| Leu | Gly | Ser<br>835 | Phe | | | | | | | | | | | |

( 2 ) INFORMATION FOR SEQ ID NO:5:

( i ) SEQUENCE CHARACTERISTICS:
        ( A ) LENGTH: 2855 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION: 170..2482

( x i ) SEQUENCE DESCRIPTION: SEQ ID NO:5:

```
GAAGCTGGAC  TGCAGCTGGT  TTCAGGAACT  TCTCTTGACG  AGAAGAGAGA  CCAAGGAGGC         60

CAAGCAGGGG  CTGGGCCAGA  GGTGCCAACA  TGGGGAAACT  GAGGCTCGGC  TCGGAAAGGT        120

GAAGTAACTT  GTCCAAGATC  ACAAAGCTGG  TGAACATCAA  GTTGGTGCT ATG GCA             175
                                                        Met Ala
                                                          1

AGG CTG GGA AAC TGC AGC CTG ACT TGG GCT GCC CTG ATC ATC CTG CTG             223
Arg Leu Gly Asn Cys Ser Leu Thr Trp Ala Ala Leu Ile Ile Leu Leu
        5                   10                  15

CTC CCC GGA AGT CTG GAG GAG TGC GGG CAC ATC AGT GTC TCA GCC CCC             271
Leu Pro Gly Ser Leu Glu Glu Cys Gly His Ile Ser Val Ser Ala Pro
```

-continued

| | | | | | | | | | | | | | | | | |
|---|---|---|---|---|---|---|---|---|---|---|---|---|---|---|---|---|
| | | | 20 | | | | | 25 | | | | | 30 | | | |
| ATC | GTC | CAC | CTG | GGG | GAT | CCC | ATC | ACA | GCC | TCC | TGC | ATC | ATC | AAG | CAG | 319 |
| Ile | Val | His | Leu | Gly | Asp | Pro | Ile | Thr | Ala | Ser | Cys | Ile | Ile | Lys | Gln | |
| 35 | | | | 40 | | | | | 45 | | | | | 50 | | |
| AAC | TGC | AGC | CAT | CTG | GAC | CCG | GAG | CCA | CAG | ATT | CTG | TGG | AGA | CTG | GGA | 367 |
| Asn | Cys | Ser | His | Leu | Asp | Pro | Glu | Pro | Gln | Ile | Leu | Trp | Arg | Leu | Gly | |
| | | | | 55 | | | | | 60 | | | | | 65 | | |
| GCA | GAG | CTT | CAG | CCC | GGG | GGC | AGG | CAG | CAG | CGT | CTG | TCT | GAT | GGG | ACC | 415 |
| Ala | Glu | Leu | Gln | Pro | Gly | Gly | Arg | Gln | Gln | Arg | Leu | Ser | Asp | Gly | Thr | |
| | | | 70 | | | | | 75 | | | | | 80 | | | |
| CAG | GAA | TCT | ATC | ATC | ACC | CTG | CCC | CAC | CTC | AAC | CAC | ACT | CAG | GCC | TTT | 463 |
| Gln | Glu | Ser | Ile | Ile | Thr | Leu | Pro | His | Leu | Asn | His | Thr | Gln | Ala | Phe | |
| | | 85 | | | | | 90 | | | | | 95 | | | | |
| CTC | TCC | TGC | TGC | CTG | AAC | TGG | GGC | AAC | AGC | CTG | CAG | ATC | CTG | GAC | CAG | 511 |
| Leu | Ser | Cys | Cys | Leu | Asn | Trp | Gly | Asn | Ser | Leu | Gln | Ile | Leu | Asp | Gln | |
| | | 100 | | | | | 105 | | | | | 110 | | | | |
| GTT | GAG | CTG | CGC | GCA | GGC | TAC | CCT | CCA | GCC | ATA | CCC | CAC | AAC | CTC | TCC | 559 |
| Val | Glu | Leu | Arg | Ala | Gly | Tyr | Pro | Pro | Ala | Ile | Pro | His | Asn | Leu | Ser | |
| 115 | | | | | 120 | | | | | 125 | | | | | 130 | |
| TGC | CTC | ATG | AAC | CTC | ACA | ACC | AGC | AGC | CTC | ATC | TGC | CAG | TGG | GAG | CCA | 607 |
| Cys | Leu | Met | Asn | Leu | Thr | Thr | Ser | Ser | Leu | Ile | Cys | Gln | Trp | Glu | Pro | |
| | | | | 135 | | | | | 140 | | | | | 145 | | |
| GGA | CCT | GAG | ACC | CAC | CTA | CCC | ACC | AGC | TTC | ACT | CTG | AAG | AGT | TTC | AAG | 655 |
| Gly | Pro | Glu | Thr | His | Leu | Pro | Thr | Ser | Phe | Thr | Leu | Lys | Ser | Phe | Lys | |
| | | | | 150 | | | | | 155 | | | | | 160 | | |
| AGC | CGG | GGC | AAC | TGT | CAG | ACC | CAA | GGG | GAC | TCC | ATC | CTG | GAC | TGC | GTG | 703 |
| Ser | Arg | Gly | Asn | Cys | Gln | Thr | Gln | Gly | Asp | Ser | Ile | Leu | Asp | Cys | Val | |
| | | 165 | | | | | 170 | | | | | 175 | | | | |
| CCC | AAG | GAC | GGG | CAG | AGC | CAC | TGC | TGC | ATC | CCA | CGC | AAA | CAC | CTG | CTG | 751 |
| Pro | Lys | Asp | Gly | Gln | Ser | His | Cys | Cys | Ile | Pro | Arg | Lys | His | Leu | Leu | |
| | 180 | | | | | 185 | | | | | 190 | | | | | |
| TTG | TAC | CAG | AAT | ATG | GGC | ATC | TGG | GTG | CAG | GCA | GAG | AAT | GCG | CTG | GGG | 799 |
| Leu | Tyr | Gln | Asn | Met | Gly | Ile | Trp | Val | Gln | Ala | Glu | Asn | Ala | Leu | Gly | |
| 195 | | | | | 200 | | | | | 205 | | | | | 210 | |
| ACC | AGC | ATG | TCC | CCA | CAA | CTG | TGT | CTT | GAT | CCC | ATG | GAT | GTT | GTG | AAA | 847 |
| Thr | Ser | Met | Ser | Pro | Gln | Leu | Cys | Leu | Asp | Pro | Met | Asp | Val | Val | Lys | |
| | | | | 215 | | | | | 220 | | | | | 225 | | |
| CTG | GAG | CCC | CCC | ATG | CTG | CGG | ACC | ATG | GAC | CCC | AGC | CCT | GAA | GCG | GCC | 895 |
| Leu | Glu | Pro | Pro | Met | Leu | Arg | Thr | Met | Asp | Pro | Ser | Pro | Glu | Ala | Ala | |
| | | | | 230 | | | | | 235 | | | | | 240 | | |
| CCT | CCC | CAG | GCA | GGC | TGC | CTA | CAG | CTG | TGC | TGG | GAG | CCA | TGG | CAG | CCA | 943 |
| Pro | Pro | Gln | Ala | Gly | Cys | Leu | Gln | Leu | Cys | Trp | Glu | Pro | Trp | Gln | Pro | |
| | | 245 | | | | | 250 | | | | | 255 | | | | |
| GGC | CTG | CAC | ATA | AAT | CAG | AAG | TGT | GAG | CTG | CGC | CAC | AAG | CCG | CAG | CGT | 991 |
| Gly | Leu | His | Ile | Asn | Gln | Lys | Cys | Glu | Leu | Arg | His | Lys | Pro | Gln | Arg | |
| | | 260 | | | | | 265 | | | | | 270 | | | | |
| GGA | GAA | GCC | AGC | TGG | GCA | CTG | GTG | GGC | CCC | CTC | CCC | TTG | GAG | GCC | CTT | 1039 |
| Gly | Glu | Ala | Ser | Trp | Ala | Leu | Val | Gly | Pro | Leu | Pro | Leu | Glu | Ala | Leu | |
| 275 | | | | | 280 | | | | | 285 | | | | | 290 | |
| CAG | TAT | GAG | CTC | TGC | GGG | CTC | CTC | CCA | GCC | ACG | GCC | TAC | ACC | CTG | CAG | 1087 |
| Gln | Tyr | Glu | Leu | Cys | Gly | Leu | Leu | Pro | Ala | Thr | Ala | Tyr | Thr | Leu | Gln | |
| | | | | 295 | | | | | 300 | | | | | 305 | | |
| ATA | CGC | TGC | ATC | CGC | TGG | CCC | CTG | CCT | GGC | CAC | TGG | AGC | GAC | TGG | AGC | 1135 |
| Ile | Arg | Cys | Ile | Arg | Trp | Pro | Leu | Pro | Gly | His | Trp | Ser | Asp | Trp | Ser | |
| | | 310 | | | | | 315 | | | | | 320 | | | | |
| CCC | AGC | CTG | GAG | CTG | AGA | ACT | ACC | GAA | CGG | GCC | CCC | ACT | GTC | AGA | CTG | 1183 |
| Pro | Ser | Leu | Glu | Leu | Arg | Thr | Thr | Glu | Arg | Ala | Pro | Thr | Val | Arg | Leu | |
| | | 325 | | | | | 330 | | | | | 335 | | | | |
| GAC | ACA | TGG | TGG | CGG | CAG | AGG | CAG | CTG | GAC | CCC | AGG | ACA | GTG | CAG | CTG | 1231 |
| Asp | Thr | Trp | Trp | Arg | Gln | Arg | Gln | Leu | Asp | Pro | Arg | Thr | Val | Gln | Leu | |

```
         340                          345                         350
TTC  TGG  AAG  CCA  GTG  CCC  CTG  GAG  GAA  GAC  AGC  GGA  CGG  ATC  CAA  GGT    1279
Phe  Trp  Lys  Pro  Val  Pro  Leu  Glu  Glu  Asp  Ser  Gly  Arg  Ile  Gln  Gly
355                      360                      365                      370

TAT  GTG  GTT  TCT  TGG  AGA  CCC  TCA  GGC  CAG  GCT  GGG  GCC  ATC  CTG  CCC    1327
Tyr  Val  Val  Ser  Trp  Arg  Pro  Ser  Gly  Gln  Ala  Gly  Ala  Ile  Leu  Pro
                         375                      380                      385

CTC  TGC  AAC  ACC  ACA  GAG  CTC  AGC  TGC  ACC  TTC  CAC  CTG  CCT  TCA  GAA    1375
Leu  Cys  Asn  Thr  Thr  Glu  Leu  Ser  Cys  Thr  Phe  His  Leu  Pro  Ser  Glu
               390                      395                      400

GCC  CAG  GAG  GTG  GCC  CTT  GTG  GCC  TAT  AAC  TCA  GCC  GGG  ACC  TCT  CGC    1423
Ala  Gln  Glu  Val  Ala  Leu  Val  Ala  Tyr  Asn  Ser  Ala  Gly  Thr  Ser  Arg
          405                      410                      415

CCC  ACC  CCG  GTG  GTC  TTC  TCA  GAA  AGC  AGA  GGC  CCA  GCT  CTG  ACC  AGA    1471
Pro  Thr  Pro  Val  Val  Phe  Ser  Glu  Ser  Arg  Gly  Pro  Ala  Leu  Thr  Arg
     420                      425                      430

CTC  CAT  GCC  ATG  GCC  CGA  GAC  CCT  CAC  AGC  CTC  TGG  GTA  GGC  TGG  GAG    1519
Leu  His  Ala  Met  Ala  Arg  Asp  Pro  His  Ser  Leu  Trp  Val  Gly  Trp  Glu
435                      440                      445                      450

CCC  CCC  AAT  CCA  TGG  CCT  CAG  GGC  TAT  GTG  ATT  GAG  TGG  GGC  CTG  GGC    1567
Pro  Pro  Asn  Pro  Trp  Pro  Gln  Gly  Tyr  Val  Ile  Glu  Trp  Gly  Leu  Gly
                    455                      460                      465

CCC  CCC  AGC  GCG  AGC  AAT  AGC  AAC  AAG  ACC  TGG  AGG  ATG  GAA  CAG  AAT    1615
Pro  Pro  Ser  Ala  Ser  Asn  Ser  Asn  Lys  Thr  Trp  Arg  Met  Glu  Gln  Asn
               470                      475                      480

GGG  AGA  GCC  ACG  GGG  TTT  CTG  CTG  AAG  GAG  AAC  ATC  AGG  CCC  TTT  CAG    1663
Gly  Arg  Ala  Thr  Gly  Phe  Leu  Leu  Lys  Glu  Asn  Ile  Arg  Pro  Phe  Gln
          485                      490                      495

CTC  TAT  GAG  ATC  ATC  GTG  ACT  CCC  TTG  TAC  CAG  GAC  ACC  ATG  GGA  CCC    1711
Leu  Tyr  Glu  Ile  Ile  Val  Thr  Pro  Leu  Tyr  Gln  Asp  Thr  Met  Gly  Pro
     500                      505                      510

TCC  CAG  CAT  GTC  TAT  GCC  TAC  TCT  CAA  GAA  ATG  GCT  CCC  TCC  CAT  GCC    1759
Ser  Gln  His  Val  Tyr  Ala  Tyr  Ser  Gln  Glu  Met  Ala  Pro  Ser  His  Ala
515                      520                      525                      530

CCA  GAG  CTG  CAT  CTA  AAG  CAC  ATT  GGC  AAG  ACC  TGG  GCA  CAG  CTG  GAG    1807
Pro  Glu  Leu  His  Leu  Lys  His  Ile  Gly  Lys  Thr  Trp  Ala  Gln  Leu  Glu
                    535                      540                      545

TGG  GTG  CCT  GAG  CCC  CCT  GAG  CTG  GGG  AAG  AGC  CCC  CTT  ACC  CAC  TAC    1855
Trp  Val  Pro  Glu  Pro  Pro  Glu  Leu  Gly  Lys  Ser  Pro  Leu  Thr  His  Tyr
               550                      555                      560

ACC  ATC  TTC  TGG  ACC  AAC  GCT  CAG  AAC  CAG  TCC  TTC  TCC  GCC  ATC  CTG    1903
Thr  Ile  Phe  Trp  Thr  Asn  Ala  Gln  Asn  Gln  Ser  Phe  Ser  Ala  Ile  Leu
          565                      570                      575

AAT  GCC  TCC  TCC  CGT  GGC  TTT  GTC  CTC  CAT  GGC  CTG  GAG  CCC  GCC  AGT    1951
Asn  Ala  Ser  Ser  Arg  Gly  Phe  Val  Leu  His  Gly  Leu  Glu  Pro  Ala  Ser
580                      585                      590

CTG  TAT  CAC  ATC  CAC  CTC  ATG  GCT  GCC  AGC  CAG  GCT  GGG  GCC  ACC  AAC    1999
Leu  Tyr  His  Ile  His  Leu  Met  Ala  Ala  Ser  Gln  Ala  Gly  Ala  Thr  Asn
595                      600                      605                      610

AGT  ACA  GTC  CTC  ACC  CTG  ATG  ACC  TTG  ACC  CCA  GCC  CCA  ACA  GGA  AGA    2047
Ser  Thr  Val  Leu  Thr  Leu  Met  Thr  Leu  Thr  Pro  Ala  Pro  Thr  Gly  Arg
               615                      620                      625

ATC  CCC  TCT  GGC  CAA  GTG  TCC  CAG  ACC  CAG  CTC  ACA  GCA  GCC  TGG  GCT    2095
Ile  Pro  Ser  Gly  Gln  Val  Ser  Gln  Thr  Gln  Leu  Thr  Ala  Ala  Trp  Ala
          630                      635                      640

CCT  GGG  TGC  CCA  CAA  TCA  TGG  AGG  AGG  ATG  CCT  TCC  AGC  TGC  CCG  GCC    2143
Pro  Gly  Cys  Pro  Gln  Ser  Trp  Arg  Arg  Met  Pro  Ser  Ser  Cys  Pro  Ala
     645                      650                      655

TTG  GCA  CGC  CAC  CCA  TCA  CCA  AGC  TCA  CAG  TGC  TGG  AGG  AGG  ATG  AAA    2191
Leu  Ala  Arg  His  Pro  Ser  Pro  Ser  Ser  Gln  Cys  Trp  Arg  Arg  Met  Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 660 |     |     |     |     | 665 |     |     |     |     | 670 |      |
| AGA | AGC | CGG | TGC | CCT | GGG | AGT | CCC | ATA | ACA | GCT | CAG | AGA | CCT | GTG | GCC | 2239 |
| Arg | Ser | Arg | Cys | Pro | Gly | Ser | Pro | Ile | Thr | Ala | Gln | Arg | Pro | Val | Ala |      |
| 675 |     |     |     |     | 680 |     |     |     |     | 685 |     |     |     |     | 690 |      |
| TCC | CCA | CTC | TGG | TCC | AGA | CCT | ATG | TGC | TCC | AGG | GGG | ACC | CAA | GAG | CAG | 2287 |
| Ser | Pro | Leu | Trp | Ser | Arg | Pro | Met | Cys | Ser | Arg | Gly | Thr | Gln | Glu | Gln |      |
|     |     |     |     | 695 |     |     |     |     | 700 |     |     |     |     | 705 |     |      |
| TTT | CCA | CCC | AGC | CCC | AAT | CCC | AGT | CTG | GCA | CCA | GCG | ATC | AGG | TCC | TTT | 2335 |
| Phe | Pro | Pro | Ser | Pro | Asn | Pro | Ser | Leu | Ala | Pro | Ala | Ile | Arg | Ser | Phe |      |
|     |     |     | 710 |     |     |     |     | 715 |     |     |     |     | 720 |     |     |      |
| ATG | GGC | AGC | TGC | TGG | GCA | GCC | CCA | CAA | GCC | CAG | GGC | CAG | GGC | ACT | ATC | 2383 |
| Met | Gly | Ser | Cys | Trp | Ala | Ala | Pro | Gln | Ala | Gln | Gly | Gln | Gly | Thr | Ile |      |
|     |     | 725 |     |     |     |     | 730 |     |     |     |     | 735 |     |     |     |      |
| TCC | GCT | GTG | ACT | CCA | CTC | AGC | CCC | TCT | TGG | CGG | GCC | TCA | CCC | CCA | GCC | 2431 |
| Ser | Ala | Val | Thr | Pro | Leu | Ser | Pro | Ser | Trp | Arg | Ala | Ser | Pro | Pro | Ala |      |
|     | 740 |     |     |     |     | 745 |     |     |     |     | 750 |     |     |     |     |      |
| CCA | AGT | CCT | ATG | AGA | ACC | TCT | GGT | TCC | AGG | CCA | GCC | CCT | TGG | GGA | CCC | 2479 |
| Pro | Ser | Pro | Met | Arg | Thr | Ser | Gly | Ser | Arg | Pro | Ala | Pro | Trp | Gly | Pro |      |
| 755 |     |     |     |     | 760 |     |     |     |     | 765 |     |     |     |     | 770 |      |

| | |
|---|---|
| TGG | 2532 |
| Trp | |
| AACCCCAGC CCCAAGCCAG GAGGACGACT GTGTCTTTGG GCCACTGCTC | |
| AACTTCCCCC TCCTGCAGGG GATCCGGGTC CATGGGATGG AGGCGCTGGG GAGCTTCTAG | 2592 |
| GGCTTCCTGG GGTTCCCTTC TTGGGCCTGC CTCTTAAAGG CCTGAGCTAG CTGGAGAAGA | 2652 |
| GGGGAGGGTC CATAAGCCCA TGACTAAAAA CTACCCCAGC CCAGGCTCTC ACCATCTCCA | 2712 |
| GTCACCAGCA TCTCCCTCTC CTCCCAATCT CCATAGGCTG GGCCTCCCAG GCGATCTGCA | 2772 |
| TACTTTAAGG ACCAGATCAT GCTCCATCCA GCCCCACCCA ATGGCCTTTT GTGCTTGTTT | 2832 |
| CCTATAACTT CAGTATTGTA AAC | 2855 |

( 2 ) INFORMATION FOR SEQ ID NO:6:

( i ) SEQUENCE CHARACTERISTICS:
        ( A ) LENGTH: 771 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Ala | Arg | Leu | Gly | Asn | Cys | Ser | Leu | Thr | Trp | Ala | Ala | Leu | Ile | Ile |
| 1 | | | | 5 | | | | | 10 | | | | | 15 | |
| Leu | Leu | Leu | Pro | Gly | Ser | Leu | Glu | Glu | Cys | Gly | His | Ile | Ser | Val | Ser |
| | | | 20 | | | | | 25 | | | | | 30 | | |
| Ala | Pro | Ile | Val | His | Leu | Gly | Asp | Pro | Ile | Thr | Ala | Ser | Cys | Ile | Ile |
| | | | 35 | | | | 40 | | | | | 45 | | | |
| Lys | Gln | Asn | Cys | Ser | His | Leu | Asp | Pro | Glu | Pro | Gln | Ile | Leu | Trp | Arg |
| | 50 | | | | | 55 | | | | | 60 | | | | |
| Leu | Gly | Ala | Glu | Leu | Gln | Pro | Gly | Gly | Arg | Gln | Gln | Arg | Leu | Ser | Asp |
| 65 | | | | | 70 | | | | | 75 | | | | | 80 |
| Gly | Thr | Gln | Glu | Ser | Ile | Ile | Thr | Leu | Pro | His | Leu | Asn | His | Thr | Gln |
| | | | | 85 | | | | | 90 | | | | | 95 | |
| Ala | Phe | Leu | Ser | Cys | Cys | Leu | Asn | Trp | Gly | Asn | Ser | Leu | Gln | Ile | Leu |
| | | | | 100 | | | | | 105 | | | | | 110 | |
| Asp | Gln | Val | Glu | Leu | Arg | Ala | Gly | Tyr | Pro | Pro | Ala | Ile | Pro | His | Asn |
| | | | 115 | | | | | 120 | | | | | 125 | | |
| Leu | Ser | Cys | Leu | Met | Asn | Leu | Thr | Thr | Ser | Ser | Leu | Ile | Cys | Gln | Trp |
| | 130 | | | | | 135 | | | | | 140 | | | | |

| | | | | | | | | | | | | | | | |
|---|---|---|---|---|---|---|---|---|---|---|---|---|---|---|---|
| Glu | Pro | Gly | Pro | Glu | Thr | His | Leu | Pro | Thr | Ser | Phe | Thr | Leu | Lys | Ser |
| 145 | | | | | 150 | | | | | 155 | | | | | 160 |
| Phe | Lys | Ser | Arg | Gly | Asn | Cys | Gln | Thr | Gln | Gly | Asp | Ser | Ile | Leu | Asp |
| | | | | 165 | | | | | 170 | | | | | 175 | |
| Cys | Val | Pro | Lys | Asp | Gly | Gln | Ser | His | Cys | Cys | Ile | Pro | Arg | Lys | His |
| | | | 180 | | | | | 185 | | | | | 190 | | |
| Leu | Leu | Leu | Tyr | Gln | Asn | Met | Gly | Ile | Trp | Val | Gln | Ala | Glu | Asn | Ala |
| | | | 195 | | | | 200 | | | | | 205 | | | |
| Leu | Gly | Thr | Ser | Met | Ser | Pro | Gln | Leu | Cys | Leu | Asp | Pro | Met | Asp | Val |
| | 210 | | | | | 215 | | | | | 220 | | | | |
| Val | Lys | Leu | Glu | Pro | Pro | Met | Leu | Arg | Thr | Met | Asp | Pro | Ser | Pro | Glu |
| 225 | | | | | 230 | | | | | 235 | | | | | 240 |
| Ala | Ala | Pro | Pro | Gln | Ala | Gly | Cys | Leu | Gln | Leu | Cys | Trp | Glu | Pro | Trp |
| | | | | 245 | | | | | 250 | | | | | 255 | |
| Gln | Pro | Gly | Leu | His | Ile | Asn | Gln | Lys | Cys | Glu | Leu | Arg | His | Lys | Pro |
| | | | | 260 | | | | | 265 | | | | | 270 | |
| Gln | Arg | Gly | Glu | Ala | Ser | Trp | Ala | Leu | Val | Gly | Pro | Leu | Pro | Leu | Glu |
| | | | 275 | | | | 280 | | | | | 285 | | | |
| Ala | Leu | Gln | Tyr | Glu | Leu | Cys | Gly | Leu | Leu | Pro | Ala | Thr | Ala | Tyr | Thr |
| | 290 | | | | | 295 | | | | | 300 | | | | |
| Leu | Gln | Ile | Arg | Cys | Ile | Arg | Trp | Pro | Leu | Pro | Gly | His | Trp | Ser | Asp |
| 305 | | | | | 310 | | | | | 315 | | | | | 320 |
| Trp | Ser | Pro | Ser | Leu | Glu | Leu | Arg | Thr | Thr | Glu | Arg | Ala | Pro | Thr | Val |
| | | | | 325 | | | | | 330 | | | | | 335 | |
| Arg | Leu | Asp | Thr | Trp | Trp | Arg | Gln | Arg | Gln | Leu | Asp | Pro | Arg | Thr | Val |
| | | | 340 | | | | | 345 | | | | | 350 | | |
| Gln | Leu | Phe | Trp | Lys | Pro | Val | Pro | Leu | Glu | Glu | Asp | Ser | Gly | Arg | Ile |
| | | 355 | | | | | 360 | | | | | 365 | | | |
| Gln | Gly | Tyr | Val | Val | Ser | Trp | Arg | Pro | Ser | Gly | Gln | Ala | Gly | Ala | Ile |
| | 370 | | | | | 375 | | | | | 380 | | | | |
| Leu | Pro | Leu | Cys | Asn | Thr | Thr | Glu | Leu | Ser | Cys | Thr | Phe | His | Leu | Pro |
| 385 | | | | | 390 | | | | | 395 | | | | | 400 |
| Ser | Glu | Ala | Gln | Glu | Val | Ala | Leu | Val | Ala | Tyr | Asn | Ser | Ala | Gly | Thr |
| | | | | 405 | | | | | 410 | | | | | 415 | |
| Ser | Arg | Pro | Thr | Pro | Val | Val | Phe | Ser | Glu | Ser | Arg | Gly | Pro | Ala | Leu |
| | | | 420 | | | | | 425 | | | | | 430 | | |
| Thr | Arg | Leu | His | Ala | Met | Ala | Arg | Asp | Pro | His | Ser | Leu | Trp | Val | Gly |
| | | 435 | | | | | 440 | | | | | 445 | | | |
| Trp | Glu | Pro | Pro | Asn | Pro | Trp | Pro | Gln | Gly | Tyr | Val | Ile | Glu | Trp | Gly |
| | 450 | | | | | 455 | | | | | 460 | | | | |
| Leu | Gly | Pro | Pro | Ser | Ala | Ser | Asn | Ser | Asn | Lys | Thr | Trp | Arg | Met | Glu |
| 465 | | | | | 470 | | | | | 475 | | | | | 480 |
| Gln | Asn | Gly | Arg | Ala | Thr | Gly | Phe | Leu | Leu | Lys | Glu | Asn | Ile | Arg | Pro |
| | | | | 485 | | | | | 490 | | | | | 495 | |
| Phe | Gln | Leu | Tyr | Glu | Ile | Ile | Val | Thr | Pro | Leu | Tyr | Gln | Asp | Thr | Met |
| | | | 500 | | | | | 505 | | | | | 510 | | |
| Gly | Pro | Ser | Gln | His | Val | Tyr | Ala | Tyr | Ser | Gln | Glu | Met | Ala | Pro | Ser |
| | | 515 | | | | | 520 | | | | | 525 | | | |
| His | Ala | Pro | Glu | Leu | His | Leu | Lys | His | Ile | Gly | Lys | Thr | Trp | Ala | Gln |
| | 530 | | | | | 535 | | | | | 540 | | | | |
| Leu | Glu | Trp | Val | Pro | Glu | Pro | Pro | Glu | Leu | Gly | Lys | Ser | Pro | Leu | Thr |
| 545 | | | | | 550 | | | | | 555 | | | | | 560 |
| His | Tyr | Thr | Ile | Phe | Trp | Thr | Asn | Ala | Gln | Asn | Gln | Ser | Phe | Ser | Ala |
| | | | | 565 | | | | | 570 | | | | | 575 | |

| Ile | Leu | Asn | Ala | Ser | Ser | Arg | Gly | Phe | Val | Leu | His | Gly | Leu | Glu | Pro |
|---|---|---|---|---|---|---|---|---|---|---|---|---|---|---|---|
| | | | 580 | | | | | 585 | | | | | 590 | | |

| Ala | Ser | Leu | Tyr | His | Ile | His | Leu | Met | Ala | Ala | Ser | Gln | Ala | Gly | Ala |
|---|---|---|---|---|---|---|---|---|---|---|---|---|---|---|---|
| | | | 595 | | | | 600 | | | | | 605 | | | |

| Thr | Asn | Ser | Thr | Val | Leu | Thr | Leu | Met | Thr | Leu | Thr | Pro | Ala | Pro | Thr |
|---|---|---|---|---|---|---|---|---|---|---|---|---|---|---|---|
| | | 610 | | | | | 615 | | | | | 620 | | | |

| Gly | Arg | Ile | Pro | Ser | Gly | Gln | Val | Ser | Gln | Thr | Gln | Leu | Thr | Ala | Ala |
|---|---|---|---|---|---|---|---|---|---|---|---|---|---|---|---|
| 625 | | | | | 630 | | | | | 635 | | | | | 640 |

| Trp | Ala | Pro | Gly | Cys | Pro | Gln | Ser | Trp | Arg | Arg | Met | Pro | Ser | Ser | Cys |
|---|---|---|---|---|---|---|---|---|---|---|---|---|---|---|---|
| | | | | 645 | | | | | 650 | | | | | 655 | |

| Pro | Ala | Leu | Ala | Arg | His | Pro | Ser | Pro | Ser | Ser | Gln | Cys | Trp | Arg | Arg |
|---|---|---|---|---|---|---|---|---|---|---|---|---|---|---|---|
| | | | | 660 | | | | | 665 | | | | | 670 | |

| Met | Lys | Arg | Ser | Arg | Cys | Pro | Gly | Ser | Pro | Ile | Thr | Ala | Gln | Arg | Pro |
|---|---|---|---|---|---|---|---|---|---|---|---|---|---|---|---|
| | | 675 | | | | | 680 | | | | | 685 | | | |

| Val | Ala | Ser | Pro | Leu | Trp | Ser | Arg | Pro | Met | Cys | Ser | Arg | Gly | Thr | Gln |
|---|---|---|---|---|---|---|---|---|---|---|---|---|---|---|---|
| | 690 | | | | | 695 | | | | | 700 | | | | |

| Glu | Gln | Phe | Pro | Pro | Ser | Pro | Asn | Pro | Ser | Leu | Ala | Pro | Ala | Ile | Arg |
|---|---|---|---|---|---|---|---|---|---|---|---|---|---|---|---|
| 705 | | | | | 710 | | | | | 715 | | | | | 720 |

| Ser | Phe | Met | Gly | Ser | Cys | Trp | Ala | Ala | Pro | Gln | Ala | Gln | Gly | Gln | Gly |
|---|---|---|---|---|---|---|---|---|---|---|---|---|---|---|---|
| | | | | 725 | | | | | 730 | | | | | 735 | |

| Thr | Ile | Ser | Ala | Val | Thr | Pro | Leu | Ser | Pro | Ser | Trp | Arg | Ala | Ser | Pro |
|---|---|---|---|---|---|---|---|---|---|---|---|---|---|---|---|
| | | | 740 | | | | | 745 | | | | | 750 | | |

| Pro | Ala | Pro | Ser | Pro | Met | Arg | Thr | Ser | Gly | Ser | Arg | Pro | Ala | Pro | Trp |
|---|---|---|---|---|---|---|---|---|---|---|---|---|---|---|---|
| | | 755 | | | | | 760 | | | | | 765 | | | |

| Gly | Pro | Trp |
|---|---|---|
| | 770 | |

( 2 ) INFORMATION FOR SEQ ID NO:7:

( i ) SEQUENCE CHARACTERISTICS:
        ( A ) LENGTH: 3024 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION: 170..2758

( x i ) SEQUENCE DESCRIPTION: SEQ ID NO:7:

```
GAAGCTGGAC TGCAGCTGGT TTCAGGAACT TCTCTTGACG AGAAGAGAGA CCAAGGAGGC      60

CAAGCAGGGG CTGGGCCAGA GGTGCCAACA TGGGGAAACT GAGGCTCGGC TCGGAAAGGT     120

GAAGTAACTT GTCCAAGATC ACAAAGCTGG TGAACATCAA GTTGGTGCT ATG GCA        175
                                                       Met Ala
                                                         1
```

| AGG | CTG | GGA | AAC | TGC | AGC | CTG | ACT | TGG | GCT | GCC | CTG | ATC | ATC | CTG | CTG | 223 |
|---|---|---|---|---|---|---|---|---|---|---|---|---|---|---|---|---|
| Arg | Leu | Gly | Asn | Cys | Ser | Leu | Thr | Trp | Ala | Ala | Leu | Ile | Ile | Leu | Leu | |
| | | | 5 | | | | | 10 | | | | | 15 | | | |

| CTC | CCC | GGA | AGT | CTG | GAG | GAG | TGC | GGG | CAC | ATC | AGT | GTC | TCA | GCC | CCC | 271 |
|---|---|---|---|---|---|---|---|---|---|---|---|---|---|---|---|---|
| Leu | Pro | Gly | Ser | Leu | Glu | Glu | Cys | Gly | His | Ile | Ser | Val | Ser | Ala | Pro | |
| | 20 | | | | | 25 | | | | | 30 | | | | | |

| ATC | GTC | CAC | CTG | GGG | GAT | CCC | ATC | ACA | GCC | TCC | TGC | ATC | ATC | AAG | CAG | 319 |
|---|---|---|---|---|---|---|---|---|---|---|---|---|---|---|---|---|
| Ile | Val | His | Leu | Gly | Asp | Pro | Ile | Thr | Ala | Ser | Cys | Ile | Ile | Lys | Gln | |
| 35 | | | | | 40 | | | | | 45 | | | | | 50 | |

| AAC | TGC | AGC | CAT | CTG | GAC | CCG | GAG | CCA | CAG | ATT | CTG | TGG | AGA | CTG | GGA | 367 |
|---|---|---|---|---|---|---|---|---|---|---|---|---|---|---|---|---|
| Asn | Cys | Ser | His | Leu | Asp | Pro | Glu | Pro | Gln | Ile | Leu | Trp | Arg | Leu | Gly | |
| | | | 55 | | | | | 60 | | | | | 65 | | | |

| | | | | | | | | | | | | | | | | |
|---|---|---|---|---|---|---|---|---|---|---|---|---|---|---|---|---|
| GCA | GAG | CTT | CAG | CCC | GGG | GGC | AGG | CAG | CAG | CGT | CTG | TCT | GAT | GGG | ACC | 415 |
| Ala | Glu | Leu | Gln | Pro | Gly | Gly | Arg | Gln | Gln | Arg | Leu | Ser | Asp | Gly | Thr | |
| | | | 70 | | | | | 75 | | | | | 80 | | | |
| CAG | GAA | TCT | ATC | ATC | ACC | CTG | CCC | CAC | CTC | AAC | CAC | ACT | CAG | GCC | TTT | 463 |
| Gln | Glu | Ser | Ile | Ile | Thr | Leu | Pro | His | Leu | Asn | His | Thr | Gln | Ala | Phe | |
| | | 85 | | | | | 90 | | | | | 95 | | | | |
| CTC | TCC | TGC | TGC | CTG | AAC | TGG | GGC | AAC | AGC | CTG | CAG | ATC | CTG | GAC | CAG | 511 |
| Leu | Ser | Cys | Cys | Leu | Asn | Trp | Gly | Asn | Ser | Leu | Gln | Ile | Leu | Asp | Gln | |
| | | 100 | | | | | 105 | | | | | 110 | | | | |
| GTT | GAG | CTG | CGC | GCA | GGC | TAC | CCT | CCA | GCC | ATA | CCC | CAC | AAC | CTC | TCC | 559 |
| Val | Glu | Leu | Arg | Ala | Gly | Tyr | Pro | Pro | Ala | Ile | Pro | His | Asn | Leu | Ser | |
| 115 | | | | | 120 | | | | | 125 | | | | | 130 | |
| TGC | CTC | ATG | AAC | CTC | ACA | ACC | AGC | AGC | CTC | ATC | TGC | CAG | TGG | GAG | CCA | 607 |
| Cys | Leu | Met | Asn | Leu | Thr | Thr | Ser | Ser | Leu | Ile | Cys | Gln | Trp | Glu | Pro | |
| | | | | 135 | | | | | 140 | | | | | 145 | | |
| GGA | CCT | GAG | ACC | CAC | CTA | CCC | ACC | AGC | TTC | ACT | CTG | AAG | AGT | TTC | AAG | 655 |
| Gly | Pro | Glu | Thr | His | Leu | Pro | Thr | Ser | Phe | Thr | Leu | Lys | Ser | Phe | Lys | |
| | | | 150 | | | | | 155 | | | | | 160 | | | |
| AGC | CGG | GGC | AAC | TGT | CAG | ACC | CAA | GGG | GAC | TCC | ATC | CTG | GAC | TGC | GTG | 703 |
| Ser | Arg | Gly | Asn | Cys | Gln | Thr | Gln | Gly | Asp | Ser | Ile | Leu | Asp | Cys | Val | |
| | | 165 | | | | | 170 | | | | | 175 | | | | |
| CCC | AAG | GAC | GGG | CAG | AGC | CAC | TGC | TGC | ATC | CCA | CGC | AAA | CAC | CTG | CTG | 751 |
| Pro | Lys | Asp | Gly | Gln | Ser | His | Cys | Cys | Ile | Pro | Arg | Lys | His | Leu | Leu | |
| | 180 | | | | | 185 | | | | | 190 | | | | | |
| TTG | TAC | CAG | AAT | ATG | GGC | ATC | TGG | GTG | CAG | GCA | GAG | AAT | GCG | CTG | GGG | 799 |
| Leu | Tyr | Gln | Asn | Met | Gly | Ile | Trp | Val | Gln | Ala | Glu | Asn | Ala | Leu | Gly | |
| 195 | | | | | 200 | | | | | 205 | | | | | 210 | |
| ACC | AGC | ATG | TCC | CCA | CAA | CTG | TGT | CTT | GAT | CCC | ATG | GAT | GTT | GTG | AAA | 847 |
| Thr | Ser | Met | Ser | Pro | Gln | Leu | Cys | Leu | Asp | Pro | Met | Asp | Val | Val | Lys | |
| | | | | 215 | | | | | 220 | | | | | 225 | | |
| CTG | GAG | CCC | CCC | ATG | CTG | CGG | ACC | ATG | GAC | CCC | AGC | CCT | GAA | GCG | GCC | 895 |
| Leu | Glu | Pro | Pro | Met | Leu | Arg | Thr | Met | Asp | Pro | Ser | Pro | Glu | Ala | Ala | |
| | | | | 230 | | | | | 235 | | | | | 240 | | |
| CCT | CCC | CAG | GCA | GGC | TGC | CTA | CAG | CTG | TGC | TGG | GAG | CCA | TGG | CAG | CCA | 943 |
| Pro | Pro | Gln | Ala | Gly | Cys | Leu | Gln | Leu | Cys | Trp | Glu | Pro | Trp | Gln | Pro | |
| | | | 245 | | | | | 250 | | | | | 255 | | | |
| GGC | CTG | CAC | ATA | AAT | CAG | AAG | TGT | GAG | CTG | CGC | CAC | AAG | CCG | CAG | CGT | 991 |
| Gly | Leu | His | Ile | Asn | Gln | Lys | Cys | Glu | Leu | Arg | His | Lys | Pro | Gln | Arg | |
| 260 | | | | | 265 | | | | | 270 | | | | | | |
| GGA | GAA | GCC | AGC | TGG | GCA | CTG | GTG | GGC | CCC | CTC | CCC | TTG | GAG | GCC | CTT | 1039 |
| Gly | Glu | Ala | Ser | Trp | Ala | Leu | Val | Gly | Pro | Leu | Pro | Leu | Glu | Ala | Leu | |
| 275 | | | | | 280 | | | | | 285 | | | | | 290 | |
| CAG | TAT | GAG | CTC | TGC | GGG | CTC | CTC | CCA | GCC | ACG | GCC | TAC | ACC | CTG | CAG | 1087 |
| Gln | Tyr | Glu | Leu | Cys | Gly | Leu | Leu | Pro | Ala | Thr | Ala | Tyr | Thr | Leu | Gln | |
| | | | | 295 | | | | | 300 | | | | | 305 | | |
| ATA | CGC | TGC | ATC | CGC | TGG | CCC | CTG | CCT | GGC | CAC | TGG | AGC | GAC | TGG | AGC | 1135 |
| Ile | Arg | Cys | Ile | Arg | Trp | Pro | Leu | Pro | Gly | His | Trp | Ser | Asp | Trp | Ser | |
| | | | 310 | | | | | 315 | | | | | 320 | | | |
| CCC | AGC | CTG | GAG | CTG | AGA | ACT | ACC | GAA | CGG | GCC | CCC | ACT | GTC | AGA | CTG | 1183 |
| Pro | Ser | Leu | Glu | Leu | Arg | Thr | Thr | Glu | Arg | Ala | Pro | Thr | Val | Arg | Leu | |
| | | 325 | | | | | 330 | | | | | 335 | | | | |
| GAC | ACA | TGG | TGG | CGG | CAG | AGG | CAG | CTG | GAC | CCC | AGG | ACA | GTG | CAG | CTG | 1231 |
| Asp | Thr | Trp | Trp | Arg | Gln | Arg | Gln | Leu | Asp | Pro | Arg | Thr | Val | Gln | Leu | |
| 340 | | | | | 345 | | | | | 350 | | | | | | |
| TTC | TGG | AAG | CCA | GTG | CCC | CTG | GAG | GAA | GAC | AGC | GGA | CGG | ATC | CAA | GGT | 1279 |
| Phe | Trp | Lys | Pro | Val | Pro | Leu | Glu | Glu | Asp | Ser | Gly | Arg | Ile | Gln | Gly | |
| 355 | | | | | 360 | | | | | 365 | | | | | 370 | |
| TAT | GTG | GTT | TCT | TGG | AGA | CCC | TCA | GGC | CAG | GCT | GGG | GCC | ATC | CTG | CCC | 1327 |
| Tyr | Val | Val | Ser | Trp | Arg | Pro | Ser | Gly | Gln | Ala | Gly | Ala | Ile | Leu | Pro | |
| | | | 375 | | | | | 380 | | | | | 385 | | | |

| | | | | | | | | | | | | | | | | |
|---|---|---|---|---|---|---|---|---|---|---|---|---|---|---|---|---|
| CTC | TGC | AAC | ACC | ACA | GAG | CTC | AGC | TGC | ACC | TTC | CAC | CTG | CCT | TCA | GAA | 1375 |
| Leu | Cys | Asn | Thr 390 | Thr | Glu | Leu | Ser | Cys 395 | Thr | Phe | His | Leu | Pro 400 | Ser | Glu | |
| GCC | CAG | GAG | GTG | GCC | CTT | GTG | GCC | TAT | AAC | TCA | GCC | GGG | ACC | TCT | CGC | 1423 |
| Ala | Gln | Glu 405 | Val | Ala | Leu | Val | Ala | Tyr 410 | Asn | Ser | Ala | Gly | Thr 415 | Ser | Arg | |
| CCC | ACC | CCG | GTG | GTC | TTC | TCA | GAA | AGC | AGA | GGC | CCA | GCT | CTG | ACC | AGA | 1471 |
| Pro | Thr 420 | Pro | Val | Val | Phe | Ser | Glu 425 | Ser | Arg | Gly | Pro | Ala 430 | Leu | Thr | Arg | |
| CTC | CAT | GCC | ATG | GCC | CGA | GAC | CCT | CAC | AGC | CTC | TGG | GTA | GGC | TGG | GAG | 1519 |
| Leu 435 | His | Ala | Met | Ala | Arg 440 | Asp | Pro | His | Ser | Leu 445 | Trp | Val | Gly | Trp | Glu 450 | |
| CCC | CCC | AAT | CCA | TGG | CCT | CAG | GGC | TAT | GTG | ATT | GAG | TGG | GGC | CTG | GGC | 1567 |
| Pro | Pro | Asn | Pro | Trp 455 | Pro | Gln | Gly | Tyr | Val 460 | Ile | Glu | Trp | Gly | Leu 465 | Gly | |
| CCC | CCC | AGC | GCG | AGC | AAT | AGC | AAC | AAG | ACC | TGG | AGG | ATG | GAA | CAG | AAT | 1615 |
| Pro | Pro | Ser | Ala 470 | Ser | Asn | Ser | Asn | Lys 475 | Thr | Trp | Arg | Met | Glu 480 | Gln | Asn | |
| GGG | AGA | GCC | ACG | GGG | TTT | CTG | CTG | AAG | GAG | AAC | ATC | AGG | CCC | TTT | CAG | 1663 |
| Gly | Arg | Ala 485 | Thr | Gly | Phe | Leu | Leu 490 | Lys | Glu | Asn | Ile | Arg 495 | Pro | Phe | Gln | |
| CTC | TAT | GAG | ATC | ATC | GTG | ACT | CCC | TTG | TAC | CAG | GAC | ACC | ATG | GGA | CCC | 1711 |
| Leu | Tyr 500 | Glu | Ile | Ile | Val | Thr 505 | Pro | Leu | Tyr | Gln | Asp 510 | Thr | Met | Gly | Pro | |
| TCC | CAG | CAT | GTC | TAT | GCC | TAC | TCT | CAA | GAA | ATG | GCT | CCC | TCC | CAT | GCC | 1759 |
| Ser 515 | Gln | His | Val | Tyr | Ala 520 | Tyr | Ser | Gln | Glu | Met 525 | Ala | Pro | Ser | His | Ala 530 | |
| CCA | GAG | CTG | CAT | CTA | AAG | CAC | ATT | GGC | AAG | ACC | TGG | GCA | CAG | CTG | GAG | 1807 |
| Pro | Glu | Leu | His | Leu 535 | Lys | His | Ile | Gly | Lys 540 | Thr | Trp | Ala | Gln | Leu 545 | Glu | |
| TGG | GTG | CCT | GAG | CCC | CCT | GAG | CTG | GGG | AAG | AGC | CCC | CTT | ACC | CAC | TAC | 1855 |
| Trp | Val | Pro | Glu 550 | Pro | Pro | Glu | Leu | Gly 555 | Lys | Ser | Pro | Leu | Thr 560 | His | Tyr | |
| ACC | ATC | TTC | TGG | ACC | AAC | GCT | CAG | AAC | CAG | TCC | TTC | TCC | GCC | ATC | CTG | 1903 |
| Thr | Ile | Phe | Trp 565 | Thr | Asn | Ala | Gln | Asn 570 | Gln | Ser | Phe | Ser 575 | Ala | Ile | Leu | |
| AAT | GCC | TCC | TCC | CGT | GGC | TTT | GTC | CTC | CAT | GGC | CTG | GAG | CCC | GCC | AGT | 1951 |
| Asn | Ala | Ser 580 | Ser | Arg | Gly | Phe | Val 585 | Leu | His | Gly | Leu | Glu 590 | Pro | Ala | Ser | |
| CTG | TAT | CAC | ATC | CAC | CTC | ATG | GCT | GCC | AGC | CAG | GCT | GGG | GCC | ACC | AAC | 1999 |
| Leu 595 | Tyr | His | Ile | His | Leu 600 | Met | Ala | Ala | Ser | Gln 605 | Ala | Gly | Ala | Thr | Asn 610 | |
| AGT | ACA | GTC | CTC | ACC | CTG | ATG | ACC | TTG | ACC | CCA | GAG | GGG | TCG | GAG | CTA | 2047 |
| Ser | Thr | Val | Leu | Thr 615 | Leu | Met | Thr | Leu | Thr 620 | Pro | Glu | Gly | Ser | Glu 625 | Leu | |
| CAC | ATC | ATC | CTG | GGC | CTG | TTC | GGC | CTC | CTG | TTG | CTC | ACC | TGC | CTC | | 2095 |
| His | Ile | Ile | Leu 630 | Gly | Leu | Phe | Gly | Leu 635 | Leu | Leu | Leu | Thr 640 | Cys | Leu | | |
| TGT | GGA | ACT | GCC | TGG | CTC | TGT | TGC | AGC | CCC | AAC | AGG | AAG | AAT | CCC | CTC | 2143 |
| Cys | Gly | Thr | Ala 645 | Trp | Leu | Cys | Cys | Ser 650 | Pro | Asn | Arg | Lys | Asn 655 | Pro | Leu | |
| TGG | CCA | AGT | GTC | CCA | GAC | CCA | GCT | CAC | AGC | AGC | CTG | GGC | TCC | TGG | GTG | 2191 |
| Trp | Pro | Ser 660 | Val | Pro | Asp | Pro | Ala 665 | His | Ser | Ser | Leu | Gly 670 | Ser | Trp | Val | |
| CCC | ACA | ATC | ATG | GAG | GAG | CTG | CCC | GGA | CCC | AGA | CAG | GGA | CAG | TGG | CTG | 2239 |
| Pro | Thr | Ile 675 | Met | Glu | Glu | Leu | Pro 680 | Gly | Pro | Arg | Gln | Gly 685 | Gln | Trp | Leu 690 | |
| GGG | CAG | ACA | TCT | GAA | ATG | AGC | CGT | GCT | CTC | ACC | CCA | CAT | CCT | TGT | GTG | 2287 |
| Gly | Gln | Thr | Ser | Glu 695 | Met | Ser | Arg | Ala | Leu 700 | Thr | Pro | His | Pro | Cys 705 | Val | |

| | | | | | | | | | | | | | | | | |
|---|---|---|---|---|---|---|---|---|---|---|---|---|---|---|---|---|
| CAG | GAT | GCC | TTC | CAG | CTG | CCC | GGC | CTT | GGC | ACG | CCA | CCC | ATC | ACC | AAG | 2335 |
| Gln | Asp | Ala | Phe | Gln | Leu | Pro | Gly | Leu | Gly | Thr | Pro | Pro | Ile | Thr | Lys | |
| | | | 710 | | | | | 715 | | | | | 720 | | | |
| CTC | ACA | GTG | CTG | GAG | GAG | GAT | GAA | AAG | AAG | CCG | GTG | CCC | TGG | GAG | TCC | 2383 |
| Leu | Thr | Val | Leu | Glu | Glu | Asp | Glu | Lys | Lys | Pro | Val | Pro | Trp | Glu | Ser | |
| | | 725 | | | | | 730 | | | | | 735 | | | | |
| CAT | AAC | AGC | TCA | GAG | ACC | TGT | GGC | CTC | CCC | ACT | CTG | GTC | CAG | ACC | TAT | 2431 |
| His | Asn | Ser | Ser | Glu | Thr | Cys | Gly | Leu | Pro | Thr | Leu | Val | Gln | Thr | Tyr | |
| | 740 | | | | | 745 | | | | | 750 | | | | | |
| GTG | CTC | CAG | GGG | GAC | CCA | AGA | GCA | GTT | TCC | ACC | CAG | CCC | CAA | TCC | CAG | 2479 |
| Val | Leu | Gln | Gly | Asp | Pro | Arg | Ala | Val | Ser | Thr | Gln | Pro | Gln | Ser | Gln | |
| 755 | | | | | 760 | | | | | 765 | | | | | 770 | |
| TCT | GGC | ACC | AGC | GAT | CAG | GTC | CTT | TAT | GGG | CAG | CTG | CTG | GGC | AGC | CCC | 2527 |
| Ser | Gly | Thr | Ser | Asp | Gln | Val | Leu | Tyr | Gly | Gln | Leu | Leu | Gly | Ser | Pro | |
| | | | | 775 | | | | | 780 | | | | | 785 | | |
| ACA | AGC | CCA | GGG | CCA | GGG | CAC | TAT | CTC | CGC | TGT | GAC | TCC | ACT | CAG | CCC | 2575 |
| Thr | Ser | Pro | Gly | Pro | Gly | His | Tyr | Leu | Arg | Cys | Asp | Ser | Thr | Gln | Pro | |
| | | | 790 | | | | | 795 | | | | | 800 | | | |
| CTC | TTG | GCG | GGC | CTC | ACC | CCC | AGC | CCC | AAG | TCC | TAT | GAG | AAC | CTC | TGG | 2623 |
| Leu | Leu | Ala | Gly | Leu | Thr | Pro | Ser | Pro | Lys | Ser | Tyr | Glu | Asn | Leu | Trp | |
| | | | 805 | | | | | 810 | | | | | 815 | | | |
| TTC | CAG | GCC | AGC | CCC | TTG | GGG | ACC | CTG | GTA | ACC | CCA | GCC | CCA | AGC | CAG | 2671 |
| Phe | Gln | Ala | Ser | Pro | Leu | Gly | Thr | Leu | Val | Thr | Pro | Ala | Pro | Ser | Gln | |
| | | | 820 | | | | | 825 | | | | | 830 | | | |
| GAG | GAC | GAC | TGT | GTC | TTT | GGG | CCA | CTG | CTC | AAC | TTC | CCC | CTC | CTG | CAG | 2719 |
| Glu | Asp | Asp | Cys | Val | Phe | Gly | Pro | Leu | Leu | Asn | Phe | Pro | Leu | Leu | Gln | |
| 835 | | | | | 840 | | | | | 845 | | | | | 850 | |
| GGG | ATC | CGG | GTC | CAT | GGG | ATG | GAG | GCG | CTG | GGG | AGC | TTC | TAGGGCTTCC | | | 2768 |
| Gly | Ile | Arg | Val | His | Gly | Met | Glu | Ala | Leu | Gly | Ser | Phe | | | | |
| | | | | 855 | | | | | 860 | | | | | | | |

TGGGGTTCCC TTCTTGGGCC TGCCTCTTAA AGGCCTGAGC TAGCTGGAGA AGAGGGGAGG  2828
GTCCATAAGC CCATGACTAA AAACTACCCC AGCCCAGGCT CTCACCATCT CCAGTCACCA  2888
GCATCTCCCT CTCCTCCCAA TCTCCATAGG CTGGGCCTCC CAGGCGATCT GCATACTTTA  2948
AGGACCAGAT CATGCTCCAT CCAGCCCCAC CCAATGGCCT TTGTGCTTG TTTCCTATAA  3008
CTTCAGTATT GTAAAC  3024

( 2 ) INFORMATION FOR SEQ ID NO:8:

( i ) SEQUENCE CHARACTERISTICS:
        ( A ) LENGTH: 863 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ala | Arg | Leu | Gly | Asn | Cys | Ser | Leu | Thr | Trp | Ala | Ala | Leu | Ile | Ile |
| 1 | | | | 5 | | | | | 10 | | | | | 15 | |
| Leu | Leu | Leu | Pro | Gly | Ser | Leu | Glu | Glu | Cys | Gly | His | Ile | Ser | Val | Ser |
| | | | 20 | | | | | 25 | | | | | 30 | | |
| Ala | Pro | Ile | Val | His | Leu | Gly | Asp | Pro | Ile | Thr | Ala | Ser | Cys | Ile | Ile |
| | | 35 | | | | | 40 | | | | | 45 | | | |
| Lys | Gln | Asn | Cys | Ser | His | Leu | Asp | Pro | Glu | Pro | Gln | Ile | Leu | Trp | Arg |
| | 50 | | | | | 55 | | | | | 60 | | | | |
| Leu | Gly | Ala | Glu | Leu | Gln | Pro | Gly | Gly | Arg | Gln | Gln | Arg | Leu | Ser | Asp |
| 65 | | | | | 70 | | | | | 75 | | | | | 80 |
| Gly | Thr | Gln | Glu | Ser | Ile | Ile | Thr | Leu | Pro | His | Leu | Asn | His | Thr | Gln |
| | | | | 85 | | | | | 90 | | | | | 95 | |

```
Ala Phe Leu Ser Cys Cys Leu Asn Trp Gly Asn Ser Leu Gln Ile Leu
            100                 105                 110
Asp Gln Val Glu Leu Arg Ala Gly Tyr Pro Pro Ala Ile Pro His Asn
        115                 120                 125
Leu Ser Cys Leu Met Asn Leu Thr Thr Ser Ser Leu Ile Cys Gln Trp
    130                 135                 140
Glu Pro Gly Pro Glu Thr His Leu Pro Thr Ser Phe Thr Leu Lys Ser
145                 150                 155                 160
Phe Lys Ser Arg Gly Asn Cys Gln Thr Gln Gly Asp Ser Ile Leu Asp
                165                 170                 175
Cys Val Pro Lys Asp Gly Gln Ser His Cys Cys Ile Pro Arg Lys His
            180                 185                 190
Leu Leu Leu Tyr Gln Asn Met Gly Ile Trp Val Gln Ala Glu Asn Ala
        195                 200                 205
Leu Gly Thr Ser Met Ser Pro Gln Leu Cys Leu Asp Pro Met Asp Val
    210                 215                 220
Val Lys Leu Glu Pro Pro Met Leu Arg Thr Met Asp Pro Ser Pro Glu
225                 230                 235                 240
Ala Ala Pro Pro Gln Ala Gly Cys Leu Gln Leu Cys Trp Glu Pro Trp
                245                 250                 255
Gln Pro Gly Leu His Ile Asn Gln Lys Cys Glu Leu Arg His Lys Pro
            260                 265                 270
Gln Arg Gly Glu Ala Ser Trp Ala Leu Val Gly Pro Leu Pro Leu Glu
        275                 280                 285
Ala Leu Gln Tyr Glu Leu Cys Gly Leu Leu Pro Ala Thr Ala Tyr Thr
    290                 295                 300
Leu Gln Ile Arg Cys Ile Arg Trp Pro Leu Pro Gly His Trp Ser Asp
305                 310                 315                 320
Trp Ser Pro Ser Leu Glu Leu Arg Thr Thr Glu Arg Ala Pro Thr Val
                325                 330                 335
Arg Leu Asp Thr Trp Trp Arg Gln Arg Gln Leu Asp Pro Arg Thr Val
            340                 345                 350
Gln Leu Phe Trp Lys Pro Val Pro Leu Glu Glu Asp Ser Gly Arg Ile
        355                 360                 365
Gln Gly Tyr Val Val Ser Trp Arg Pro Ser Gly Gln Ala Gly Ala Ile
    370                 375                 380
Leu Pro Leu Cys Asn Thr Thr Glu Leu Ser Cys Thr Phe His Leu Pro
385                 390                 395                 400
Ser Glu Ala Gln Glu Val Ala Leu Val Ala Tyr Asn Ser Ala Gly Thr
                405                 410                 415
Ser Arg Pro Thr Pro Val Val Phe Ser Glu Ser Arg Gly Pro Ala Leu
            420                 425                 430
Thr Arg Leu His Ala Met Ala Arg Asp Pro His Ser Leu Trp Val Gly
        435                 440                 445
Trp Glu Pro Pro Asn Pro Trp Pro Gln Gly Tyr Val Ile Glu Trp Gly
    450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
                485                 490                 495
Phe Gln Leu Tyr Glu Ile Ile Val Thr Pro Leu Tyr Gln Asp Thr Met
            500                 505                 510
Gly Pro Ser Gln His Val Tyr Ala Tyr Ser Gln Glu Met Ala Pro Ser
```

|     |     |     |     |     | 515 |     |     |     |     | 520 |     |     |     |     | 525 |     |     |
| --- | --- | --- | --- | --- | --- | --- | --- | --- | --- | --- | --- | --- | --- | --- | --- | --- | --- |
| His | Ala | Pro | Glu | Leu | His | Leu | Lys | His | Ile | Gly | Lys | Thr | Trp | Ala | Gln |
|     | 530 |     |     |     |     | 535 |     |     |     |     | 540 |     |     |     |     |
| Leu | Glu | Trp | Val | Pro | Glu | Pro | Pro | Glu | Leu | Gly | Lys | Ser | Pro | Leu | Thr |
| 545 |     |     |     |     | 550 |     |     |     |     | 555 |     |     |     |     | 560 |
| His | Tyr | Thr | Ile | Phe | Trp | Thr | Asn | Ala | Gln | Asn | Gln | Ser | Phe | Ser | Ala |
|     |     |     |     | 565 |     |     |     |     | 570 |     |     |     |     | 575 |     |
| Ile | Leu | Asn | Ala | Ser | Ser | Arg | Gly | Phe | Val | Leu | His | Gly | Leu | Glu | Pro |
|     |     |     | 580 |     |     |     |     | 585 |     |     |     |     | 590 |     |     |
| Ala | Ser | Leu | Tyr | His | Ile | His | Leu | Met | Ala | Ala | Ser | Gln | Ala | Gly | Ala |
|     |     | 595 |     |     |     |     | 600 |     |     |     |     | 605 |     |     |     |
| Thr | Asn | Ser | Thr | Val | Leu | Thr | Leu | Met | Thr | Leu | Thr | Pro | Glu | Gly | Ser |
|     | 610 |     |     |     |     | 615 |     |     |     |     | 620 |     |     |     |     |
| Glu | Leu | His | Ile | Ile | Leu | Gly | Leu | Phe | Gly | Leu | Leu | Leu | Leu | Leu | Thr |
| 625 |     |     |     |     | 630 |     |     |     |     | 635 |     |     |     |     | 640 |
| Cys | Leu | Cys | Gly | Thr | Ala | Trp | Leu | Cys | Cys | Ser | Pro | Asn | Arg | Lys | Asn |
|     |     |     |     | 645 |     |     |     |     | 650 |     |     |     |     | 655 |     |
| Pro | Leu | Trp | Pro | Ser | Val | Pro | Asp | Pro | Ala | His | Ser | Ser | Leu | Gly | Ser |
|     |     |     | 660 |     |     |     |     | 665 |     |     |     |     | 670 |     |     |
| Trp | Val | Pro | Thr | Ile | Met | Glu | Glu | Leu | Pro | Gly | Pro | Arg | Gln | Gly | Gln |
|     |     | 675 |     |     |     |     | 680 |     |     |     |     | 685 |     |     |     |
| Trp | Leu | Gly | Gln | Thr | Ser | Glu | Met | Ser | Arg | Ala | Leu | Thr | Pro | His | Pro |
|     | 690 |     |     |     |     | 695 |     |     |     |     | 700 |     |     |     |     |
| Cys | Val | Gln | Asp | Ala | Phe | Gln | Leu | Pro | Gly | Leu | Gly | Thr | Pro | Pro | Ile |
| 705 |     |     |     |     | 710 |     |     |     |     | 715 |     |     |     |     | 720 |
| Thr | Lys | Leu | Thr | Val | Leu | Glu | Glu | Asp | Glu | Lys | Lys | Pro | Val | Pro | Trp |
|     |     |     |     | 725 |     |     |     |     | 730 |     |     |     |     | 735 |     |
| Glu | Ser | His | Asn | Ser | Ser | Glu | Thr | Cys | Gly | Leu | Pro | Thr | Leu | Val | Gln |
|     |     |     | 740 |     |     |     |     | 745 |     |     |     |     | 750 |     |     |
| Thr | Tyr | Val | Leu | Gln | Gly | Asp | Pro | Arg | Ala | Val | Ser | Thr | Gln | Pro | Gln |
|     |     | 755 |     |     |     |     | 760 |     |     |     |     | 765 |     |     |     |
| Ser | Gln | Ser | Gly | Thr | Ser | Asp | Gln | Val | Leu | Tyr | Gly | Gln | Leu | Leu | Gly |
|     | 770 |     |     |     |     | 775 |     |     |     |     | 780 |     |     |     |     |
| Ser | Pro | Thr | Ser | Pro | Gly | Pro | Gly | His | Tyr | Leu | Arg | Cys | Asp | Ser | Thr |
| 785 |     |     |     |     | 790 |     |     |     |     | 795 |     |     |     |     | 800 |
| Gln | Pro | Leu | Leu | Ala | Gly | Leu | Thr | Pro | Ser | Pro | Lys | Ser | Tyr | Glu | Asn |
|     |     |     |     | 805 |     |     |     |     | 810 |     |     |     |     | 815 |     |
| Leu | Trp | Phe | Gln | Ala | Ser | Pro | Leu | Gly | Thr | Leu | Val | Thr | Pro | Ala | Pro |
|     |     |     | 820 |     |     |     |     | 825 |     |     |     |     | 830 |     |     |
| Ser | Gln | Glu | Asp | Asp | Cys | Val | Phe | Gly | Pro | Leu | Leu | Asn | Phe | Pro | Leu |
|     |     | 835 |     |     |     |     | 840 |     |     |     |     | 845 |     |     |     |
| Leu | Gln | Gly | Ile | Arg | Val | His | Gly | Met | Glu | Ala | Leu | Gly | Ser | Phe |
|     | 850 |     |     |     |     | 855 |     |     |     |     | 860 |     |     |     |